(12) United States Patent
Meyerson et al.

(10) Patent No.: US 12,239,646 B2
(45) Date of Patent: Mar. 4, 2025

(54) CANCER DIAGNOSTIC AND TREATMENT

(71) Applicant: DANA-FARBER CANCER INSTITUTE, INC., Boston, MA (US)

(72) Inventors: Matthew Meyerson, Boston, MA (US); Susan Bullman, Boston, MA (US)

(73) Assignee: DANA-FARBER CANCER INSTITUTE, INC., Boston, MA (US)

(*) Notice: Subject to any disclaimer, the term of this patent is extended or adjusted under 35 U.S.C. 154(b) by 0 days.

(21) Appl. No.: 16/632,368

(22) PCT Filed: Jul. 19, 2018

(86) PCT No.: PCT/US2018/042966
§ 371 (c)(1),
(2) Date: Jan. 19, 2020

(87) PCT Pub. No.: WO2019/018694
PCT Pub. Date: Jan. 24, 2019

(65) Prior Publication Data
US 2020/0405720 A1  Dec. 31, 2020

Related U.S. Application Data

(60) Provisional application No. 62/534,672, filed on Jul. 19, 2017.

(51) Int. Cl.
*A61K 31/513* (2006.01)
*A61K 31/4164* (2006.01)
*A61K 45/06* (2006.01)
*C12Q 1/04* (2006.01)
*C12Q 1/689* (2018.01)

(52) U.S. Cl.
CPC ........ *A61K 31/513* (2013.01); *A61K 31/4164* (2013.01); *A61K 45/06* (2013.01); *C12Q 1/04* (2013.01); *C12Q 1/689* (2013.01)

(58) Field of Classification Search
None
See application file for complete search history.

(56) References Cited

U.S. PATENT DOCUMENTS

| | | |
|---|---|---|
| 3,326,761 A | 6/1967 | Kent |
| 4,971,903 A | 11/1990 | Hyman |
| 5,202,231 A | 4/1993 | Drmanac et al. |
| 5,403,708 A | 4/1995 | Brennan et al. |
| 5,445,934 A | 8/1995 | Fodor et al. |
| 5,525,464 A | 6/1996 | Drmanac et al. |
| 5,547,839 A | 8/1996 | Dower et al. |
| 5,695,940 A | 12/1997 | Drmanac et al. |
| 5,795,782 A | 8/1998 | Church et al. |
| 5,902,723 A | 5/1999 | Dower et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 10,266,886 B2 * | 4/2019 | Abudayyeh ............ C12Q 1/68 |
| 2010/0029498 A1 | 2/2010 | Gnirke et al. |
| 2010/0040614 A1 | 2/2010 | Ahmed |
| 2013/0230857 A1 | 9/2013 | Gnirke et al. |
| 2014/0107092 A1 * | 4/2014 | Meyerson ............. C12Q 1/689 |
| | | 435/6.12 |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0200163 A1 | 7/2014 | Mikkelsen et al. |
| 2014/0206011 A1 * | 7/2014 | Han ..................... C12Q 1/6886 |
| | | 435/39 |

(Continued)

FOREIGN PATENT DOCUMENTS

| | | |
|---|---|---|
| EP | 2 764 103 B1 | 8/2014 |
| EP | 2 771 468 B1 | 9/2014 |

(Continued)

OTHER PUBLICATIONS

Beyaz et al. "High-fat diet enhances stemness and tumorigenicity of intestinal progenitors," Nature 531, 54. (Year: 2016).*

Yu et al. "Invasive Fusobacterium nucleatum may play a role in the carcinogenesis of proximal colon cancer through the serrated neoplasia pathway," Int. J. Cancer: 139, 1318-1326 (2016). (Year: 2016).*

Wilhelm et al. "Prospective, Multicenter Study of 5-Fluorouracil Therapeutic Drug Monitoring in Metastatic Colorectal Cancer Treated in Routine Clinical Practice," Clinical Colorectal Cancer, vol. 15, No. 4, 381-8; (Year: 2016).*

Vanlancker et al. "5-Fluorouracil sensitivity varies among oral microorganisms," Journal of Medical Microbiology (2016), 65, 775-783. (Year: 2016).*

(Continued)

*Primary Examiner* — Jeffrey S Lundgren
*Assistant Examiner* — Michael J Schmitt
(74) *Attorney, Agent, or Firm* — Foley & Lardner LLP; Sunit Talapatra

(57) ABSTRACT

Bacterial species and the associated microbiome persist in tumors and metastases. Antibiotic treatment selectively reduces microbiome-induced tumor growth and can advantageously be included in treatment regimens. Accordingly, the present disclosure relates to, for example, the diagnosing cancer in a subject and providing identifying an effective treatment regimen for the subject.

24 Claims, 26 Drawing Sheets

Specification includes a Sequence Listing.

(56) References Cited

U.S. PATENT DOCUMENTS

| | | | |
|---|---|---|---|
| 2014/0227787 A1 | 8/2014 | Zhang | |
| 2014/0228223 A1 | 8/2014 | Gnirke et al. | |
| 2014/0234972 A1 | 8/2014 | Zhang | |
| 2014/0242664 A1 | 8/2014 | Zhang et al. | |
| 2014/0242699 A1 | 8/2014 | Zhang | |
| 2014/0242700 A1 | 8/2014 | Zhang et al. | |
| 2014/0248702 A1 | 9/2014 | Zhang et al. | |
| 2014/0256046 A1 | 9/2014 | Zhang et al. | |
| 2014/0273231 A1 | 9/2014 | Zhang et al. | |
| 2014/0273232 A1 | 9/2014 | Zhang et al. | |
| 2014/0273234 A1 | 9/2014 | Zhang et al. | |
| 2014/0287938 A1 | 9/2014 | Zhang et al. | |
| 2014/0310830 A1 | 10/2014 | Zhang et al. | |
| 2015/0126377 A1 | 5/2015 | Gnirke et al. | |
| 2016/0220619 A1 | 8/2016 | Lee | |
| 2016/0223553 A1* | 8/2016 | Sears | A61K 31/7056 |

FOREIGN PATENT DOCUMENTS

| | | |
|---|---|---|
| EP | 2 784 162 B1 | 10/2014 |
| WO | WO-93/23564 A1 | 11/1993 |
| WO | WO-96/39154 A1 | 12/1996 |
| WO | WO-97/03211 A1 | 1/1997 |
| WO | WO-98/13523 A1 | 4/1998 |
| WO | WO-98/28440 A1 | 7/1998 |
| WO | WO-2009/099602 A1 | 8/2009 |
| WO | WO-2014/018423 A1 | 1/2014 |
| WO | WO-2014/047556 A1 | 3/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/204723 A1 | 12/2014 |
| WO | WO-2014/204724 A1 | 12/2014 |
| WO | WO-2014/204725 A1 | 12/2014 |
| WO | WO-2014/204726 A1 | 12/2014 |
| WO | WO-2014/204727 A1 | 12/2014 |
| WO | WO-2014/204728 A1 | 12/2014 |
| WO | WO-2014/204729 A1 | 12/2014 |

OTHER PUBLICATIONS

Beyaz et al. "High-fat diet enhances stemness and tumorigenicity of intestinal progenitors," Nature 2016, 531, 54. (Year: 2016).*

International Search Report for PCT/US2018/042966 issued by the U.S. Patent Office, as International Searching Authority on Nov. 15, 2018.

Written Opinion of the International Searching Authority for PCT/US2018/042966 issued by the U.S. Patent Office, as International Searching Authority on Nov. 15, 2018.

"ChandraPedamallu / PathSeq", https://github.com/ChandraPedamallu/P, downloaded from the internet Jan. 15, 2020.

Abed, et al., "Fap2 Mediates Fusobacterium nucleatum Colorectal Adenocarcinoma Enrichment by Binding to Tumor-Expressed Gal-GalNAc", Cell Host and Microbe, vol. 20, No. 2, Aug. 10, 2016, 215-225.

Ahn, et al., "Human Gut Microbiome and Risk for Colorectal Cancer", Journal of the National Cancer Institute, vol. 105, No. 24, Dec. 18, 2013, 1907-1911.

Altschul, et al., "Gapped BLAST and PSI-BLAST: A New Generation of Protein Database Search Programs", Nucleic Acids Research, vol. 25, No. 17, Sep. 1997, 3389-3402.

Ananthakrishnan, et al., "A Prospective Study of Long-term Intake of Dietary Fiber and Risk of Crohn's Disease and Ulcerative Colitis", Gastroenterology, vol. 145, No. 5, Nov. 2013, 970-977.

Arthur, et al., "Intestinal Inflammation Targets Cancer-Inducing Activity of The Microbiota", Science, vol. 338, No. 6103, Oct. 5, 2012, 120-123.

Aune, et al., "Dietary Fibre, Whole Grains, and Risk of Colorectal Cancer: Systematic Review and Dose-response Meta-analysis of Prospective Studies", BMJ, vol. 343, 2011, 20 pages.

Aziz, et al., "The Rast Server: Rapid Annotations Using Subsystems Technology", BMC Genomics, vol. 9, Feb. 8, 2008, 1-15.

Cancer Genome Atlas Network, "Comprehensive Molecular Characterization of Human Colon and Rectal Cancer", Nature, vol. 4807, No. 7407, Jul. 18, 2012, 330-337.

Castellarin, et al., "Fusobacterium Nucleatum Infection is Prevalent in Human Colorectal Carcinoma", Genome Research, vol. 22, No. 2, Feb. 2012, 299-306.

Chen, et al., "Decreased Dietary Fiber Intake and Structural Alteration of Gut Microbiota in Patients with Advanced Colorectal Adenoma", The American Journal of Clinical Nutrition, vol. 97, No. 5, May 2013, 1044-1052.

Claesson, et al., "Gut Microbiota Composition Correlates with Diet and Health in the Elderly", Nature, vol. 488, No. 7410, Jul. 2012, 178-184.

Cotillard, et al., "Dietary Intervention Impact on Gut Microbial Gene Richness", Nature, vol. 500, No. 7464, Aug. 2013, 558-588.

Cottet, et al., "Dietary Patterns and the Risk of Colorectal Adenoma Recurrence in a European Intervention Trial", European Journal of Cancer Prevention, vol. 14, No. 1, 21-29., Feb. 1, 2005.

De Filippis, et al., "High-level Adherence to a Mediterranean Diet Beneficially Impacts the Gut Microbiota and Associated Metabolome", Gut, vol. 65, No. 11, Nov. 2016, 1812-1821.

Dejea, et al., "Microbiota Organization is a Distinct Feature of Proximal Colorectal Cancers", Proceedings of the National Academy of Sciences of the United States of America, vol. 111, No. 51, Dec. 23, 2014, 18321-18326.

Destefano Shields, et al., "Reduction of Murine Colon Tumorigenesis Driven by Enterotoxigenic Bacteroides fragilis Using Cefoxitin Treatment", The Journal of Infectious Disease, vol. 214, pp. 122-129.

Durbin, et al., "Fast and Accurate Short Read Alignment with Burrows-Wheeler Transform", Bioinformatics Oxford English, vol. 25, No. 14, May 12, 2009, 1754-1760.

Flanagan, et al., "Fusobacterium Nucleatum Associates with Stages of Colorectal Neoplasia Development, Colorectal Cancer and Disease Outcome", European Journal of Clinical Microbiology & Infectious Diseases, vol. 33, No. 8, Aug. 2014, 1381-1390.

Flemer, et al., "Tumour-associated and non-tumour-associated microbiota in colorectal cancer", Gut Microbiota, Mar. 15, 2015, pp. 1-11.

Flood, et al., "Dietary Patterns as Identified by Factor Analysis and Colorectal Cancer among Middle-Aged Americans", The American Journal of Clinical Nutrition, vol. 88, No. 1, Jul. 2008, 176-184.

Fu, et al., "Characterization of the Gut Microbiome in Epidemiologic Studies: The Multiethnic Cohort Experience", Annals of Epidemiology, vol. 26, No. 5, May 2016, 373-379.

Fung, et al., "Major Dietary Patterns and the Risk of Colorectal Cancer in Women", Archives of Internal Medicine, vol. 163, No. 3, Feb. 10, 2003, 309-314.

Garrett, "Cancer and the Microbiota", Science, vol. 348, No. 6230, Apr. 3, 2015, 80-86.

Gire, et al., "Genomic Surveillance Elucidates Ebola Virus Origin and Transmission During The 2014 Outbreak", Science, vol. 345, No. 6202, Sep. 12, 2014, 1369-1372.

Grant, et al., "The CGView Server: A Comparative Genomics Tool for Circular Genomes", Nucleic Acids Research, vol. 36, Jul. 1, 2008, W181-W184.

Gur, et al., "Binding of The Fap2 Protein of Fusobacterium Nucleatum to Human Inhibitory Receptor Tigit Protects Tumors from Immune Cell Attack", Immunity, vol. 42, No. 2, Feb. 17, 2015, 344-355.

Hamada, et al., "Molecular Pathological Epidemiology: New Developing Frontiers of Big Data Science to Study Etiologies and Pathogenesis", Journal of Gastroenterology, vol. 52, No. 3, Mar. 2017, 265-275.

Hope, et al., "Sporadic Colorectal Cancer—Role of The Commensal Microbiota", FEMS Microbiology Letters, vol. 244, No. 1, Mar. 1, 2005, 1-7.

(56) References Cited

OTHER PUBLICATIONS

Hu, et al., "Prospective Study of Major Dietary Patterns and Risk of Coronary Heart Disease in Men", The American Journal of Clinical Nutrition, vol. 72, 2000, 92-921.

Ito, et al., "Association of Fusobacterium Nucleatum with Clinical and Molecular Features in Colorectal Serrated Pathway", International Journal of Cancer, vol. 137, No. 6, Sep. 2015, 1258-1268.

Kim, et al., "Dietary Patterns and Subsequent Colorectal Cancer Risk by Subsite: A Prospective Cohort Study", International Journal of Cancer, vol. 115, No. 5, Jul. 10, 2005, 790-798.

Koeth, et al., "Intestinal Microbiota Metabolism of L-carnitine, a Nutrient in Red Meat, Promotes Atherosclerosis", Nature Medicine, vol. 19, No. 5, May 2013, 576-585.

Kolenbrander, "Adhere Today, Here Tomorrow: Oral Bacterial Adherence", Journal of Bacteriology, vol. 175, No. 11, Jun. 1993, 3247-325.

Kolenbrander, "Coaggregation of Fusobacterium Nucleatum, Selenomonas Flueggei, Selenomonas Infelix, Selenomonas Noxia, and Selenomonas Sputigena with Strains From 11 Genera of Oral Bacteria", Infection and Immunity, vol. 57, No. 10, Oct. 1989, 3194-3203.

Kolenbrander, et al., "Inhibition of Coaggregation between Fusobacterium Nucleatum and Porphyromonas (Bacteroides) Gingivalis by Lactose and Related Sugars", Infection and Immunity, vol. 57, No. 10, Oct. 1989, 3204-3209.

Kostic, et al., "Fusobacterium Nucleatum Potentiates Intestinal Tumorigenesis and Modulates The Tumor-Immune Microenvironment", Cell Host and Microbe, vol. 14, No. 2, Aug. 14, 2013, 207-215.

Kostic, et al., "Genomic Analysis Identifies Association of Fusobacterium with Colorectal Carcinoma", Genome Research, vol. 22, No. 2, Feb. 2012, 292-298.

Kostic, et al., "Pathseq: Software to Identify or Discover Microbes by Deep Sequencing of Human Tissue", Nature Biotechnology, vol. 29, No. 5, May 2011, 393-396.

Le Chatelier, et al., "Richness of Human Gut Microbiome Correlates with Metabolic Markers", Nature, vol. 500, Aug. 2013, 541-546.

Li, et al., "Association of Fusobacterium Nucleatum Infection with Colorectal Cancer in Chinese patients", World Journal of Gastroenterology, vol. 22, No. 11, Mar. 21, 2016, 3227-3233.

Lofmark, et al., "Metronidazole is still the Drug Of Choice for Treatment of Anaerobic Infections", Clinical Infectious Diseases, vol. 50, Jan. 1, 2010, S16-S23.

Magalhaes, et al., "Dietary Patterns and Colorectal Cancer: Systematic Review and Meta-analysis", European Journal of Cancer Prevention, vol. 21, No. 1, Jan. 2012, 15-23.

Markowitz, et al., "IMG ER: A System for Microbial Genome Annotation Expert Review and Curation", Bioinformatics, vol. 25, No. 17, Sep. 1, 2009, 2271-2278.

Martin, "Quantitative Microbiological Study of Human Carious Dentine by Culture and Real-Time PCR: Association of Anaerobes with Histopathological Changes in Chronic Pulpitis", Journal of Clinical Microbiology, vol. 40, No. 5, May 2002, 1698-1704.

McCoy, et al., "Fusobacterium is associated with Colorectal Adenoma", PLoS One, vol. 8, No. 1, Jan. 15, 2013, 8 pages.

Microbewiki, "Fusobacterium Nucleatum", https://microbewiki.kenyon.edu/index.php?title+Fusobacterium_nucleatum&oldid=54788.

Mima, et al., "Fusobacterium Nucleatum and T Cells in Colorectal Carcinom", JAMA Oncology, vol. 1, No. 5, Aug. 2015, 653-661.

Mima, et al., "Fusobacterium Nucleatum in Colorectal Carcinoma Tissue According to Tumor Location", Clinical and Translational Gastroenterology, vol. 7, No. 11, 2016, 8 pages.

Mima, et al., "Fusobacterium Nucleatum in Colorectal Carcinoma Tissue and Patient Prognosis", Gut, vol. 65, No. 12, Dec. 2016, 1973-1980.

Mizoue, et al., "Dietary Patterns and Colorectal Adenomas in Japanese Men: The Self-Defense Forces Health Study", American Journal of Epidemiology, vol. 116, No. 4, 2005, 338-345.

Nakatsu, et al., "Gut Mucosal Microbiome across Stages of Colorectal Carcinogenesis", Nature Communications, vol. 6, Oct. 30, 2015, 1-9.

Nosho, et al., "Association of Fusobacterium Nucleatum with Immunity and Molecular Alterations in Colorectal Cancer", World Journal of Gastroenterology, vol. 22, No. 2, Jan. 2016, 557-566.

Ogino, et al., "Molecular Pathologic Epidemiology of Colorectal Neoplasia: An Emerging Transdisciplinary and Interdisciplinary Field", Gut, vol. 60, No. 3, Mar. 2011, 397-411.

Ogino, et al., "The Role of Molecular Pathological Epidemiology in the Study of Neoplastic and Non-Neoplastic Diseases in the Era of Precision Medicine", Epidemiology, vol. 27, No. 4, Jul. 27, 2016, 602-611.

O'Keefe, et al., "Fat, Fibre and Cancer Risk in African Americans and Rural Africans", Nature Communications, vol. 6, Article No. 6342, 2015, 14 pages.

Ou, et al., "Diet, Microbiota, and Microbial Metabolites in Colon Cancer Risk in Rural Africans and African Americans", The American Journal of Clinical Nutrition, vol. 98, Issue 1, Jul. 2013, 111-120.

Rimm, et al., "Reproducibility and Validity of an Expanded Self-Administered Semiquantitative Food Frequency Questionnaire among Male Health Professionals", American Journal of Epidemiology, vol. 135, No. 10, Jun. 1992, 1127-1136.

Rowland, "The Role of the Gastrointestinal Microbiota in Colorectal Cancer", Current Pharmaceutical Design, vol. 15, No. 13, 2009, 1524-1527.

Rubinstein, et al., "Fusobacterium Nucleatum Promotes Colorectal Carcinogenesis by Modulating E-Cadherin/B- Catenin Signaling Via Its Fada Adhesin", Cell Host and Microbe, vol. 14, No. 2, Aug. 14, 2013, 195-206.

Schwabe, et al., "The Microbiome and Cancer", Nature Reviews Cancer, vol. 13, No. 11, Nov. 2013, 800-812.

Segata, et al., "Metagenomic Biomarker Discovery and Explanation", Genome Biology, vol. 12, No. 60, Jun. 24, 2011, 1-18.

Shields, et al., "Reduction of Murine Colon Tumorigenesis Driven by Enterotoxigenic Bacteroides fragilis Using Cefoxitin Treatment", The Journal of Infectious Diseases, vol. 214, Issue 1, Jul. 1, 2016, 122-129.

Sinha, et al., "Fecal Microbiota, Fecal Metabolome, and Colorectal Cancer Interrelations", Plos One, vol. 11, No. 3, Mar. 25, 2016, 1-13.

Smith, et al., "The Microbial Metabolites, Short-chain Fatty Acids, Regulate Colonic Treg Cell Homeostasis", Science, vol. 341, No. 6145, Aug. 2013, 569-573.

Song, et al., "Nutrients, Foods, and Colorectal Cancer Prevention", Gastroenterology, vol. 148, No. 6, May 2015, 1244-1260.

Sonnenburg, et al., "Diet-induced Extinction in the Gut Microbiota Compounds Over Generations", Nature, vol. 529, No. 7585, Jan. 14, 2016, 212-215.

Tahara, et al., "Fusobacterium in Colonic Flora and Molecular Features of Colorectal Carcinom", Cancer Research, vol. 74, No. 5, Mar. 1, 2014, 1311-1318.

Takimoto, et al., "High Inter- and Intrapatient Variation in 5-Fluorouracil Plasma Concentrations during a Prolonged Drug Infusion", Clinical Cancer Research, vol. 5, Issue 6, Jun. 1999, 1347-1352.

Terry, et al., "Prospective Study of Major Dietary Patterns and Colorectal Cancer Risk in Women", American Journal of Epidemiology, vol. 154, Issue 12, Dec. 15, 2001, 1143-1149.

Tuddenham, et al., "The Intestinal Microbiome and Health", Current Opinion in Infectious Diseases, vol. 28, No. 5, 2015, 464-470.

Viljoen, et al., "Quantitative Profiling of Colorectal Cancer-Associated Bacteria Reveals Associations between *Fusobacterium* spp., Enterotoxigenic Bacteroides fragilis (ETBF) and Clinicopathological Features of Colorectal Cancer", Plos One, vol. 10, Mar. 9, 2015, 1-21.

Wang, et al., "Statistical Methods for Studying Disease Subtype Heterogeneity", Statistics in Medicine, vol. 35, No. 5, Feb. 28, 2016, 782-800.

Warren, et al., "Co-Occurrence of Anaerobic Bacteria in Colorectal Carcinomas", Microbiome, vol. 1, No. 1, May 15, 2013, 12 pages.

(56) References Cited

OTHER PUBLICATIONS

World Cancer Research Fund, "Food, Nutrition, Physical Activity, and the Prevention of Colorectal Cancer", American Institute for Cancer Research, Colorectal Cancer Report 2011, 2011, 43 pages.
Wu, et al., "A Human Colonic Commensal Promotes Colon Tumorigenesis Via Activation of T Helper type 17 T Cell Responses", Nature Medicine, vol. 15, No. 9, Sep. 2009, 1016-1022.
Wu, et al., "Linking Long-Term Dietary Patterns with Gut Microbial Enterotypes", Science, vol. 334, No. 6052, Oct. 2011, 105-108.
Yang, et al., "Bacteria, Inflammation, and Colon Cancer", World Journal of Gastroenterology, vol. 12, No. 42, Nov. 14, 2006, 6741-6746.
Yang, et al., "Fusobacterium nucleatum Increases Proliferation of Colorectal Cancer Cells and Tumor Development in Mice by Activating Toll-Like Receptor 4 Signaling to Nuclear Factor-κB, and Up-regulating Expression of MicroRNA-21", Gastroenterology, vol. 152, No. 4, Mar. 2017, 851-866.
Zerbino, et al., "Velvet: Algorithms for De Novo Short Read Assembly Using De Bruijn Graphs", Genome Research, vol. 18, No. 5, May 2008, 821-829.
Altschul et al., "Basic local alignment search tool," Journal of Molecular Biology, 1990, vol. 215 (pp. 403-410).
Bass et al., "Genomic sequencing of colorectal adenocarcinomas identifies a recurrent VTI1A-TCF7L2 fusion," Nature Genetics, 2011, vol. 43, No. 10 (pp. 964-968).
Canard et al., "DNA polymerase fluorescent substrates with reversible 3'-tags," Gene, Oct. 11, 1994, vol. 148, No. 1 (pp. 1-6).
Chen et al., "Genome-wide CRISPR Screen in a Mouse Model of Tumor Growth and Metastasis," Cell, 2015 vol. 160 (pp. 1-15).
Chung et al., "Structural and molecular interrogation of intact biological systems," Nature, May 16, 2013, vol. 497 (pp. 332-337).
Cong et al., "CRISPR-Assisted Mammalian Genome Engineering," published as "Multiplex Genome Engineering Using CRISPR-Cas Systems," Science, Oct. 5, 2012, vol. 339 (pp. 819-823) [Manuscript including Supplementary Materials—36 pages].
Dahlman et al., "Orthogonal gene control with a catalytically active Cas9 nuclease," Nature Biotechnology, Nov. 2015, vol. 33, No. 11 (pp. 1159-1161).
Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].
Drmanac et al., "Sequencing of megabase plus DNA by hybridization: theory of the method," Genomics, Feb. 1989, vol. 4, No. 2 (pp. 114-128).
Dyatkina et al., "Terminating substrates of DNA polymerases: synthesis and functional study," Nucleic Acids Symposium Series, Jan. 1, 1987, vol. 18 (pp. 117-120).
Elgen et al., "Sorting single molecules: application to diagnostics and evolutionary biotechnology," Proceedings of the National Academy of Sciences, USA, Jun. 1994, vol. 91 (pp. 55740-5747).
Empedocles et al., "Three-dimensional orientation measurements of symmetric single chromophores using polarization microscopy," Nature, 1999, vol. 399 (pp. 126-130).
Gao et al., "Engineered Cpf1 enzymes with altered PAM specificities," bioRxiv preprint, Dec. 4, 2016 [pp. 1/14-14/14, pp. 1/3-3/3 of Figs, and pp. S1-S8 (25 pages)].
Geniez et al., "Targeted genome enrichment for efficient purification of endosymbiont DNA from host DNA," Symbiosis, Jan. 6, 2013, vol. 58 (pp. 201-207).
Gire et al., "Genomic Surveillance Elucidates Ebola Virus Origin and Transmission During The 2014 Outbreak", Science, Sep. 12, 2014, vol. 345, No. 6202 (pp. 1369-1372).
Gnirke et al., "Solution hybrid selection with ultra-long oligonucleotides for massively parallel targeted sequencing," Nature Biotechnology, Feb. 2009, vol. 27, No. 2 (pp. 182-189).
Gootenberg et al., "Nucleic acid detection with CRISPR-Cas13a/C2c2," Science, Apr. 28, 2017, vol. 356 (pp. 438-442).
Hsu et al., "Development and Applications of CRISPR-Cas9 for Genome Engineering," Cell, 2014, vol. 157 (pp. 1262-1278).
Hsu et al., "DNA targeting specificity of RNA-guided Cas9 nucleases," Nature Biotechnology, Sep. 2013, vol. 31, No. 9 (pp. 827-832).
Hyman et al., "A new method of sequencing DNA," Analytical Biochemistry, Nov. 1, 1988, vol. 174, No. 2 (pp. 423-436).
Jiang et al., "RNA-guided editing of bacterial genomes using CRISPR-Cas systems," Nature Biotechnology, Mar. 2013, vol. 31 [30 pages, including supplementary information] (pp. 233-239).
Johnson et al., "Continuous assay for DNA polymerization by light scattering," Analytical Biochemistry, Jan. 1984, vol. 136, No. 1 (pp. 192-194).
Jones, D.H., "An iterative and regenerative method for DNA sequencing," BioTechniques, May 1997, vol. 22 (pp. 938-946).
Konermann et al., "Genome-scale transcriptional activation by an engineered CRISPR-Cas9 complex," Nature, 2015, vol. 517 (pp. 583-588) [Including Supplemental information, 12 pages].
Konermann et al., "Optical control of mammalian endogenous transcription and epigenetic states," Nature, Aug. 22, 2013, vol. 500, Includes Supplemental Information (pp. 472-476).
Koster et al., "A strategy for rapid and efficient DNA sequencing by mass spectrometry," Nature Biotechnology, Sep. 1996, vol. 14 (pp. 1123-1128).
Lane, D.J., "16S/23S rRNA sequencing," Nucleic acid techniques in bacterial systematics, Nucleic Acid Techniques in Bacterial Systematics, Chapter 6, 1991 (pp. 125-175).
Matranga et al., "Enhanced methods for unbiased deep sequencing of Lassa and Ebola RNA viruses from clinical and biological samples," Genome Biology, 2014, vol. 15, No. 519 (pp. 1-12).
Melnikov et al., "Hybrid selection for sequencing pathogen genomes from clinical samples," Genome Biology, Aug. 11, 2011, vol. 12, No. R73, (pp. 1-9).
Metzker et al., "Termination of DNA synthesis by novel 3'-modified-deoxyribonucleoside 5'-triphosphates," Nucleic Acids Research, 1994, vol. 22, No. 20 (pp. 4259-4267).
Nishimasu et al., "Crystal Structure of Cas9 in Complex with Guide RNA and Target DNA," Cell, Feb. 27, 2014, vol. 156 (pp. 935-949).
Nishimasu et al., "Crystal Structure of Staphylococcus aureus Cas9", Cell, 2015, vol. 162 (pp. 1113-1126) [with Supplemental Information].
Nyren et al., "Enzymatic method for continuous monitoring of inorganic pyrophosphate synthesis," Analytical Biochemistry, Dec. 1985, vol. 151, No. 2 (pp. 504-509).
Parnas et al., "A Genome-Wide CRISPR Screen in Primary Immune Cells to Dissect Regulatory Networks," 2015, vol. 162 (pp. 675-686) [with Supplementary Information].
Platt et al., "CRISPR-Cas9 Knockin Mice for Genome Editing and Cancer Modeling," Cell, 2014, vol. 159 (pp. 440-455).
Ramanan et al., "CRISPR-Cas9 cleavage of viral DNA efficiently suppresses hepatitis B virus," Nature/Scientific Reports, Jun. 2015 (9 pages).
Ran et al., "Double Nicking by RNA-guided CRISPR Cas9 for enhanced genome editing specificity", Cell, Sep. 12, 2013, vol. 154 (pp. 1380-1389).
Ran et al., "Genome engineering using the CRISPR-Cas9 system," Nature Protocols, 2013, vol. 8 (pp. 2281-2308).
Ran et al., "In vivo genome editing using Staphylococcus aureus Cas9," Nature, vol. 520, 2015, (pp. 186-191). [Includes Supplemental information, 12 pages].
Reichert et al., "Chip-Based Optical Detection of DNA Hybridization by Means of Nanobead Labeling," Analytical Chemistry, Dec. 15, 2000, vol. 72, No. 24 (pp. 6025-6029).
Ronaghi et al., "A Sequencing Method Based on Real-Time Pyrophosphate," Science, Jul. 17, 1988, vol. 281, No. 5375 (pp. 363-365).
Ronaghi et al., "Real-time DNA sequencing using detection of pyrophosphate release," Analytical Biochemistry, 1996, vol. 242, Article 0432 (pp. 84-89).
Sanger et al., "DNA sequencing with chain-terminating inhibitors," Proceedings of the National Academy of Sciences, USA, Dec. 1977, vol. 74, No. 12 (pp. 5463-5467).
Shalem et al., "Genome-Scale CRISPR-Cas9 Knockout Screening in Human Cells," Science, Jan. 3, 2014, vol. 343 (pp. 84-87).
Shalem et al., "High-throughput functional genomics using CRISPR-Cas9" Nature Review Genetics, 2015, vol. 16, No. 5 (pp. 299-311).

(56) References Cited

OTHER PUBLICATIONS

Shiroguchi et al., "Digital RNA sequencing minimizes sequence-dependent bias and amplification noise with optimized single-molecule barcodes," Proceedings of the National Academy of Sciences, USA, Jan. 24, 2012, vol. 109, No. 4 (pp. 1347-1352).
Shmakov et al., "Discovery and Functional Characterization of Diverse Class 2 CRISPR-Cas Systems," Molecular Cell, Nov. 1, 2015, vol. 60, No. 3 (pp. 385-397).
Smargon et al., "Cas13b Is a Type VI-B CRISPR-Associated RNA-Guided RNases Differentially Regulated by Accessory Proteins Csx27 and Csx28," Cell Press: Molecular Cell, Feb. 16, 2017, vol. 65, No. 4 (pp. 618-630).
Sorek et al., "A novel algorithm for computational identification of contaminated EST libraries," Nucleic Acids Research, 2003, vol. 31, No. 3 (pp. 1067-1074).
Swiech et al., "In vivo interrogation of gene function in the mammalian brain using CRISPR-Cas9," Nature Biotechnology, 2014, vol. 33 (pp. 102-106) [Including Supplemental information, 4 pages].
Wang et al., "Genetic screens in human cells using the CRISPR/Cas9 system," Science, Jan. 3, 2014, vol. 343 No. 6166 (pp. 80-84).
Wang et al., "One-Step Generation Of Mice Carrying Mutations In Multiple Genes By CRISPR/Cas-Mediated Genome Engineering," Cell, May 9, 2013, vol. 153 (pp. 910-918).
Weber et al., "Identification of foreign gene sequences by transcript filtering against the human genome," Nature Genetics, Feb. 2002, vol. 30, Issue 2 (pp. 141-142)—(22 pages with Supplemental Information).
Wu et al., "Genome-wide binding of the CRISPR endonuclease Cas9 in mammalian cells," Nature Biotechnology, 2014, Including Supplemental information, 2 pages (pp. 1-9).
Xu et al., "Sequence determinants of improved CRISPR sgRNA design," Genome Research, Aug. 2015, vol. 25 (pp. 1147-1157).
Zetsche at el., "Cpf1 Is a Single RNA-Guided Endonuclease of a Class 2 CRISPR-Cas System," Cell, Oct. 22, 2015, vol. 163, No. 3 (pp. 759-771).
Zetsche et al., "A split-Cas9 architecture for inducible genome editing and transcription modulation", Nature Biotechnology, Feb. 2015, vol. 33, No. 2 (pp. 139-142).

* cited by examiner

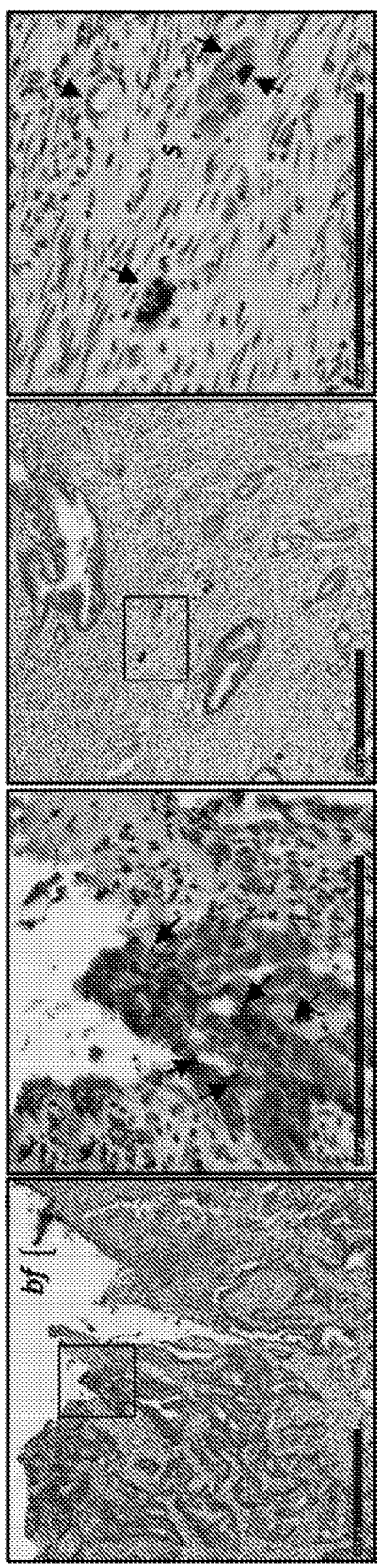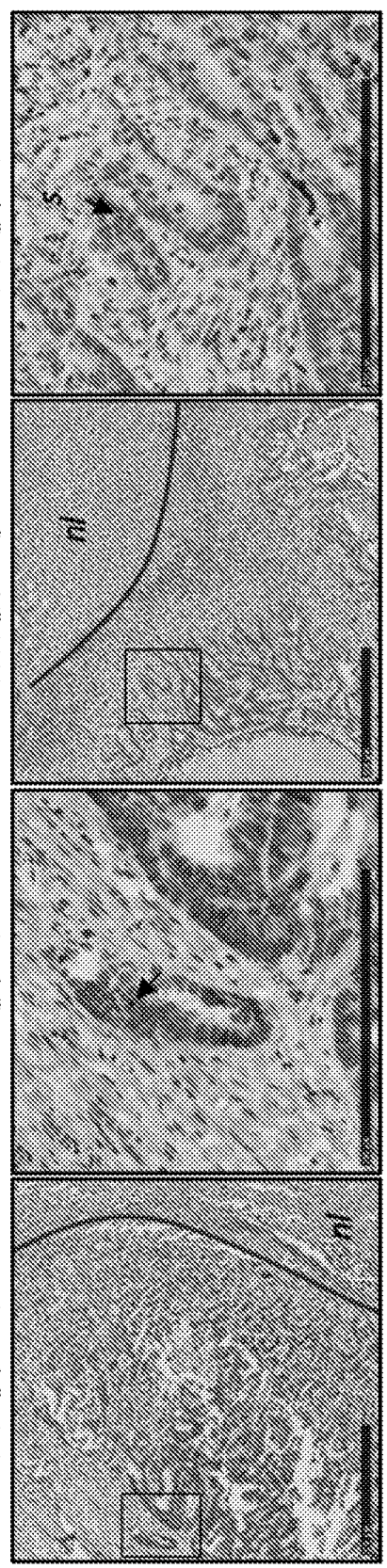

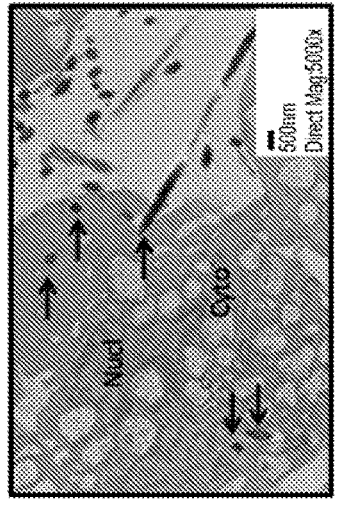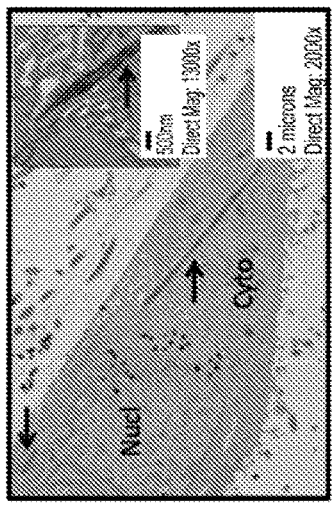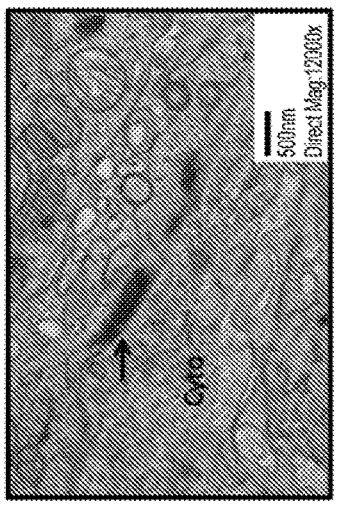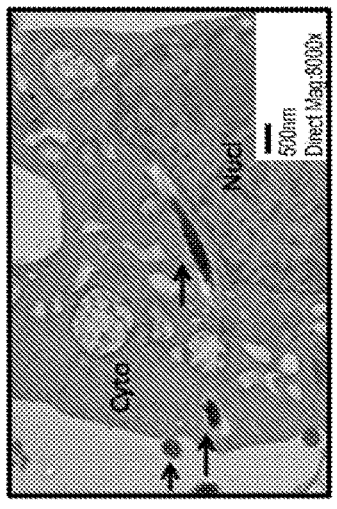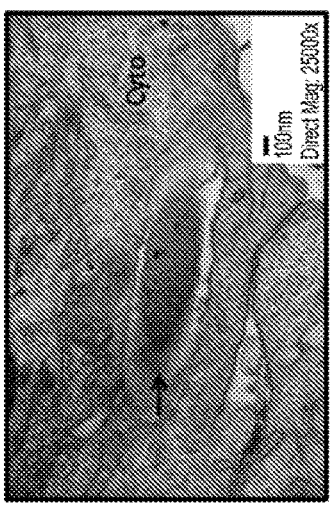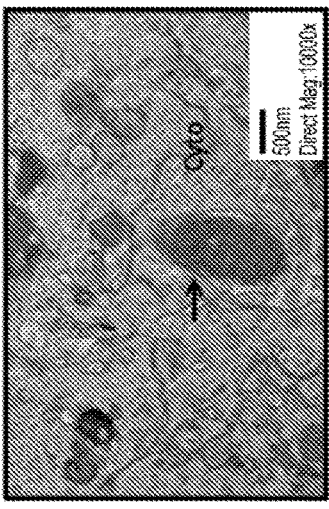
FIG. 4A  FIG. 4B  FIG. 4C  FIG. 4D

| PDX Success | Tumor Grade | |
|---|---|---|
| | High | Low |
| Yes | 4 | 2 |
| No | 1 | 6 |

Fischer's exact p=0.1

FIG. 11A

| Fusobacterium | Tumor Grade | |
|---|---|---|
| | High | Low |
| Culture Pos | 4 | 1 |
| Culture Neg | 1 | 7 |

Fischer's exact p=0.03

FIG. 11B

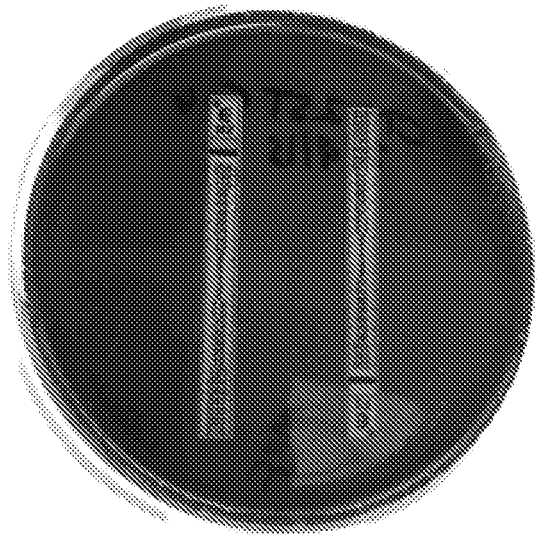 
FIG. 14

Tumors treated with 5FU or a 5-FU prodrug (n=43)

| Fusobacterium | Recurrence | |
|---|---|---|
| | Yes | No |
| High* | 6 | 26 |
| Low/Neg | 6 | 5 |

Fischer's exact p=0.047
Z- score two population proportions p=0.02

Tumors with no treatment information (n=48)

| Fusobacterium | Recurrence | |
|---|---|---|
| | Yes | No |
| High* | 17 | 19 |
| Low/Neg | 6 | 6 |

Fischer's exact p>0.999

FIG. 20

CANCER DIAGNOSTIC AND TREATMENT

CROSS-REFERENCE TO RELATED APPLICATIONS

This application is a U.S. National Stage of International Application No. PCT/US2018/042966, filed Jul. 19, 2018, which claims the benefit of U.S. Provisional Application No. 62/534,672, filed Jul. 19, 2017. The entire contents of the above-identified applications are hereby fully incorporated herein by reference.

STATEMENT REGARDING FEDERALLY SPONSORED RESEARCH

This invention was made with government support under grant number CA197568 awarded by the National Institutes of Health. The government has certain rights in the invention.

TECHNICAL FIELD

The subject matter disclosed herein is generally directed to methods for diagnosing and treating cancers in a subject. More specifically, the disclosure relates to methods of inhibiting bacterial growth for treating neoplasms in a subject, or to methods of diagnosing whether a patient has a bacterial infection in or associated with the neoplasm.

BACKGROUND

Cancers, like other diseased or healthy tissues, are comprised of a subject's own cells encoded by their own genomes, together with a diverse population of associated microorganisms (the microbiota). The microbiota and host form a complex "super-organism" in which symbiotic relationships confer benefits necessary for human health in addition to pathogenic consequences. Recent studies have demonstrated that perturbations in the composition of the human microbiota, or dysbiosis, can significantly increase the risk of specific cancer types, especially colorectal cancer (CRC). The human colon is the anatomical location with the largest number of microbes; a growing body of evidence demonstrates the role of particular microorganisms in modulating inflammatory environments and promoting tumor growth and metastasis.

For example, *Fusobacterium* is a genus of obligate anaerobic, Gram-negative bacteria that usually colonize in the oral cavity of nearly all humans, some strains of *Fusobacterium* contribute to the development of dental plaques and periodontal disease. These bacteria are poor colonizers of healthy colon mucosa and cannot breach the intact colon wall. However, when an inflammation, adenoma or carcinoma develops, the deteriorated microenvironment of the colon wall may allow these microorganisms including *Fusobacterium, Peptostreptococcus*, and *Lactococcus* to access and adhere the basement membrane. One of reasons may be the formation of local anaerobic microenvironment induced by aerobic bacteria such as *Pseudomonas*, which is suitable for these potential pathogens to colonize. Different from *Fusobacterium*, however, *Lactococcus*, which produce a single product-lactic acid, plays a probiotic role in colon. It is not yet clear whether these bacterial passengers merely benefit from the CRC microenvironment or they also play an active part in disease progression.

Many cancers are known to be caused by infection, such as cervical cancer (caused by human papillomavirus), hepatocellular cancer (caused by hepatitis B virus) and Burkitt's lymphoma (caused by the Epstein-Barr virus). Similarly, some auto-immune diseases are caused by infection, such as rheumatic heart valvular disease caused by a streptococcal infection and gastritis and gastric ulcers, caused by a *Helicobacter pylori* infection. Many other chronic diseases (such as cancers, inflammatory diseases and autoimmune diseases) are suspected to be caused by pathogens, yet the specific microbe, if any, is unknown.

Computational subtraction methods for pathogen discovery are contemplated for pathogen discovery. The principle behind sequence-based computation subtraction is that the human genome sequence is nearly complete and that infected tissues contain human and microbial RNA and DNA. The method entails generating and sequencing libraries from human tissue and computational subtraction of normal human sequences, wherein the remainder sequences are of non-human origin, thereby allowing disease-specific sequences to be validated experimentally. (see, e.g., Weber, Shendure et al., Nature Genetics, 2002 and Sorek & Safer, Nucleic Acids Research, 2003). Improved genome sequencing technology facilitates pathogen discovery especially since the cost per genome has dropped significantly since 2007 (see, e.g., genome.gov/sequencingcosts).

Another software for identifying or discovering microbes by deep sequencing of human tissue is PathSeq, which also includes a microbial classification module (see, e.g., Kostic et al., Nature Biotechnology, 2011). PathSeq has been utilized in pathogen analysis of colorectal cancer/normal genome pairs (see, e.g., Bass et al., Nature Genetics, 2011 and Kostic et al., Genome Research, 2012). The initial analysis identified tumor-enrichment of *Fusobacterium* and *Streptococcaceae* in colorectal cancer. The analytic method involved counts of bacterial reads from whole genome DNA sequence data from 9 cases and testing with LEfSe (Segata et al., 2012); linear discriminant analysis (LDA) coupled with effect size measurements, comparing tumor and normal cells. The analysis of 95 cases with 16S PCR data showed enrichment only of Fusobacteria (see, e.g., Kostic et al., Genome Research, 2012 and Castellarin et al., Genome Research, 2012, using RNA sequencing).

Characteristics of *Fusobacterium* species are as follows. It is a Gram (-) filamentous, anaerobic bacteria, classed as a human pathogen (i.e. a disease causing bacteria), present in the oral cavity and plays a role in periodontal disease and not a common component of the lower gastrointestinal tract (human microbiome project). There is modest promotion of intestinal tumorigenesis by *Fusobacterium* in an Apc(Min) model (see, e.g., Kostic et al., Cell Host & Microbe, 2013). *Fusobacterium* is associated with an inflammatory signature in colon cancer (see, e.g., Kostic et al., Cell Host & Microbe, 2013).

Citation or identification of any document in this application is not an admission that such document is available as prior art to the present invention.

SUMMARY

The continued association of *Fusobacterium* species with human tumors indicates it is a critical component of the tumor microenvironment. This observation extends beyond *Fusobacterium* to include a range of co-occurring gram-negative anaerobes such as *B. fragilis* and *S. sputigena*. *Fusobacterium*-associated colorectal cancers exhibit a distinct microbial signature that is maintained through metastasis and multiple serial passages of xenografts in mice. Antibiotics targeting *Fusobacterium* can retard the growth of *Fusobacterium*-enriched xenografts, demonstrating a key role for *Fusobacterium* infection in the proliferation of colorectal cancer and providing new opportunities for therapeutic intervention.

Accordingly, the invention provides a method of treating a neoplasm in a subject comprising administering to the subject an agent, compound, or composition that inhibits bacterial growth in the subject. In certain embodiments, the invention further includes diagnosing whether the subject has a bacterial infection.

According to the invention, a bacterial infection associated with a neoplasm, advantageously a bacterial infection comprising a gram negative bacteria is diagnosed. In certain embodiments, the gram negative bacteria is an *Fusobacterium*. *Fusobacterium* is often found accompanied by other bacteria, often anaerobic bacteria including but not limited to one or more of *Selenomonas, Bacteroides*, and *Prevotella* genera. When diagnosed, the infection is advantageously treated for example with an antibiotic, preferably with an antibiotic selective for the one or more organisms identified.

The invention is advantageously applied for any neoplasm, tumor, cancer and the like with which the gram negative bacterium, e.g., the *Fusobacterium*, is associated, which can be, without limitation, a gastrointestinal cancer such as a colon cancer, or a metastatic tumor. The infecting bacteria, often having originated from the gut and transported to the location of the neoplasm, can be associated with any neoplasm, tumor, or cancer type, regardless of location. Likewise, neoplasm, tumor or cancer can be metastatic, without regard to the location or tumor type from which it originated.

The bacterial infection can be detected and identified by any convenient method, and can involve, without limitation, directly detecting and identifying the bacteria or by detecting and identifying any bacterial component. For example, the bacteria or component thereof can be identified in a tumor biopsy, in a stool sample, in circulating in plasma, and the like. Advantageously, the bacteria can be identified in nucleic acids samples from the subject. In preferred embodiments, detection and identification of nucleic acid components is sensitive and rapid, using for example, CRISPR based identification methods.

In embodiments of the invention, agent, compound, or composition comprises an antibiotic effective against the identified bacteria. Preferably, the agent is selective for the bacteria. For example, in an embodiment of the invention, the bacteria is a *Fusobacterium* and the antibiotic or antibacterial agent selectively targets the *Fusobacterium*. *Fusobacterium* is often found accompanied by other bacteria, often anaerobic bacteria including but not limited to one or more of *Selenomonas, Bacteroides*, and *Prevotella* genera. In certain embodiments, the agent, compound, or composition can target such bacteria instead of or in addition to *Fusobacterium*. In certain embodiments, when the identified bacteria is *Fusobacterium* the selective agent comprises metronidazole or 5-fluorouracil. In an embodiment of the invention, the treatment method can comprise diet modification. In a non-limiting example, a subject is assigned or prescribed a diet low in fat, low in lipid content, and or low in carbohydrates. According to the invention, the method can comprise coadministration of the antibacterial agent with any suitable antineoplastic treatment.

In another aspect, the invention provides a method of identifying a cellular component or pathway linked to sensitivity to growth induction by a *Fusobacterium*, which comprises contacting a test cell which comprises a mutation or phenotype linked to the cellular component or pathway with a *Fusobacterium*, contacting a control cell with the *Fusobacterium*, and identifying the cellular component or pathway as linked to sensitivity to induction by *Fusobacterium* if the test cell and control cell display a *Fusobacterium*-dependent phenotypic change. In certain embodiments, the method comprises comparing a library of test cells to a control cell. Further, the test cell or library can be from any neoplasm-related cell, including but not limited to a tumor cell, a transformed cell, or a model cell, and can be an experimental cell line or a cell from a patient tumor.

In an aspect of the invention, there is provided a method of identifying a compound or composition that inhibits induction of a bacterial cell associated with a tumor, for example, *Fusobacterium*, which comprises culturing a mammalian cell with a *Fusobacterium* in the presence of a test compound, culturing the mammalian cell with a *Fusobacterium* in the absence of the test compound, and identifying the compound as an induction inhibitor if the test compound inhibits growth of the test culture. The mammalian cell can be a tumor cell, a transformed cell, or a model cell, and can be an experimental cell line or a cell from a subject tumor.

In an aspect, there is provided a method of identifying a subpopulation of a population of patients having a neoplasm comprising diagnosing and identifying therefrom patients in the population having a bacterial infection in or associated with the neoplasm, whereby those patients having the bacterial infection in or associated with the neoplasm are the subpopulation. The bacterial infection can comprise a gram negative bacterial infection, including but not limited to a *Fusobacterium* infection. In certain embodiments, the bacterial infection is in or associated with gastrointestinal cancer or metastatic tumor or is in a stool sample. Further, the invention improves therapy by distinguishing patients having certain bacterial infections in or associated with their neoplasm or tumor from and able to benefit from such treatment from those that do not. Accordingly, the invention identifies subjects that might not benefit from the antibacterial treatment and avoids administration of potentially dangerous and or toxic agents and compounds to subjects that would not benefit. For example, whereas 5-fluorouracil is identified for treatment of subjects having *Fusobacterium* in or associated with neoplasm, the invention avoids administration of 5-fluorouracil in the absence of such bacteria. 5-fluorouracil has been associated with cardiotoxicity during chemotherapy for adenocarcinoma of the small bowel.

In an aspect of the invention, there is provided a method of identifying a treatment regimen for a patient having a neoplasm comprising diagnosing whether the patient has a bacterial infection in or associated with the neoplasm. In an embodiment of the invention, the infection comprises a gram negative bacterial infection, including but not limited to a *Fusobacterium* infection. *Fusobacterium* is often found accompanied by other bacteria, often anaerobic bacteria including but not limited to one or more of *Selenomonas, Bacteroides*, and *Prevotella* genera. In certain embodiments, such bacteria can be diagnosed instead of or in addition to *Fusobacterium*. The bacterial infection can be associated with a gastrointestinal cancer or metastatic tumor or identified in a stool sample. The method can additionally include administering an agent, compound or composition that inhibits bacterial growth in the subject, optionally wherein the agent, compound or composition is specific to the bacterial infection, and further optionally on a regimen comprising coincident with or sequentially to administration of anti-neoplastic agents.

The invention also provides a method for removal of a tumor in a subject comprising systemically and/or locally to the tumor testing for the presence of a bacterial infection, optionally wherein the testing comprises a rapid diagnostic that identifies an RNA and/or DNA signature of a bacterial, and further optionally wherein the testing includes measuring bacterial load. In an embodiment of the invention, the bacterial infection comprises a gram negative bacterial infection, including but not limited to a *Fusobacterium* infection. *Fusobacterium* is often found accompanied by other bacteria, often anaerobic bacteria including but not limited to one or more of *Selenomonas, Bacteroides*, and *Prevotella* genera. In certain embodiments, such bacteria can be diagnosed instead of or in addition to *Fusobacterium*. The bacterial infection can be in or associate with, without limitation a gastrointestinal cancer or metastatic tumor or is in a stool sample. In certain embodiments, the method additionally includes administering an agent, compound or composition that inhibits bacterial growth in the subject. The administering can be locally to the area of the patient from which the tumor has been or is being removed, and/or can be systemic.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1A: Pie charts represent the overall *Fusobacterium* qPCR status of matched primary colorectal cancers and liver metastases from 101 patients. The two-by-two table represent the number of primary-metastasis pairs (individual patients) that were *Fusobacterium* qPCR positive (dark grey) or negative (light grey). FIG. 1B: Schematic of *Fusobacterium* culture and *Fusobacterium* targeted qPCR status of paired snap frozen colorectal primary tumors and liver metastases from eleven patients (P1 to P11). FIG. 1C: Species level microbial composition of paired colorectal primary (CP) tumors and liver metastases (LM) tumors, assayed by RNA sequencing followed by PathSeq analysis for microbial identification. For simplicity only organisms with >2% relative abundance (RA) in at least one tumor are shown. The colors correspond to bacterial taxonomic class, red: Fusobacteriia, pink: Negativicutes, blue/green: Bacteroidia, orange: Clostridia, yellow: Gamma-proteobacteria, dark brown: Spirochaetes. P=patient. The samples are separated into three groups: *Fusobacterium*-positive primary tumor and metastases (n=6 pairs), *Fusobacterium*-positive primary tumor and *Fusobacterium*-negative metastases (n=2 pairs), *Fusobacterium*-negative primary tumor and metastases (n=2 pairs). Patient 7 (P7) had insufficient tissue for RNA sequencing analysis. FIG. 1D: Box plots represent the Jaccard Index (proportion of shared genera/species) between paired colorectal primary (CP) tumors and liver metastases (LM) at both the genus and species level at 1% RA. The box represents the first and third quartiles, and error bars indicate 95% confidence of the median. Paired samples that were *Fusobacterium*-positive in both the primary tumor and metastasis are compared to paired samples where the metastasis was *Fusobacterium*-negative. P values were determined using Welch Two Sample t-test. FIG. 1E: Box plots of Fusobacteria relative abundance in primary COAD (n=435) and primary LIHC (n=201) from TCGA and primary-metastasis pairs from ten patients. The box represents the first and third quartiles, and error bars indicate 95% confidence of the median. P values were determined using Welch Two Sample t-test with correction for unequal variances. FIG. 1F: Identification of bacteria that co-occur with *Fusobacterium* in primary COAD. Primary COAD tumors were subset into two groups, *Fusobacterium* "High" if they had a *Fusobacterium* RA>1% (n=110, median RA=5.72%, mean RA=7.7%) and *Fusobacterium* "Low/Neg" if they had a RA<1% (n=325, median RA=0.06%, mean RA=0.16%). The bar plot demonstrates genera enriched (red) and depleted (green) in COAD with >1% *Fusobacterium* RA. The cladogram lists the respective bacterial phyla and class.

FIGS. 2A-2H: *F. nucleatum* RNA in situ hybridization analysis of matched primary colorectal tumors and liver metastases. Representative images of *F. nucleatum* spatial distribution in paired samples from patient 187 (P187) primary colorectal tumor (FIG. 2A and FIG. 2B) and liver metastasis (FIG. 2E and FIG. 2F), and patient 188 (P188) primary colorectal tumor (FIG. 2C and FIG. 2D) and liver metastasis (FIG. 2G and FIG. 2H) from the "FFPE paired cohort" are shown. Arrows indicate cells whose histomorphology is consistent with colon cancer cells infected by invasive *F. nucleatum* (red dots) in both primary colorectal tumors (FIG. 2B and FIG. 2D) and matched liver metastases (FIG. 2F and FIG. 2H). *Fusobacterium* containing biofilm (bf) is highlighted in the colorectal tumor of patient 187 (FIG. 2A). *Fusobacterium* was not detected in normal liver (nl) tissue (FIG. 2E, FIG. 2F). Stroma; s. Magnification, (FIG. 2A, FIG. 2C, FIG. 2E and FIG. 2G), inset magnification, (FIG. 2B, FIG. 2D, FIG. 2F and FIG. 2H). The black boxes represent areas of the images selected for the corresponding inset magnification image. Scale bars are included at the bottom left of each image.

FIG. 3A: The box plots demonstrate PDX engraftment success rate in relation to *Fusobacterium* culture or qPCR status. P values were determined using the z score test for two population proportions. FIG. 3B: Assessment of *Fusobacterium* persistence in PDX COCA36 over the period of 204 days. *Fusobacterium* persistence was determined via microbial culture and *Fusobacterium*-targeted qPCR. *Note that there are no negative timepoints. FIG. 3C: Species level microbial composition of three patient primary colon adenocarcinomas (COCA36, COCA39 and COCA6) and subsequent PDX's. Unbiased RNA sequencing, followed by PathSeq analysis for microbial identification. For simplicity selected species with >1% relative abundance in the primary tumor and either correspond PDX are show. The colors correspond to bacterial taxonomic class, red: Fusobacteriia, pink: Negativicutes, blue/green: Bacteroidia, orange: Clostridia.

FIGS. 4A-4D: Primary colon cancer and derived xenograft *F. nucleatum* isolates are invasive. FIG. 4A: Transmission electron microscopy (TEM) of primary colon cancer *F. nucleatum* isolate (Fn-COCA36P-01) adhering to and invading HT-29 colon cancer cells. Black arrows demonstrate the presence of *F. nucleatum* cells. Cyto=cytoplasm, Nucl=nucleus. FIG. 4B: TEM of PDX *F. nucleatum* isolate (Fn-COCA36F3-01) adhering to and invading HCT-116 colon cancer cells. FIG. 4C: TEM of PDX *F. nucleatum* isolate (Fn-COCA36F3-01) adhering to and invading HT-29 colon cancer cells. FIG. 4D: TEM of patient derived xenograft (COCA36). Black arrows demonstrate the presence of bacterial cells adhering to and invading the PDX cells.

FIG. 5A: Percentage tumor volume increase of *Fusobacterium*-free xenograft derived from HT-29 cells treated with metronidazole (treated) or with vehicle (untreated). P values, determined using a Welch's Two Sample t-test, were not statistically significant between the two conditions, at any of the tested timepoints (p>0.05). Tumors were measured in a blinded fashion on Mondays, Wednesdays and Fridays each week. Error bars represent the mean+/−SEM. FIG. 5B: Percentage tumor volume increase in *Fusobacterium*-positive PDX tumors (COCA36) treated with metronidazole (treated) or with vehicle (untreated). P values were determined using the Welch's Two Sample t-test (* p<0.05, ** p<0.01). Tumor volumes were measured as in FIG. 5A. FIG. 5C: Assessment of *Fusobacterium* tissue load. *Fusobacterium*-targeted qPCR on PDX tissue (COCA36) following treatment with metronidazole (treated) or with vehicle (untreated). ND=not detected. The center bar represents the mean and the error bars are the standard error of the mean (SEM). P values were determined using Welch Two Sample t-test. FIG. 5D: BrdU immunohistochemistry of PDX tumors to assess cell proliferation. The 40× images represent BrdU staining (brown) of PDXs following treatment with metronidazole (treated) or with vehicle (untreated). The bar plot represents the percentage of cells with BrdU incorporation in treated and untreated PDXs (n=6 per arm); error bars represent the mean+/−the SEM. The p values were determined using the Welch Two Sample t-test.

FIG. 6A: Whole genome sequencing and average nucleotide identity (ANI) analysis reveal identical an identical strain of *F. necrophorum* in both the colorectal primary and liver metastasis of patient 1 (P1) despite these tumors being collected two years apart. FIG. 6B: Whole genome sequencing and average nucleotide identity (ANI) analysis reveal identical an identical strain of *F. nucleatum* in both the colorectal primary and liver metastasis of patient 2 (P2) despite these tumors being collected three months apart.

FIG. 9A: Genus level (OTU_L7) microbial composition of paired colorectal primary (CP) tumors and liver metastases (LM) tumors from eleven patients (P1 to P11), assayed by bacterial 16S rRNA gene sequencing. For simplicity only organisms with >2% relative abundance (RA) in at least one tumor are shown. The samples are separated into three groups: *Fusobacterium*-positive (>1% RA) primary tumor and metastases (n=7 pairs), *Fusobacterium*-positive primary tumor and *Fusobacterium*-negative (<1% RA) metastases (n=1 pair), *Fusobacterium*-negative primary tumor and metastases (n=3 pairs). FIG. 9B: The box-plot represent the Jaccard Index (proportion of shared genera) between paired colorectal primary (CP) tumors and liver metastases (LM) at 1% RA. The box represents the first and third quartiles, and error bars indicate 95% confidence of the median. Paired samples that were *Fusobacterium*-positive in both the primary tumor and metastasis are compared to paired samples where the metastasis was *Fusobacterium*-negative. The p-values were determined using Welch Two Sample t-test. FIG. 9C: Linear regression analysis of *Fusobacterium* RA (%) in paired primary colorectal tumors and liver metastasis from eleven patients (P1 to P11). The point for P9, P10 and P11 are overlap on the x and y axes.

FIG. 10A: Pie charts represent the overall *Fusobacterium* qPCR status of matched primary colorectal cancers and liver metastases from 101 patients from the "FFPE paired cohort". The two-by-two table represents the number of primary-metastasis pairs (individual patients) that were *Fusobacterium* qPCR positive (dark grey) or negative (light grey). FIG. 10B: The heat-map demonstrates *Fusobacterium* status across the colon and rectum of 101 colorectal adenocarcinoma tumors with liver metastasis from the "FFPE paired cohort". The 101 patients are divided into three groups: those that were *Fusobacterium* qPCR positive in the colorectal primary (CP) and liver metastasis (LM) n=20, those that were *Fusobacterium* qPCR positive in the CP and *Fusobacterium* qPCR negative in the LM n=24, and those that were *Fusobacterium* qPCR negative in the CP and LM n=57. Color scale represents the percentage of tumors from different regions of the colon, within each group. P values in the adjacent table were determined using the z score test for two population proportions (two-tailed), comparing the *Fusobacterium* CP-LM double positive tumors (n=20) to the *Fusobacterium* CP-LM double negative tumors. FIG. 10C: Kaplan Meier curves of patient overall survival from TCGA colon adenocarcinomas ("TCGA cohort", n=405/430 with survival data) based upon tumor location (cecum/ascending vs. non-cecum ascending) and FIG. 10D: *F. nucleatum* load (determined by PathSeq analysis) in cecum/ascending colon adenocarcinomas. RA=relative abundance. P values were determined by the Log-rank Mantel-Cox test. *Fusobacterium* "High"=*Fusobacterium*>1% relative abundance.

FIGS. 11A-11B: Analysis of tumor grade from "xenograft cohort" (FIG. 11A) Fischer's exact test for patient derived xenograft (PDX) success and tumor grade (FIG. 11B) Fischer's exact test for *Fusobacterium* culture and tumor grade

FIG. 13A: *F. nucleatum* was not detected in non-infected HCT116 cells, multiplicity of infection (MOI) of bacteria to eukaryotic cells 0:1, (FIG. 13B-FIG. 13D) Increasing *F. nucleatum* signals (red dots) were associated with increasing doses of *F. nucleatum* in cell lines. FIG. 13B: MOI bacteria to eukaryotic cells 1:1, FIG. 13C: MOI bacteria to eukaryotic cells 10:1, FIG. 13D: MOI bacteria to eukaryotic cells, 100:1

FIG. 14: Antibiotic sensitivity testing (E-test) of clinical *F. nucleatum* isolates. E-test on *F. nucleatum* strains isolated from COCA36 primary tumor and derived xenografts. All E-tests were carried out in triplicate on both FAA agar. The antibiotics tested were metronidazole (MZ), cefoxitin (FX) and imipenem (IP). All *F. nucleatum* strains tested were sensitive to cefoxitin and metronidazole in vitro: test range was 0.016 to 256 ug/ml. No bacterial growth at 0.016 ug/ml, MIC<0.016 ug/ml. The *F. nucleatum* strains tested were resistant/hetero-resistant to imipenem in vitro.

FIG. 20 illustrates a comparison between tumors treated with 5-FU or a 5-FU prodrug (right panel) and tumors with no treatment (left panel). A total of 91 patient colorectal adenocarcinoma tumors with recurrence data were analyzed by *Fusobacterium* culture and bacterial 16s rRNA sequencing. As shown, *Fusobacterium*-positive colorectal tumors treated with 5-FU or a 5-FU prodrug are less likely to develop recurrence/metastasis. * indicates *Fusobacterium*-culture positive and/or *Fusobacterium*>1% relative abundance (microbiome analysis).

DETAILED DESCRIPTION OF THE EXAMPLE EMBODIMENTS

General Definitions

Figure 1A:
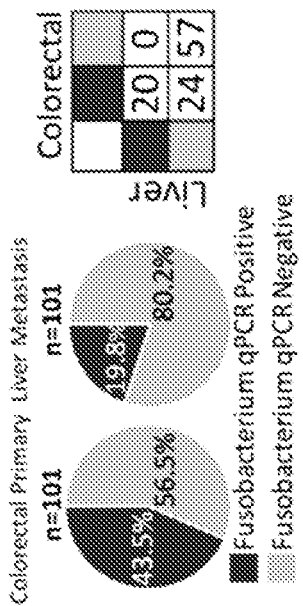
FIGS. 1A-1F: *Fusobacterium* colonizes liver metastases of *Fusobacterium*-associated colorectal primary tumors.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^6$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Associations between different bacteria and various tumors have been reported, and growth of bacteria specifically within tumos following deliberate systemic administration has been demonstrated for numerous bacterial species at preclinical and clinical levels. In some cases, such bacteria are thought to be causative agents of malignancy, but in other cases, bacteria within tumors may arise from spontaneous infection.

The invention provides a method of treating a neoplasm in a subject comprising administering to the subject an agent, compound, or composition that inhibits bacterial growth in the subject. In certain embodiments, the invention further includes diagnosing whether the subject has a bacterial infection.

According to the invention, a bacterial infection associated with a neoplasm, advantageously a bacterial infection comprising a gram negative bacteria is diagnosed. In certain embodiments, the gram negative bacteria is an *Fusobacterium*. *Fusobacterium* is often found accompanied by other bacteria, often anaerobic bacteria including but not limited to one or more of *Selenomonas, Bacteroides*, and *Prevotella* genera. When diagnosed, the infection is advantageously treated for example with an antibiotic, preferably with an antibiotic selective for the one or more organisms identified.

The invention is advantageously applied for any neoplasm, tumor, cancer and the like with which the gram negative bacterium, e.g., the *Fusobacterium*, is associated, which can be, without limitation, a gastrointestinal cancer such as a colon cancer, or a metastatic tumor. The infecting bacteria, often having originated from the gut and transported to the location of the neoplasm, can be associated with any neoplasm, tumor, or cancer type, regardless of location. Likewise, neoplasm, tumor or cancer can be metastatic, without regard to the location or tumor type from which it originated.

The bacterial infection can be detected and identified by any convenient method, and can involve, without limitation, directly detecting and identifying the bacteria or by detecting and identifying any bacterial component. For example, the bacteria or component thereof can be identified in a tumor biopsy, in a stool sample, in circulating in plasma, and the like. Advantageously, the bacteria can be identified in nucleic acids samples from the subject. In preferred embodiments, detection and identification of nucleic acid components is sensitive and rapid, using for example, CRISPR based identification methods.

In embodiments of the invention, agent, compound, or composition comprises an antibiotic effective against the identified bacteria. Preferably, the agent is selective for the bacteria. For example, in an embodiment of the invention, the bacteria is a *Fusobacterium* and the antibiotic or antibacterial agent selectively targets the *Fusobacterium*. *Fusobacterium* is often found accompanied by other bacteria, often anaerobic bacteria including but not limited to one or more of *Selenomonas, Bacteroides*, and *Prevotella* genera. In certain embodiments, the agent, compound, or composition can target such bacteria instead of or in addition to *Fusobacterium*. In certain embodiments, when the identified bacteria is *Fusobacterium* the selective agent comprises metronidazole or 5-fluorouracil. In an embodiment of the invention, the treatment method can comprise diet modification. In a non-limiting example, a subject is assigned or prescribed a diet low in fat, low in lipid content, and or low in carbohydrates. According to the invention, the method can comprise coadministration of the antibacterial agent with any suitable antineoplastic treatment.

In another aspect, the invention provides a method of identifying a cellular component or pathway linked to sensitivity to growth induction by a *Fusobacterium*, which comprises contacting a test cell which comprises a mutation or phenotype linked to the cellular component or pathway with a *Fusobacterium*, contacting a control cell with the *Fusobacterium*, and identifying the cellular component or pathway as linked to sensitivity to induction by *Fusobacterium* if the test cell and control cell display a *Fusobacterium*-dependent phenotypic change. In certain embodiments, the method comprises comparing a library of test cells to a control cell. Further, the test cell or library can be from any neoplasm-related cell, including but not limited to a tumor cell, a transformed cell, or a model cell, and can be an experimental cell line or a cell from a patient tumor.

In an aspect of the invention, there is provided a method of identifying a compound or composition that inhibits induction of a bacterial cell associated with a tumor, for example, *Fusobacterium*, which comprises culturing a mammalian cell with a *Fusobacterium* in the presence of a test compound, culturing the mammalian cell with a *Fusobacterium* in the absence of the test compound, and identifying the compound as an induction inhibitor if the test compound inhibits growth of the test culture. The mammalian cell can be a tumor cell, a transformed cell, or a model cell, and can be an experimental cell line or a cell from a subject tumor.

In an aspect, there is provided a method of identifying a subpopulation of a population of patients having a neoplasm comprising diagnosing and identifying therefrom patients in the population having a bacterial infection in or associated with the neoplasm, whereby those patients having the bacterial infection in or associated with the neoplasm are the subpopulation. The bacterial infection can comprise a gram negative bacterial infection, including but not limited to a *Fusobacterium* infection. In certain embodiments, the bacterial infection is in or associated with gastrointestinal cancer or metastatic tumor or is in a stool sample.

In an aspect of the invention, there is provided a method of identifying a treatment regimen for a patient having a neoplasm comprising diagnosing whether the patient has a bacterial infection in or associated with the neoplasm. In an embodiment of the invention, the infection comprises a gram negative bacterial infection, including but not limited to a *Fusobacterium* infection. *Fusobacterium* is often found accompanied by other bacteria, often anaerobic bacteria including but not limited to one or more of *Selenomonas, Bacteroides*, and *Prevotella* genera. In certain embodiments, such bacteria can be diagnosed instead of or in addition to *Fusobacterium*. The bacterial infection can be associated with a gastrointestinal cancer or metastatic tumor or identified in a stool sample. The method can additionally include administering an agent, compound or composition that inhibits bacterial growth in the subject, optionally wherein the agent, compound or composition is specific to the bacterial infection, and further optionally on a regimen comprising coincident with or sequentially to administration of anti-neoplastic agents.

The invention also provides a method for removal of a tumor in a subject comprising systemically and/or locally to the tumor testing for the presence of a bacterial infection, optionally wherein the testing comprises a rapid diagnostic that identifies an RNA and/or DNA signature of a bacterial, and further optionally wherein the testing includes measuring bacterial load. In an embodiment of the invention, the bacterial infection comprises a gram negative bacterial infection, including but not limited to a *Fusobacterium* infection. *Fusobacterium* is often found accompanied by other bacteria, often anaerobic bacteria including but not limited to one or more of *Selenomonas, Bacteroides*, and *Prevotella* genera. In certain embodiments, such bacteria can be diagnosed instead of or in addition to *Fusobacterium*. The bacterial infection can be in or associate with, without limitation a gastrointestinal cancer or metastatic tumor or is in a stool sample. In certain embodiments, the method additionally includes administering an agent, compound or composition that inhibits bacterial growth in the subject. The administering can be locally to the area of the patient from which the tumor has been or is being removed, and/or can be systemic.

Fusobacterium and Detection

*Fusobacterium* organisms are anaerobic, non-motile, gram-negative bacilli and include *F. necrophorum, F. nucleatum, F. mortiferu, F. varium, F. gonidaformans, F. alocis, F. pseudonecrophorum, F. salci*, and *F. ulcerans*. Microscopically, they are characterized by slender or fusiform rods with tapered ends, though some species may be pleomorphic. *Fusobacterium* is included in the genera of anaerobic, gram-negative, non-spore-forming bacteria, which include *Bacteroides, Prevotella*, and *Porphyromonas*. *Fusobacterium* can be differentiated from these other gram-negative, obligate anaerobes by its ability to produce significant amounts of butyric acid from glucose, giving cultured colonies a characteristic odor. Identification in the laboratory is made by morphology and the following biochemical assays:

Identification of *F. necrophorum* Species:

| | |
|---|---|
| Indole | Positive |
| Lipase | Positive |
| Hydrogen sulfide | Negative |
| Catalase | Negative |
| Esculin | Negative |
| Catalase | Negative |

*Fusobacterium* species are normal inhabitants of all mucosal surfaces, including the mouth, upper respiratory tract, gastrointestinal tract, and urogenital tract. Worldwide, *F. nucleatum* is the most common *Fusobacterium* species found in clinical infections, while *F. necrophorum* is the most virulent. The species is generally susceptible to penicillin, clindamycin, and chloramphenicol and resistant to erythromycin and macrolides.

Though part of the normal flora of human tissues, *Fusobacterium* can invade tissues after surgical or accidental trauma, edema, anoxia, and/or tissue destruction. *F. necrophorum* contains particularly powerful endotoxic lipopolysaccharides in its cell wall and produces a coagulase enzyme that encourages clot formation. Additionally, it produces a variety of exotoxins, including leukocidin, hemolysin, lipase, and cytoplasmic toxin, all of which likely contribute to its pathogenicity.

Antibiotics and Dosing

Anti-gram negative, and gram-negative antibiotic are used interchangeably to refer to antibiotic active agents (and formulations comprising such active agents) which have effectiveness against gram negative bacteria.

As an overview, in one or more embodiments, an aqueous composition comprises anti-gram-negative antibiotic or salt thereof being present at an amount ranging from about 100 mg/ml to about 200 mg/ml.

In one or more embodiments, an aqueous composition comprises an antibiotic or salt thereof being present at a concentration ranging from about 0.6 to about 0.9 of the water solubility limit, at 25 C and 1.0 atmosphere, of the antibiotic or salt thereof.

In one or more embodiments, a unit dose comprises a container and an aqueous composition, comprising an anti-gram-negative antibiotic or salt thereof at a concentration ranging from about 100 mg/ml to about 200 mg/ml.

In one or more embodiments, a unit dose comprises a container and a powder comprising an antibiotic or salt thereof, wherein the powder is present in an amount ranging from about 550 mg to about 900 mg.

In one or more embodiments, a unit dose comprises a container; and a powder comprising an antibiotic or salt thereof, wherein the powder is present in an amount ranging from about 150 mg to about 450 mg.

In one or more embodiments, a method of administering an antibiotic formulation to a patient in need thereof comprises aerosolizing an antibiotic formulation to administer the antibiotic formulation to the pulmonary system of the patient. The antibiotic formulation has a concentration of anti-gram-negative antibiotic or salt thereof ranging from about 100 mg/ml to about 200 mg/ml.

In one or more embodiments, a method of administering an antibiotic formulation to a patient in need thereof comprises inserting a tube into a trachea of a patient. The method also comprises aerosolizing an antibiotic formulation to administer the antibiotic formulation to the pulmonary system of the patient. The antibiotic formulation consists essentially of an anti-gram-negative antibiotic or salt thereof and water.

In one or more embodiments, a method of administering an antibiotic formulation to a patient in need thereof comprises aerosolizing an antibiotic formulation to administer the antibiotic formulation to the pulmonary system of the patient. The antibiotic formulation has a concentration of anti-gram-negative antibiotic or salt thereof ranging from about 100 mg/ml to about 200 mg/ml.

In one or more embodiments, a method of administering an antibiotic formulation to a patient in need thereof comprises inserting a tube into a trachea of a patient. The method also comprises aerosolizing an antibiotic formulation to administer the antibiotic formulation to the pulmonary system of the patient The antibiotic formulation consists essentially of an anti-gram-negative antibiotic or salt thereof and water.

The concentration of the antibiotic, corrected for potency, in one or more embodiments, may range from about 40 mg/ml to about 200 mg/ml, such as about 60 mg/ml to about 140 mg/ml, or about 80 mg/ml to about 120 mg/ml. For example, in the case of anti-gram-negative antibiotics or salts thereof, the concentration as corrected for potency may range from about 40 mg/ml to about 200 mg/ml, such as from about 90 mg/ml to about 200 mg/ml, about 110 mg/ml to about 150 mg/ml, or about 120 mg/ml to about 140 mg/ml.

The aqueous compositions typically have a pH that is compatible with physiological administration, such as pulmonary administration. For example, the aqueous composition may have a pH ranging from about 3 to about 7, such as about 4 to about 6.

In addition, the aqueous compositions typically have an osmolality that is compatible with physiological administration, such as pulmonary administration. In one or more embodiments, the aqueous composition may have an osmolality ranging from about 90 mOsmol/kg to about 500 mOsmol/kg, such as 120 mOsmol/kg to about 500 mOsmol/kg, or about 150 mOsmol/kg to about 300 mOsmol/kg.

In one or more embodiments, the aqueous compositions are stable. For instance, in some cases, no precipitate forms in the aqueous composition when the aqueous composition is stored for 1 year, or even 2 years, at 25 C.

The potency of the antibiotic or salt thereof may range from about 500 micrograms/mg to about 1100 .mu.g/mg. In one or more embodiments, the potency of anti-gram-negative antibiotics or salts thereof, such as gentamicin, typically ranges from about 500 micrograms/mg to about 1100 micrograms/mg, such as about 600 micrograms/mg to about 1000 micrograms/mg, or about 700 micrograms/mg to about 800 micrograms/mg.

The chromatographic purity level of the antibiotic or salt thereof typically greater than about 80%, such as greater than about 85%, greater than about 90%, or greater than about 95%. In this regard, there is generally no major impurity greater than about 10%, such as no greater than about 5% or no greater than about 2%. For instance, the amount of heavy metals is typically less than about 0.005 wt %, such as less than about 0.004 wt %, less than about 0.003 wt %, less than about 0.002 wt %, or less than about 0.001 wt %.

The amount of antibiotic or other active agent in the pharmaceutical formulation will be that amount necessary to deliver a therapeutically or prophylactically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1 wt % to about 99 wt %, such as from about 2 wt % to about 95 wt %, or from about 5 wt % to 85 wt %, of the active agent, and will also depend upon the relative amounts of additives contained in the composition. The compositions of the invention are particularly useful for active agents that are delivered in doses of from 0.001 mg/day to 100 mg/day, such as in doses from 0.01, mg/day to 75 mg/day, or in doses from 0.10 mg/day to 50 mg/day. It is to be understood that more than one active agent may be incorporated into the formulations described herein and that the use of the term "agent" in no way excludes the use of two or more such agents.

The pharmaceutical formulation may also comprise a buffer or a pH adjusting agent, typically a salt prepared from an organic acid or base. Representative buffers comprise organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, celluloses and derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-.beta.-cyclodextrin and sulfobutylether-.beta.-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polvsorbates such as "TWEEN 20" and "TWEEN 80"), sorbitan esters, lipids (for example phospholipids such as lecithin and other phosphatidyicholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", 19.sup.th ed., Williams & Williams, (1995), and in the "Physician's Desk Reference", 52nd ed., Medical Economics, Montvale, N.J. (1998), both of which are incorporated herein by reference in their entireties.

A skilled person can adjust dosing depending on factors taken into consideration by medical or veterinary practitioners, such as gender, age, general condition or overall health, weight, allergies to antibiotics or structurally similar compounds, and the like.

Nucleic Acid Detection and Diagnostics

Nucleic acids are a universal signature of biological information. The ability to rapidly detect nucleic acids with high sensitivity and single-base specificity provides a useful tool for diagnosis and monitoring of disease.

Rapid Diagnostics

Sensitive and rapid diagnostics provide real time detection and adjustment of therapeutic methods. For example, when a tumor is removed, diagnostics can be used to identify bacterial load of one or more bacteria, locally at the site where a tumor is identified and/or removed, as well as systemically. Further, such site directed and rapid diagnostics aid in the systemic and local administration of therapeutics, for example antibacterial agents, preferably antibacterial agents selective or specific to the content of a tumor identified and optionally removed. Likewise, if a target bacteria is not identified, broad based therapy would be adopted.

Bacteria

The following provides an example list of the types of microbes that might be detected using the embodiments disclosed herein. In certain example embodiments, the microbe is a bacterium. Examples of bacteria that can be detected in accordance with the disclosed methods include without limitation any one or more of (or any combination of) *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophila, Aeromonas veronii* biovar *sobria* (*Aeromonas sobria*), and *Aeromonas caviae*), *Anaplasma phagocytophilum, Anaplasma marginale Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis,* and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis,* and *Bordetella bronchiseptica*), *Borrelia* sp. (such as *Borrelia recurrentis,* and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium*), *Clostridium* sp. (such as *Clostridium perfringens, Clostridium difcile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli,* including opportunistic *Escherichia coli,* such as enterotoxigenic *E. coli,* enteroinvasive *E. coli,* enteropathogenic *E. coli,* enterohemorrhagic *E. coli,* enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Epidermophyton floccosum, Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Mannheimia hemolytica. Microsporum canis. Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium paratuberculosis Mycobacterium intracellulare, Mycobacterium avium, Mycobacterium bovis,* and *Mycobacterium marinum*), *Mycoplasm* sp. (such as *Mycoplasma pneumoniae, Mycoplasma hominis,* and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Pityrosporum orbiculare* (*Malassezia furfur*), *Plesiomonas shigelloides. Prevotella* sp., *Porphyromonas* sp., *Prevotella melaninogenica, Selenomonas* sp., *Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae,* spectinomycin-resistant serotype 6B *Streptococcus pneumoniae,* streptomycin-resistant serotype 9V *Streptococcus pneumoniae,* erythromycin-resistant serotype 14 *Streptococcus pneumoniae,* optochin-resistant serotype 14 *Streptococcus pneumoniae,* rifampicin-resistant serotype 18C *Streptococcus pneumoniae,* tetracycline-resistant serotype 19F *Streptococcus pneumoniae,* penicillin-resistant serotype 19F *Streptococcus pneumoniae,* and trimethoprim-resistant serotype 23F *Streptococcus pneumoniae,* chloramphenicol-resistant serotype 4 *Streptococcus pneumoniae,* spectinomycin-resistant serotype 6B *Streptococcus pneumoniae,* streptomycin-resistant serotype 9V *Streptococcus pneumoniae,* optochin-resistant serotype 14 *Streptococcus pneumoniae,* rifampicin-resistant serotype 18C *Streptococcus pneumoniae,* penicillin-resistant serotype 19F *Streptococcus pneumoniae,* or trimethoprim-resistant serotype 23F *Streptococcus pneumoniae*),

*Streptococcus agalactiae, Streptococcus mutans, Streptococcus pyogenes,* Group A streptococci, *Streptococcus pyogenes,* Group B streptococci, *Streptococcus agalactiae,* Group C streptococci, *Streptococcus anginosus, Streptococcus equismilis,* Group D streptococci, *Streptococcus bovis,* Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Trichophyton rubrum. T. mentagrophytes, Tropheryma whippelii, Ureaplasma urealyticum, Veillonella* sp., *Vibrio* sp. (such as *Vibrio cholerae, Vibrio parahemolyticus, Vibrio vulnficus, Vibrio parahaemolyticus, Vibrio vulnmficus, Vibrio alginolyticus, Vibrio mimicus, Vibrio hollisae, Vibrio fluvialis, Vibrio metchnikovii, Vibrio damsela* and *Vibrio furnisii), Yersinia* sp. (such as *Yersinia enterocolitica, Yersinia pestis,* and *Yersinia pseudotuberculosis*) and *Xanthomonas maltophilia* among others.

Nucleic Acid Detection Systems

Nucleic acid detection systems comprising CRISPR systems offer rapid and robust signal detection and offer the option to detect DNA or RNA. The CRISPR system effector protein can be an RNA-targeting effector protein or a DNA-targeting effector protein. Exemplary DNA-targeting effector proteins include, without limitation, Cas9 and Cpf1. Exemplary RNA-targeting proteins include, without limitation, Cas13b and C2c2 (now known as Cas13a). The effector protein can be from an organism of a genus selected from: *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter,* and *Lachnospira,* for example from an organism selected from *Leptotrichia shahii, Leptotrichia, wadei, Listeria seeligeri, Clostridium aminophilum, Camobacterium gallinarum, Paludibacter propionicigenes, Listeria weihenstephanensis, L. wadei* F0279 or *L. wadei* F0279 (Lw2) C2C2

In certain embodiments, the system may further comprise nucleic acid amplification reagents. An example of such a system is termed SHERLOCK (Specific High Sensitivity Enzymatic Reporter UnLOCKing) can rapidly detect DNA or RNA with attomolar sensitivity and single-base mismatch specificity. (Gootenberg et al., 2017, Nucleic acid detection with CRISPR-Cas13a/C2c2, Science 10.1126/science.aam9321).

SHERLOCK (coupled with reverse transcription as needed) achieves single molecule sensitivity for both RNA and DNA, as verified by digital-droplet PCR (ddPCR) and attomolar sensitivity can be attained in a single reaction, demonstrating the viability of this platform as a point-of-care (POC) diagnostic. SHERLOCK has similar levels of sensitivity as ddPCR and quantitative PCR (qPCR), two established sensitive nucleic acid detection approaches, whereas RPA alone was not sensitive enough to detect low levels of target. Moreover, SHERLOCK shows less variation than ddPCR, qPCR, and RPA, as measured by the coefficient of variation across replicates.

SHERLOCK is effective in infectious disease applications that require high sensitivity, including detecting viral particles down to 2 aM and discriminating between similar viruses such as between ZIKV and DENV. The method is also able to detect virus in clinical isolates (serum, urine, or saliva) where titers can be as low as $2 \times 10^3$ copies/mL (3.2 aM).

Another important application is the identification of bacterial pathogens and detection of specific bacterial genes. In a panel of five possible targeting crRNAs for different pathogenic strains and gDNA isolated from *E. coli* and *Pseudomonas aeruginosa,* SHERLOCK correctly genotyped strains and showed low cross-reactivity.

SHERLOCK can detect low frequency cancer mutations in cell free (cf) DNA fragments, which is challenging because of the high levels of wild-type DNA in patient blood For example, SHERLOCK can detect ssDNA 1 at attomolar concentrations diluted in a background of genomic DNA and can detect single nucleotide polymorphism (SNP)-containing alleles at levels as low as 0.1% of background DNA, which is in the clinically relevant range.

The nucleic acid amplification reagents may comprise a primer comprising an RNA polymerase promoter. In certain embodiments, sample nucleic acids are amplified to obtain a DNA template comprising an RNA polymerase promoter, whereby a target RNA molecule may be generated by transcription. The nucleic acid may be DNA and amplified by any method described herein. The nucleic acid may be RNA and amplified by a reverse transcription method as described herein. The aptamer sequence may be amplified upon unmasking of the primer binding site, whereby a trigger RNA is transcribed from the amplified DNA product. The target molecule may be a target DNA and the system may further comprises a primer that binds the target DNA and comprises a RNA polymerase promoter.

The systems feature one or more guide nucleic acids which are designed to bind to one or more target molecules that are diagnostic for a disease state. A disease state includes, without limitation, an infection, an organ disease, a blood disease, an immune system disease, a cancer, a brain and nervous system disease, an endocrine disease, a pregnancy or childbirth-related disease, an inherited disease, or an environmentally-acquired disease. In still further embodiments, the disease state is cancer or an autoimmune disease or an infection.

RNA sequencing (RNA-Seq) is a powerful tool for transcriptome profiling, but is hampered by sequence-dependent bias and inaccuracy at low copy numbers intrinsic to exponential PCR amplification. To mitigate these complications to allow truly digital RNA-Seq, a large set of barcode sequences is added in excess, and nearly every cDNA molecule is uniquely labeled by random attachment of barcode sequences to both ends (Shiroguchi K, et al. Proc Natl Acad Sci USA. 2012 Jan. 24; 109(4):1347-52). After PCR, paired-end deep sequencing is applied to read the two barcodes and cDNA sequences. Rather than counting the number of reads, RNA abundance is measured based on the number of unique barcode sequences observed for a given cDNA sequence (Shiroguchi K, et al. Proc Natl Acad Sci USA. 2012 Jan. 24; 109(4):1347-52). The barcodes may be optimized to be unambiguously identifiable, even in the presence of multiple sequencing errors. This method allows counting with single-copy resolution despite sequence-dependent bias and PCR-amplification noise, and is analogous to digital PCR but amendable to quantifying a whole transcriptome (Shiroguchi K, et al. Proc Natl Acad Sci USA. 2012 Jan. 24; 109(4):1347-52).

Fixation of cells or tissue may involve the use of crosslinking agents, such as formaldehyde, and may involve embedding cells or tissue in a paraffin wax or polyacrylamide support matrix (Chung K, et al. Nature. 2013 May 16; 497(7449): 322-7).

Amplification may involve thermocycling or isothermal amplification (such as through the methods RPA or LAMP).

Cross-linking may involve overlap-extension PCR or use of ligase to associate multiple amplification products with each other.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

Sequencing may be performed on any high-throughput platform with read-length (either single- or paired-end) sufficient to cover both template and cross-linking event UID's. Methods of sequencing oligonucleotides and nucleic acids are well known in the art (see, e.g., WO93/23564, WO98/28440 and WO98/13523; U.S. Pat. Nos. 5,525,464; 5,202,231; 5,695,940; 4,971,903; 5,902,723; 5,795,782; 5,547,839 and 5,403,708; Sanger et al., Proc. Natl. Acad. Sci. USA 74:5463 (1977); Drmanac et al., Genomics 4:114 (1989); Koster et al., Nature Biotechnology 14:1123 (1996); Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al., Science 281:363 (1998); Nyren et al., Anal. Biochem. 151:504 (1985); Canard and Arzumanov, Gene 11:1 (1994); Dyatkina and Arzumanov, Nucleic Acids Symp Ser 18:117 (1987); Johnson et al., Anal. Biochem. 136:192 (1984); and Elgen and Rigler, Proc. Natl. Acad. Sci. USA 91(13):5740 (1994), all of which are expressly incorporated by reference).

The present invention may be applied to (1) single-cell transcriptomics: cDNA synthesized from mRNA is barcoded and cross-linked during in situ amplification, (2) single-cell proteomics: cDNA or DNA synthesized from RNA- or DNA-tagged antibodies of one or multiple specificities maps the abundance and distributions of different protein-antigens and (3) whole-tissue transcriptomic/proteomic mapping (molecular microscopy or VIPUR microscopy): using the frequency of cross-contamination between cells to determine their physical proximity, and via applications (1) single-cell transcriptomics and (2) single-cell proteomics, determining the global spatial distribution of mRNA, protein, or other biomolecules in a biological sample. This may be used, for example, to screen for anti-cancer/pathogen immunoglobulins (by analyzing co-localization of B-cells and T-cells within affected tissue) for immunotherapy.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "variant" should be taken to mean the exhibition of qualities that differ, such as, but not limited to, genetic variations including SNPs, insertion deletion events, and the like.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. % homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible— reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, 4th Ed. —Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174(2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as omithine (hereinafter referred to as Z), diaminobutyric acid ornithine (hereinafter referred to as B), norleucine ornithine (hereinafter referred to as O), pyriyl-alanine, thienylalanine, naphthylalanine and phenylglycine.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., 1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, ß-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, $\beta$-galactosidase, $\beta$-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin;
diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., international patent application serial no. PCT/US2013/61182 filed Sep. 23, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, a detectable oligonucleotide tag may comprise one or more non-oligonucleotide detectable moieties. Examples of detectable moieties include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art In some embodiments, the detectable moieties are quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity which may comprise the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR. A capture sequence is a sequence capable of being bound by a capture entity. A capture entity may be an oligonucleotide which may comprise a nucleotide sequence complementary to a capture sequence, e.g. a second detectable oligonucleotide tag. A capture entity may also be any other entity capable of binding to the capture sequence, e.g. an antibody, hapten or peptide. An index sequence is a sequence which may comprise a unique nucleotide sequence and/or a detectable moiety as described above.

"Complementary" is a term which is used to indicate a sufficient degree of complementarity between two nucleotide sequences such that stable and specific binding occurs between one and preferably more bases (or nucleotides, as the terms are used interchangeably herein) of the two sequences. For example, if a nucleotide in a first nucleotide sequence is capable of hydrogen bonding with a nucleotide in second nucleotide sequence, then the bases are considered to be complementary to each other. Complete (i.e., 100%) complementarity between a first nucleotide sequence and a second nucleotide is preferable, but not required for ligation, priming, or capture sequences.

The present invention also relates to a computer system involved in carrying out the methods of the invention relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system may comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine readable medium which may comprise computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device which may comprise a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

The present invention also contemplates multiplex assays. The present invention is especially well suited for multiplex assays. For example, the invention encompasses use of a SureSelect$^{XT}$, SureSelect$^{XT2}$ and SureSelect$^{QXT}$ Target Enrichment System for Illumina Multiplexed Sequencing developed by Agilent Technologies (see, e.g., www.agilent.com/genomics/protocolvideos), a SeqCap EZ kit developed by Roche NimbleGen, a TruSeq® Enrichment Kit developed by Illumina and other hybridization-based target enrichment methods and kits that add sample-specific sequence tags either before or after the enrichment step as well as Illumina HiSeq, MiSeq and NexSeq, Life Technology Ion Torrent. Pacific Biosciences PacBio RSII, Oxford Nanopore MinIon, PromethIon and GridIon and other massively parallel Multiplexed Sequencing Platforms.

Usable methods for hybrid selection are described in Melnikov, et al., Genome Biology 12:R73, 2011; Geniez, et al., Symbiosis 58:201-207, 2012; and Matranga, et al., Genome Biology 15:519, 2014). Bait design and hybrid selection was done similarly to a previously published method (see, e.g., Gnirke, et al., Nature biotechnology 27:182-189, 2009, US patent publications No. US 2010/0029498, US 2013/0230857, US 2014/0200163, US 2014/0228223, and US 2015/0126377 and international patent publication No. WO 2009/099602). Briefly, baits may be designed by first concatenating all consensus sequences (such as LASV) into two single bait sets (such as one for Nigerian clades and another for the Sierra Leone clade). Duplicate probes, defined as a DNA sequence with 0 mismatches, were removed. The baits sequences were tiled across the genome (such as LASV) creating a probe every 50 bases. Two sets of adapters were used for each bait set. Adapters alternated with each 50 base probe to improve the efficiency of PCR amplification of probes. The oligo array was synthesized on a CustomArray B3 Synthesizer, as recommended by the manufacturer. The oligonucleotides were cleaved-off the array and amplified by PCR with primers containing T7 RNA polymerase promoters. Biotinylated baits were then prepared through in vitro transcription (MEGAshortscript, Ambion). RNA baits for each clade were prepared separately and mixed at the equal RNA concentration prior to hybridization. Libraries of the genome (such as LASV) were added to the baits and hybridized over a 72 hrs. After capture and washing, libraries were amplified by PCR using the Illumina adapter sequences. Libraries were then pooled and sequenced on the MiSeq platform.

In one aspect of the invention, a method for analyzing a pathogen sequence, such as a bacterial or viral sequence, is provided. The method may comprise sequencing the pathogen sequence according to the method for analyzing a sample which may comprise a target sequence as described above, wherein the target sequence is the pathogen sequence. Preferably the pathogen sequence is a genome of the pathogen or a fragment thereof. The method further may comprise determining the evolution of the pathogen from the sequenced pathogen sequence. Determining the evolution of the pathogen may comprise identification of pathogen mutations in the sequenced pathogen sequence, e.g. nucleotide deletion, nucleotide insertion, nucleotide substitution. Amongst the latter, there are nonsynonymous, synonymous, and noncoding substitutions. Mutations are more frequently nonsynonymous during an outbreak. The method may further comprise determining the substitution rate between two pathogen sequences analyzed as described above. Whether the mutations are deleterious or even adaptive would require functional analysis, however, the rate of nonsynonymous mutations suggests that continued progression of this epidemic could afford an opportunity for viral adaptation, underscoring the need for rapid containment Thus, the method may further comprise assessing the risk of viral adaptation, wherein the number nonsynonymous mutations is determined. (Gire, et al., Science 345, 1369, 2014).

Screening of Compounds

Accordingly, the invention involves a non-human eukaryote, animal, mammal, primate, rodent, etc or cell thereof or tissue thereof that may be used as a disease model. As used herein, "disease" refers to a disease, disorder, or indication in a subject. For example, a method of the invention may be used to create a non-human eukaryote, e.g., an animal, mammal, primate, rodent or cell that comprises a modification, e.g., 3-50 modifications, in one or more nucleic acid sequences associated or correlated with a disease caused by a *Fusobacterium* infection. Such a mutated nucleic acid sequence be associated or correlated with a disease caused by a *Fusobacterium* infection and may encode a disease associated protein sequence or may be a disease associated or correlated control sequence. The cell may be in vivo or ex vivo in the cases of multicellular organisms. In the instance where the cell is in cultured, a cell line may be established if appropriate culturing conditions are met and preferably if the cell is suitably adapted for this purpose (for instance a stem cell). Hence, cell lines are also envisaged. In some methods, the disease model can be used to study the effects of mutations on the animal or cell and development and/or progression of the disease using measures commonly used in the study of the disease. Alternatively, such a disease model is useful for studying the effect of a putatively pharmaceutically active compound or gene therapy on the disease. A disease-associated gene or polynucleotide can be modified to give rise to the disease in the model, and then putatively pharmaceutically active compound and/or gene therapy can be administered so as to observe whether disease development and/or progression is inhibited or reduced. In particular, the method comprises modifying so as to produce, one or more, advantageously 3-50 or more disease-associated or correlated gene(s) or polynucleotide(s). Accordingly, in some methods, a genetically modified animal may be compared with an animal predisposed to development of the disease, such that administering putative gene therapy, or pharmaceutically acceptable compound(s), or any combination thereof can be performed to assess how such putative therapy(ies) or treatment(s) may perform in a human.

Screening of such putative pharmaceutically active compound(s) and/or gene therapy(ies) can be by cellular function change and/or intracellular signaling or extracellular signaling change. Such screening can involve evaluating for dosages or dose curves, as well as combinations of potential drugs and/or therapies. An altered expression of one or more genome sequences associated with a signaling biochemical pathway can be determined by assaying for a difference in the mRNA levels of the corresponding genes between the disease model eukaryote or animal or cell or tissue thereof and a normal eukaryote, animal, tissue or cell, and to ascertain whether when the disease model is administered or contacted with a candidate chemical agent or gene therapy it reverts to or towards normal. An assay can be for mutation(s)-induced alteration in the level of mRNA transcripts or corresponding polynucleotides in comparison with such level(s) in a normal eukaryote or animal and whether such level(s) are placed towards or to normal when a therapy or treatment or agent is employed.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser.

No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6 Oct. 2014; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121): 819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature2466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure™, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banejee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., "Crystal Structure of *Staphylococcus aureus* Cas9," Cell 162, 1113-1126 (Aug. 27, 2015)

Zetsche et al. (2015), "Cpf1 is a single RNA-guided endonuclease of a class 2 CRISPR-Cas system," Cell 163, 759-771 (Oct. 22, 2015) doi: 10.1016/j.cell.2015.09.038. Epub Sep. 25, 2015

Shmakov et al. (2015), "Discovery and Functional Characterization of Diverse Class 2 CRISPR-Cas Systems," Molecular Cell 60, 385-397 (Nov. 5, 2015) doi: 10.1016/j.molcel.2015.10.008. Epub Oct. 22, 2015

Dahlman et al., "Orthogonal gene control with a catalytically active Cas9 nuclease," Nature Biotechnology 33, 1159-1161 (November, 2015)

Gao et al, "Engineered Cpf1 Enzymes with Altered PAM Specificities," bioRxiv 091611; doi: http://dx.doi.org/10.1101/091611 Epub Dec. 4, 2016

Smargon et al. (2017), "Cas13b Is a Type VI-B CRISPR-Associated RNA-Guided RNase Differentially Regulated by Accessory Proteins Csx27 and Csx28," Molecular Cell 65, 618-630 (Feb. 16, 2017) doi: 10.1016/j.molcel.2016.12.023. Epub Jan. 5, 2017 each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*. 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Gao et al. (2016) reported using a structure-guided saturation mutagenesis screen to increase the targeting range of Cpf1. AsCpf1 variants were engineered with the mutations S542R/K607R and S542R/K548V/N552R that can cleave target sites with TYCV/CCCC and TATV PAMs, respectively, with enhanced activities in vitro and in human cells.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Analysis of *Fusobacterium* Persistence and Antibiotic Response in Human Colorectal Cancers In colorectal cancer, malignant cells are surrounded by a complex microenvironment encompassing a range of non-transformed cells, but also a diverse collection of microorganisms. Increasing evidence links alterations in the composition of the gut microbiota with colorectal cancer. Applicants demonstrate that *Fusobacterium* is persistently associated with colorectal cancer in liver metastases and in multiple generations of patient derived xenografts in mice. *Fusobacterium* persistence is associated with other gram-negative anaerobes including *Bacteroides fragilis* and *Selenomonas* sputigena. Colorectal cancer-derived *Fusobacterium nucleatum* isolates are invasive in cell culture and there is evidence of bacterial invasion in respective patient derived xenografts. Finally, treatment of mice bearing xenografts of human colorectal cancers with the *Fusobacterium*-killing antibiotic, metronidazole, reduces tumor growth rate and cancer cell proliferation. Applicants' observations that *Fusobacterium*-associated colorectal cancers exhibit a distinct microbial signature; that this signature is maintained through metastasis and multiple serial passages of xenografts in mice; and that antibiotics targeting *Fusobacterium* can retard the growth of *Fusobacterium*-enriched xenografts, strongly support a key role for *Fusobacterium* infection in the proliferation of colorectal cancer and suggest new opportunities for therapeutic intervention.

*Fusobacterium* species and the associated microbiome persist in liver metastases and mouse xenografts of human colon cancer; antibiotic treatment reduces xenograft growth.

Cancers, like other diseased or healthy tissues, are comprised of Applicants' own eukaryotic cells encoded by our own genomes, together with a diverse population of associated microorganisms (the microbiota). The microbiota and host form a complex 'super-organism' in which symbiotic relationships confer benefits necessary for human health (Schwabe et al., *Nat Rev Cancer* 13, 800-812 (2013)) in addition to pathogenic consequences. Recent studies have demonstrated that perturbations in the composition of the human microbiota, or dysbiosis, can significantly increase the risk of specific cancer types, especially colorectal cancer (CRC) (Hope et al., *FEMS Microbiol Lett* 244, 1-7 (2005); Rowland et al., *Curr Pharm Des* 15, 1524-1527 (2009); Yang et al., *World J Gastroenterol* 12, 6741-6746 (2006)). The human colon is the anatomical location with the largest number of microbes; a growing body of evidence demonstrates the role of particular microorganisms in modulating inflammatory environments and promoting tumor growth and metastasis. Such organisms include the pro-inflammatory enterotoxigenic *Bacteroides fragilis* (ETBF) (Wu et al., *Nat Med* 15, 1016-1022 (2009)) and colibactin-producing *E. coli* (Arthur et al., *Science* 338, 120-123 (2012)).

Recent evidence has proposed an association of *Fusobacterium nucleatum* with human colon cancers (Kostic et al., *Genome research* 22, 292-298 (2012); Castellarin et al., *Genome research* 22, 299-306 (2012)). Subsequent metagenomic and molecular analyses across North America (Tahara et al., *Cancer research* 74, 1311-1318 (2014); McCoy et al., *PloS one* 8, e53653 (2013)), Europe (Flanagan et al., *European journal of clinical microbiology & infectious diseases: official publication of the European Society of Clinical Microbiology* 33, 1381-1390 (2014)), Asia (Li et al., *World journal of gastroenterology* 22, 3227-3233 (2016); Ito et al., *International journal of cancer* 137, 1258-1268 (2015)) and Africa (Viljoen et al., *PloS one* 10, e0119462 (2015)) have confirmed a consistent enrichment of *Fusobacterium* in human colorectal carcinomas and adenomas compared with adjacent normal tissue. Increased tumor levels of *F. nucleatum* correlates with a lower T-cell response, poorer patient survival and advanced disease stage (Flanagan et al., *European journal of clinical microbiology & infectious diseases: official publication of the European Society of Clinical Microbiology* 33, 1381-1390 (2014); Ito et al., *International journal of cancer* 137, 1258-1268 (2015); Mima et al., *Gut*, (2015); Mima et al., *JAMA* oncology 1, 653-661 (2015)) along with specific clinical and molecular subsets of CRC including right-sided anatomic location, BRAF mutation, and hypermutation with microsatellite instability (Tahara et al., Cancer research 74, 1311-1318 (2014); Li et al., World journal of gastroenterology 22, 3227-3233 (2016); Mima et al., Gut, (2015)).

Although these studies provide compelling evidence for the association of Fusobacterium with CRC, a basic question remains; does Fusobacterium enrichment cause colon cancer or is it predominantly a consequence of the cancer itself? In attempts to address this question Applicants previously demonstrated that exposure of Apc$^{Min/+}$ mice to F. nucleatum was sufficient to accelerate murine small intestinal adenocarcinoma development (Kostic et al., Cell host & microbe 14, 207-215 (2013)). Also, F. nucleatum has been shown to modulate human and murine tumor immune infiltrates, potentially providing colonized tumors with an immune evasion mechanism (Kostic et al., Cell host & microbe 14, 207-215 (2013); Gur et al., Immunity 42, 344-355 (2015)). Although these findings support a role for Fusobacterium in colorectal cancer beyond an innocent bystander, such approaches have been limited to externally-induced single organism infections of murine cancers as well as in vitro assays, which do not (and cannot) account for the complexity of the microbial mileu in regulating the growth and proliferation of human tumors (Kostic et al., Cell host & microbe 14, 207-215 (2013); Gur et al., Immunity 42, 344-355 (2015)).

To investigate the relationship of Fusobacterium with human colon cancers in vivo Applicants set out to determine if Fusobacterium could persist in distant site metastases and in patient-derived xenografts (PDXs), which could provide a more discriminative model for functional analysis and intervention.

First, Applicants asked whether Fusobacterium observed in colorectal tumors persists in the setting of distant metastasis. Preliminary observations from Applicants (Kostic et al., Genome research 22, 292-298 (2012)) and others (Abed et al., Cell host & microbe 20, 215-225 (2016)) have demonstrated the presence of Fusobacterium DNA in hepatic and lymph node metastases of colon cancer using quantitative PCR (qPCR) measurements. However these samples were not paired with primary colon cancers to evaluate the persistence of the bacteria.

Figure 10A:
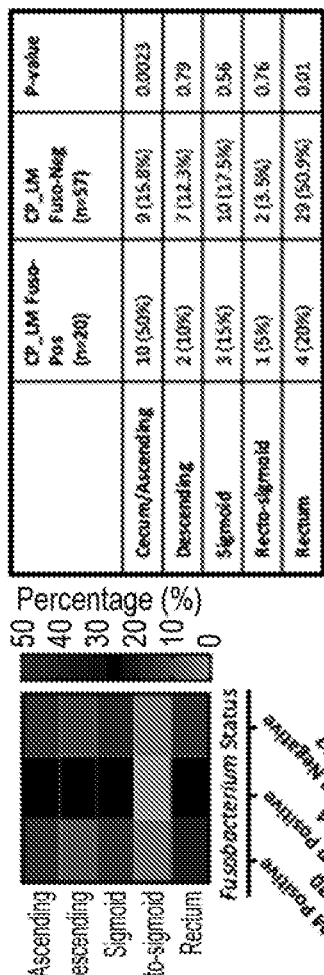
FIGS. 10A-10D: *Fusobacterium* associated cecum/ascending colon tumors.
Figure 10B:
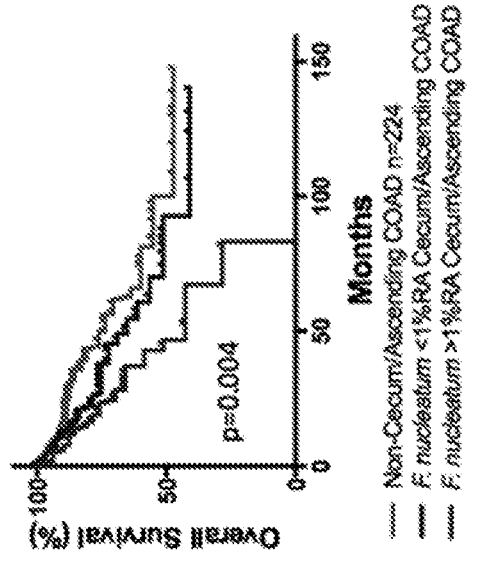

To assess whether Fusobacterium and other tumor-associated bacteria are present in corresponding metastases from Fusobacterium-colonized primary CRCs, Applicants began by testing formalin-fixed, paraffin-embedded sections of primary colon tumors and liver metastases, similar to previous studies (REFs), but now in paired samples and from a larger cohort of 101 patients. 43% (n=44/101) of primary colon cancers tested positive for Fusobacterium by qPCR, and 45% (n=20/44) of liver metastases from these Fusobacterium-positive primary tumors were Fusobacterium qPCR positive (FIG. 1A). None of the 57 Fusobacterium-negative primary colon tumors were associated with a Fusobacterium-positive liver metastasis (n=0/57; p=) (FIG. 1A, FIG. 10A). Additionally, the presence of Fusobacterium in paired primary tumors and corresponding metastasis was enriched in metastatic cecum/ascending colon cancers (n=10/20, p=0.002), while cancers that were Fusobacterium-negative in both primary and metastasis were more likely to be rectal cancers (n=29/57 of the Fusobacterium-negative primary-metastasis pairs, p=0.016).

Figure 10C:
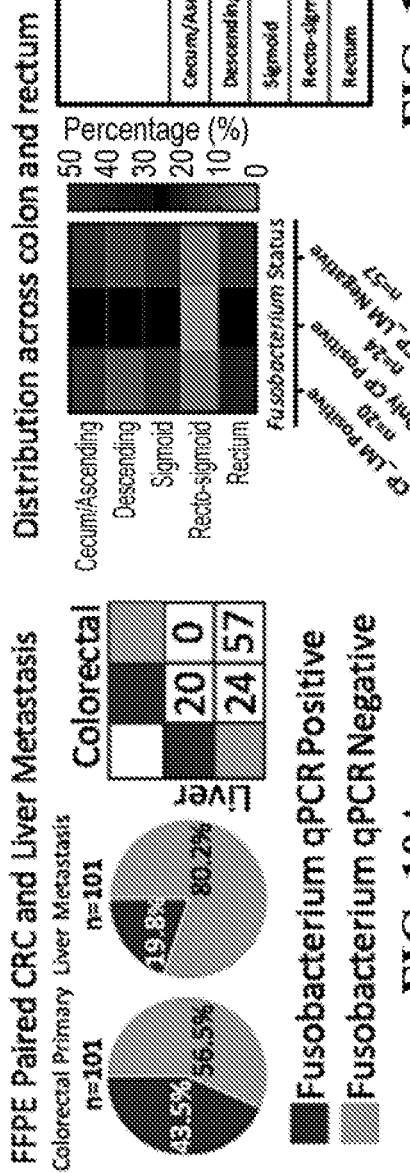
Figure 10D:
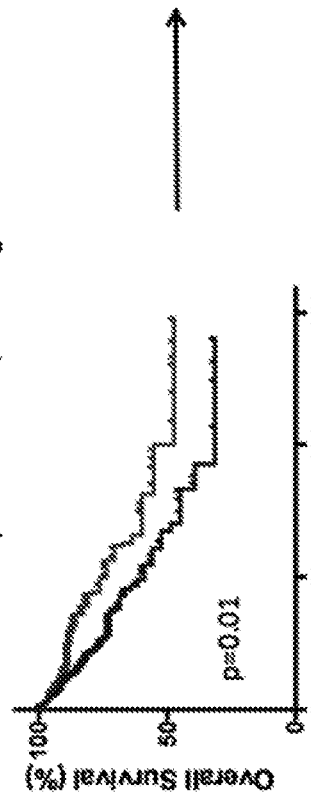

To assess the relationship between Fusobacterium presence in the primary cecum/ascending colon and patient survival, Applicants carried out PathSeq analysis (Kostic et al., Nat Biotechnol 29, 393-396 (2011)) on RNA sequencing data from the 430 primary colon adenocarcinomas in the "TCGA cohort". Patients with cecum/ascending colon cancer exhibited worse overall survival than patients with non-cecum/ascending colon cancer in the TCGA cohort (p=0.01) (FIG. 10C). Among patients with cecum/ascending colon tumors, we observed significantly poorer overall survival in correlation with tumor Fusobacterium load (FIG. 10C, p=0.004).

Figure 1B:
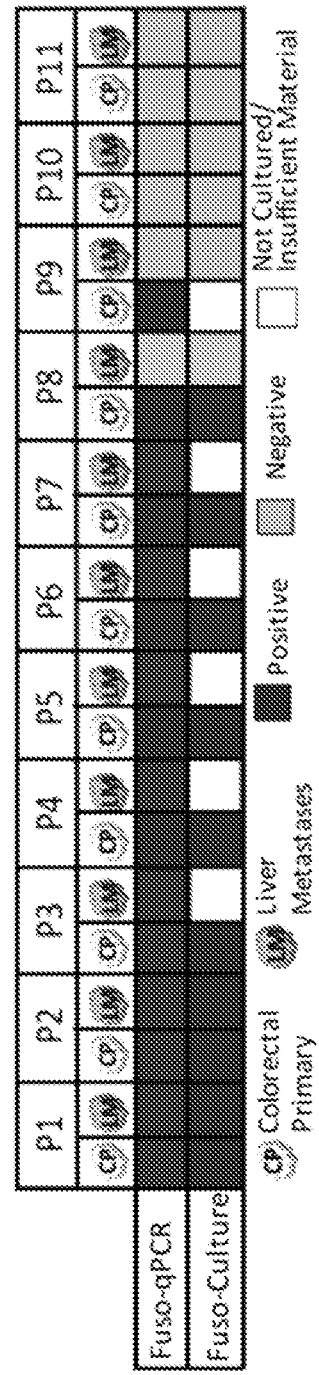
Figure 6A:
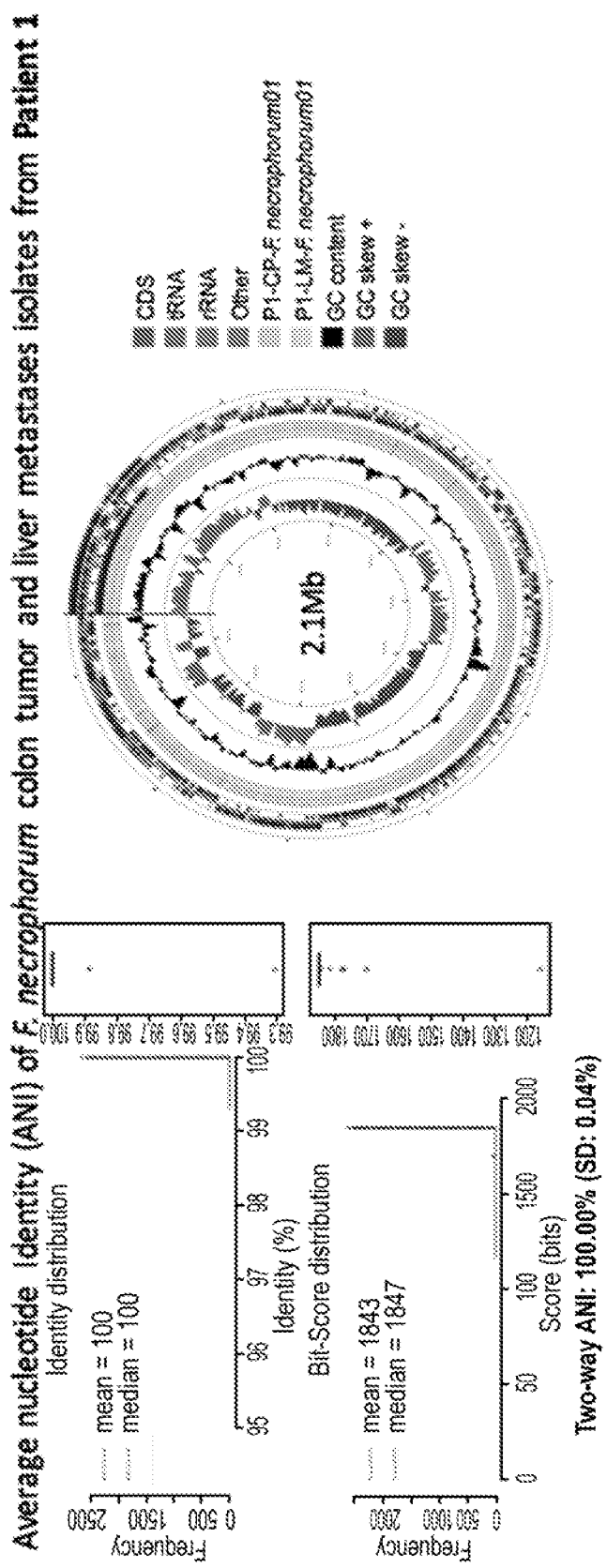
FIG. 6A-6B: Identical strains of *Fusobacterium* colonize both the primary colorectal tumor and liver metastasis of respective patients.
Figure 6B:
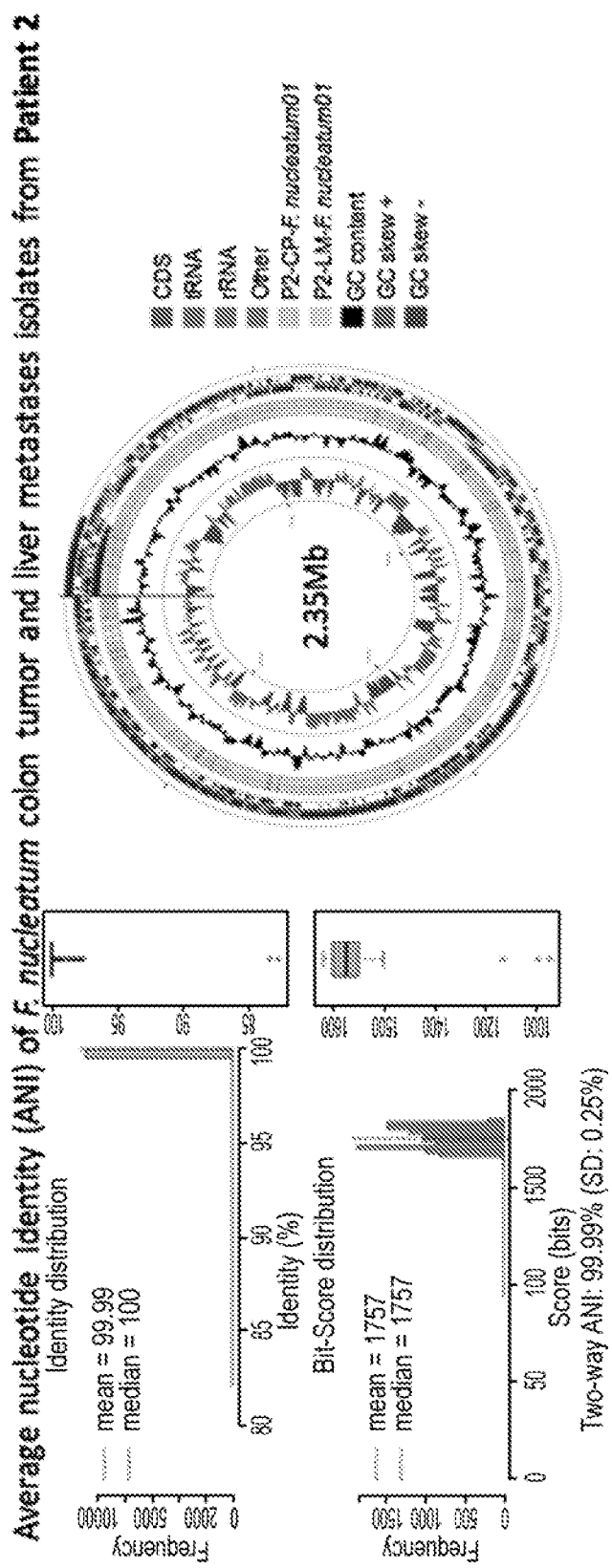
Figure 7:
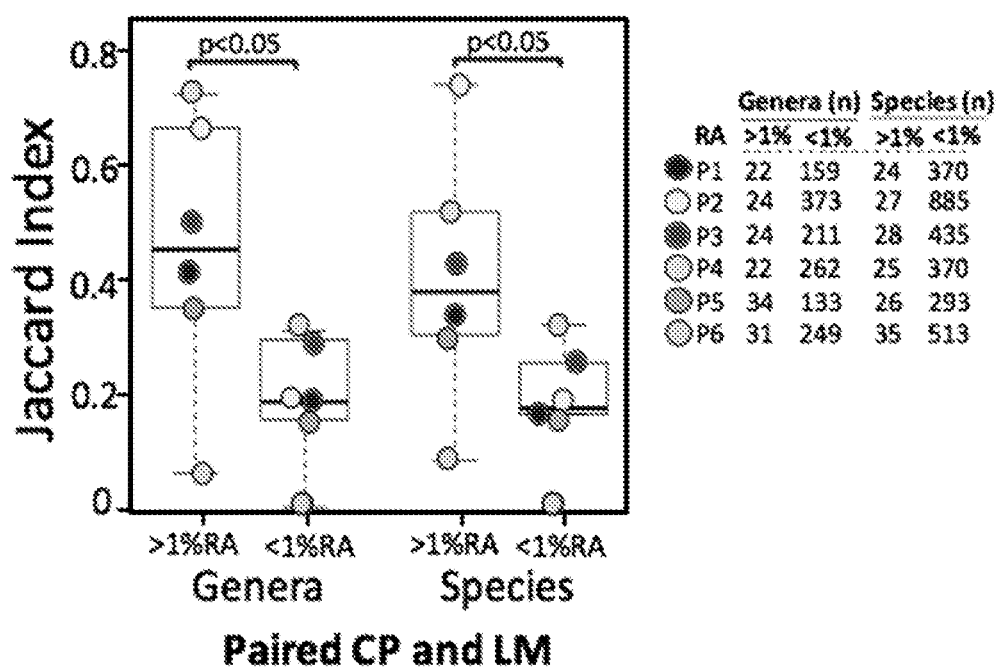
FIG. 7: The dominant bacterial genera and species in colorectal primary tumors are also dominant genera and species in corresponding liver metastasis. Box plots represent the Jaccard Index (proportion of shared genera/species) between paired colorectal primary (CP) tumors and liver metastases (LM) at both the genus and species level at 1% relative abundance (RA) and <1% RA of the *Fusobacterium*-positive primary-metastases pairs (n=6). The box represents the first and third quartiles, and error bars indicate 95% confidence of median. P values were determined using the z score test for two population proportions (two-tailed), the number of shared organisms between individual patient primary-metastasis pairs were compared at >1% and <1% RA genera and species, in all cases the p<0.05.

Next, Applicants wanted to determine whether they could culture viable Fusobacterium strains from primary CRC and corresponding liver metastases. Of eleven snap-frozen primary-metastasis tumor pairs that were suitable for microbial culture, Applicants could successfully culture Fusobacterium species from primary tumors and liver metastases from two patients (P1 and P2), although seven (64%) pairs tested positive for Fusobacterium by qPCR (FIG. 1B). Whole genome sequencing analysis of tumors from patients P1 and P2 revealed identical strains of Fusobacterium in both the primary colorectal tumors and their associated liver metastases, despite the tissue being collected up to two years apart. Applicants cultured F. necrophorum subsp. funduliforme from the primary colorectal tumor and liver metastases of patient P1 and F. nucleatum subsp. animalis from the primary colorectal tumor and liver metastases of patient P2 (FIG. 6A-6B). In addition to culturing Fusobacterium species from the primary-metastasis pairs, Applicants have cultured a range of other co-occurring anaerobes, including Bacteroides species (Table 1). Interestingly, Applicants noted that a higher fraction of colorectal adenocarcinomas with metastases (n=8/11 or 73%) were Fusobacterium culture-positive compared to an independent set of surgically resected colorectal adenocarcinomas for which metastatic outcome was unknown (n=15/53, or 28%) (p=0.01, non-parametric Fisher's exact test) (Table 2).

TABLE 1

Selected bacterial species isolated from colorectal primary tumors and/or liver metastasis.

Bacterial species cultured from both primary-metastasis pairs
Patient 1 (P1) colorectal primary and liver metastasis

*Fusobacterium necrophorum*
*Bacteroides fragilis*
*Escherichia coli*
*Streptococcus sanguinis*
Patient 2 (P2) colorectal primary and liver metastasis

*Fusobacterium nucleatum*
*Gemella morbillorum*
*Bacteroides uniformis*
*Clostridium Hathaway*
*Streptococcus sanguinis*
Patient 4 (P4) colorectal primary and liver metastasis

*Parvimonas micra*
*Bacteroides thetaiotaomicron*
*Solobacterium moorei*
*Bacteroides salyersiae*
*Bacteroides ovatus*
Selected species isolated from either primary or metastasis tumors
Patient 1 (P1) liver metastasis

*Gemella morbillorum*
*Eggerthella lenta*
Patient 2 (P2) colorectal primary

*Campylobacter ureolyticus*
*Porphyromonas asaccharolytica*

TABLE 1-continued

Selected bacterial species isolated from colorectal primary tumors and/or liver metastasis.

Patient 3 (P3) colorectal primary

*Fusobacterium nucleatum*
*Campylobacter ureolyticus*
*Porphyromonas asaccharolytica*
Patient 4 (P4) colorectal primary

*Fusobacterium nucleatum*
*Campylobacter gracilis*
*Prevotella intermedia*
*Mogibacterium timidum*
*Parvimonas micra*
Patient 4 (P4) liver metastasis

*Olsenella uli*
*Ruminococcus gnavus*
*Eggerthella* species
Patient 5 (P5) colorectal primary

*Fusobacterium nucleatum*
*Campylobacter ureolyticus*
*Alistipes shahii*
*Akkermansia muciniphila*
Patient 6 (P6) colorectal primary

*Fusobacterium necrophorum*
*Porphyromonas asaccharolytica*
Patient 7 (P7) colorectal primary

*Fusobacterium nucleatum*
*Parvimonas micra*
Patient 8 (P8) colorectal primary

*Fusobacterium nucleatum*
*Bacteroides fragilis*
Patient 9 (P9) colorectal primary

*Campylobacter ureolyticus*
Patient 10 (P10) colorectal primary

*Veillonella parvula*
*Odoribacter splanchnicus*
Patient 11 (P11) colorectal primary

*Odoribacter splanchnicus*

TABLE 2

Metastatic colorectal tumors have a higher proportion of *Fusobacterium* culture positives. Fisher's exact test, p = 0.01.

| CR | | *Fusobacterium* Culture | |
|---|---|---|---|
| | | Positive | Negative |
| C | With Metastases | 8 | 3 |
| | Metastases Unknown | 15 | 38 |

Figure 1C:
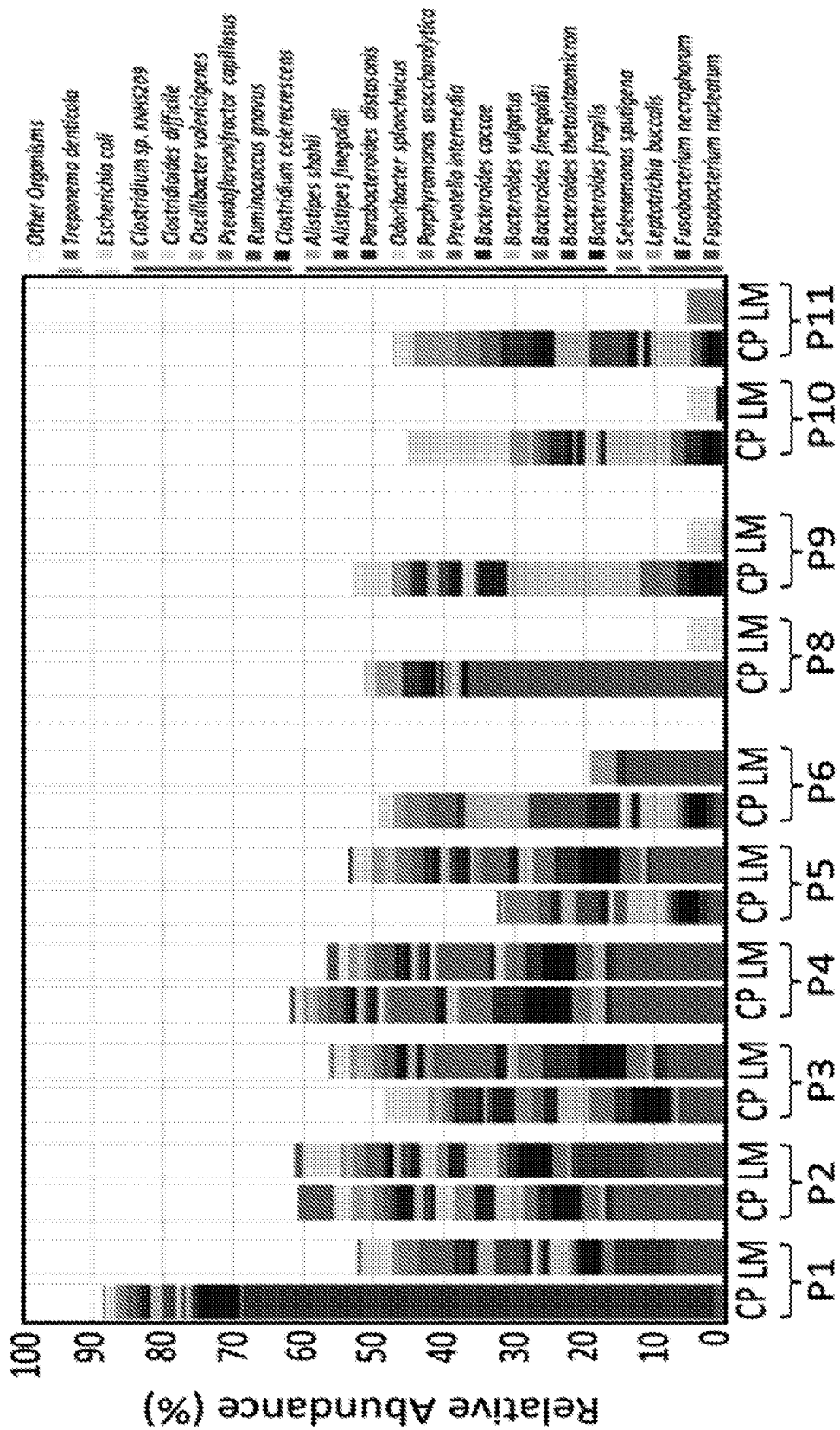
Figure 1E:
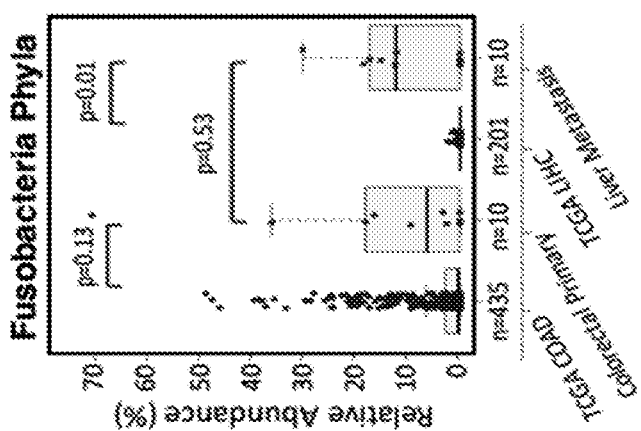
Figure 1D:
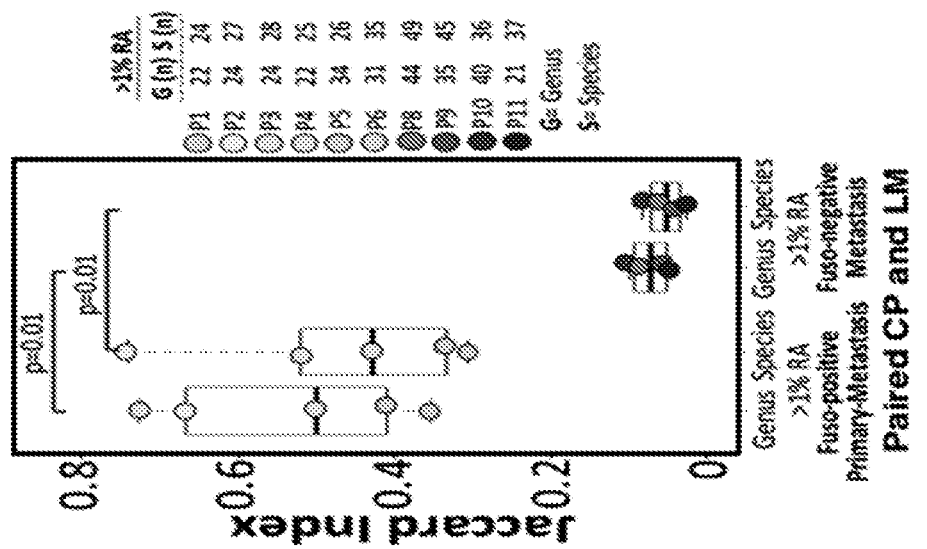
Figure 9A:
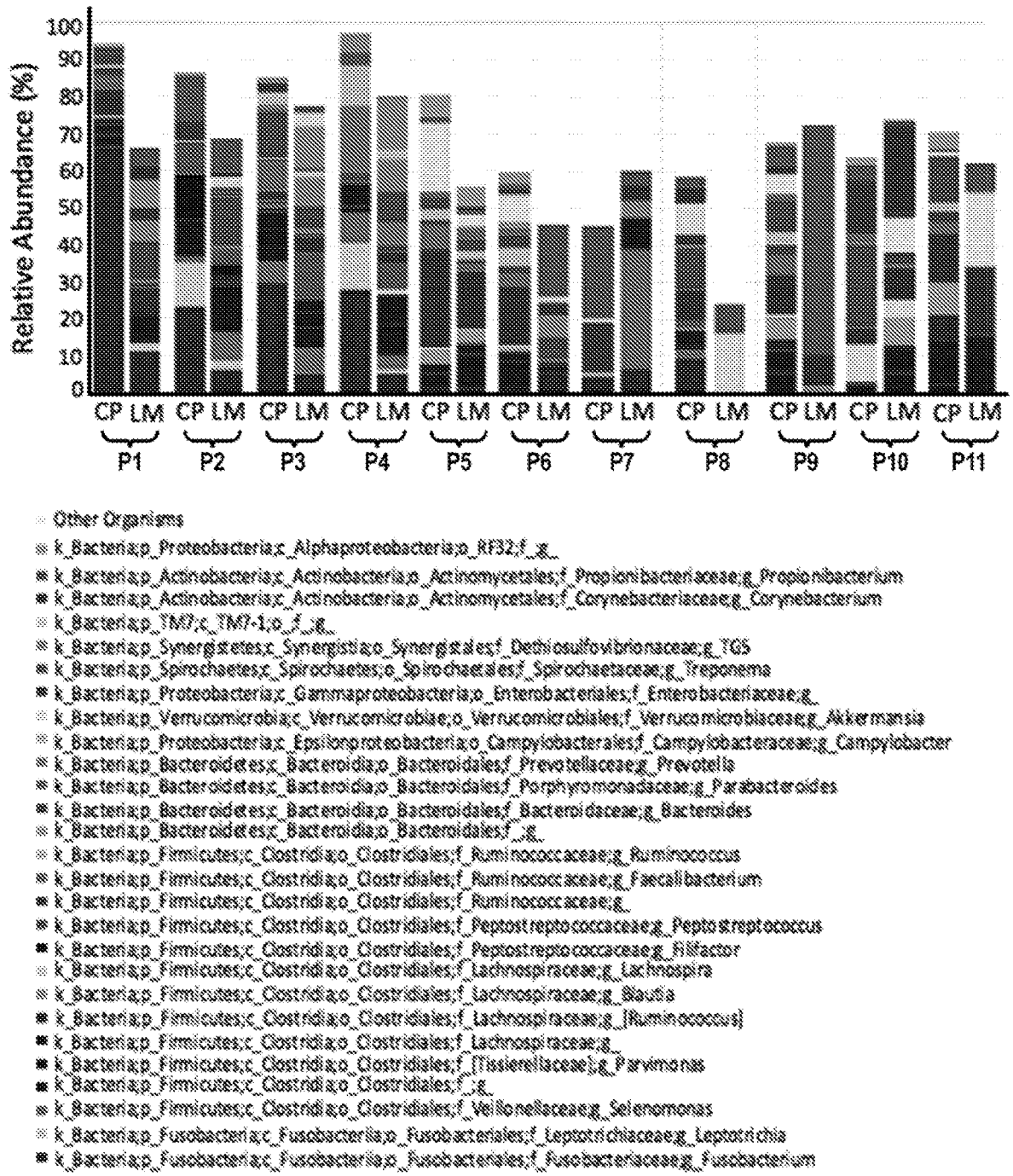
FIGS. 9A-9C: Bacterial 16S rRNA gene sequencing demonstrates *Fusobacterium* colonizes liver metastases of *Fusobacterium*-associated colorectal primary tumors (frozen paired cohort).
Figure 9B:
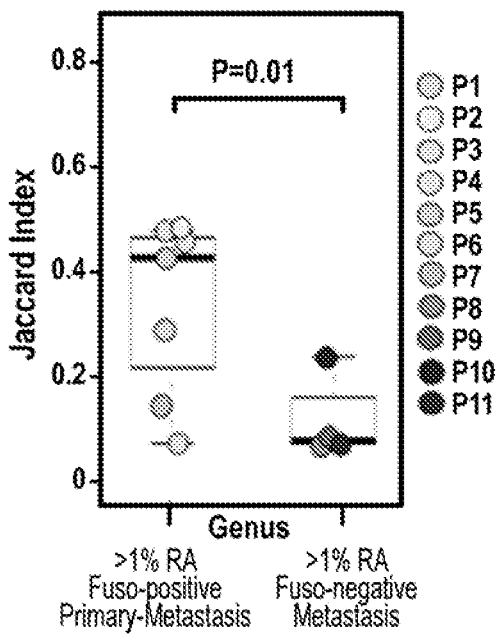
Figure 9C:
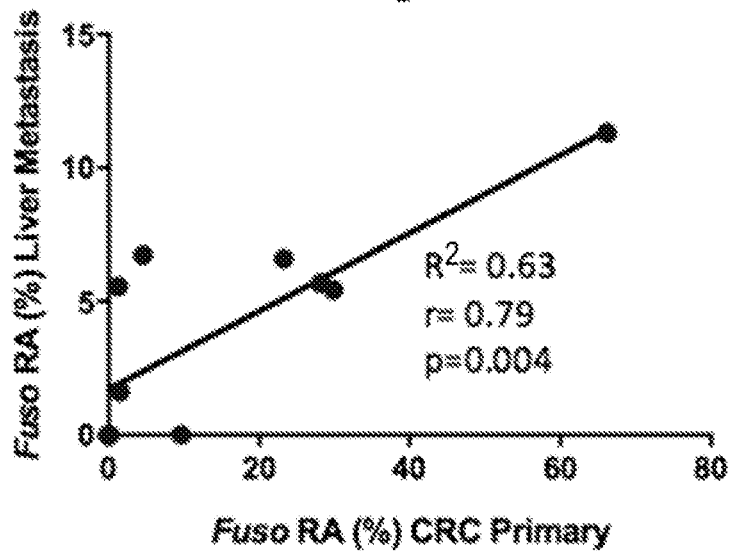

To quantitate *Fusobacterium* abundance and to evaluate the broader microbiome, Applicants performed RNA sequencing analysis of ten primary cancers and their matched liver metastases (patients P1-P6 and P8-P11). PathSeq analysis (Kostic et al., Nat Biotechnol 29, 393-396 (2011)) of the resulting RNA sequencing data shows that the same *Fusobacterium* species are present, at a similarly relative abundance, in paired primary-metastasis pairs (FIG. 1C, samples P1-P6). Furthermore, the overall dominant microbiome is qualitatively similar; persistent microbes in the liver metastases include *F. nucleatum* and *F. necrophorum*, a range of *Bacteroides* species including *B. fragilis* and *B. thetaiotaomicron*, and several typically oral anaerobes such as *Prevotella intermedia* and *Selenomonas* sputigena. In contrast, there was little similarity between the primary colorectal cancer and liver metastasis in the lone sample where *Fusobacterium* was present in the primary cancer but not detected in the metastasis (FIG. 1C, sample P8) or in the three samples with low or undetectable levels of *Fusobacterium* in the primary cancer (FIG. 1C, samples P9-P11). Furthermore, the Jaccard index revealed high correlation between the dominant bacteria in the primary tumor and metastasis for *Fusobacterium*-positive pairs but low correlation for *Fusobacterium*-negative pairs (FIG. 1D and FIGS. 6A-6B). Targeted bacterial 16S rRNA gene sequencing on DNA from the 11 frozen paired samples confirmed that (i) *Fusobacterium* species are present in paired primary-metastatic tumors, (ii) the relative abundance of *Fusobacterium* is correlated between primary tumors and metastases, and (iii) the dominant microbial genera of the liver metastases are correlated with the dominant genera of the primary tumors, demonstrating microbiome stability between paired primary-metastatic tumors harboring *Fusobacterium* (p=0.01), (FIGS. 9A-9C). As a control for liver metastases of colorectal carcinoma, Applicants asked whether Fusobacteria are associated with primary liver hepatocellular carcinoma (LIHC) by PathSeq analysis (Kostic et al., Nat Biotechnol 29, 393-396 (2011)) of RNA sequencing data from 201 primary LIHC tumors from The Cancer Genome Atlas (TCGA). This analysis demonstrated that Fusobacteria are rare in LIHC and that the relative abundance of Fusobacteria is significantly different between TCGA primary LIHC and liver metastases arising from colorectal cancers (p=0.01) (FIG. 1E).

Figure 1F:
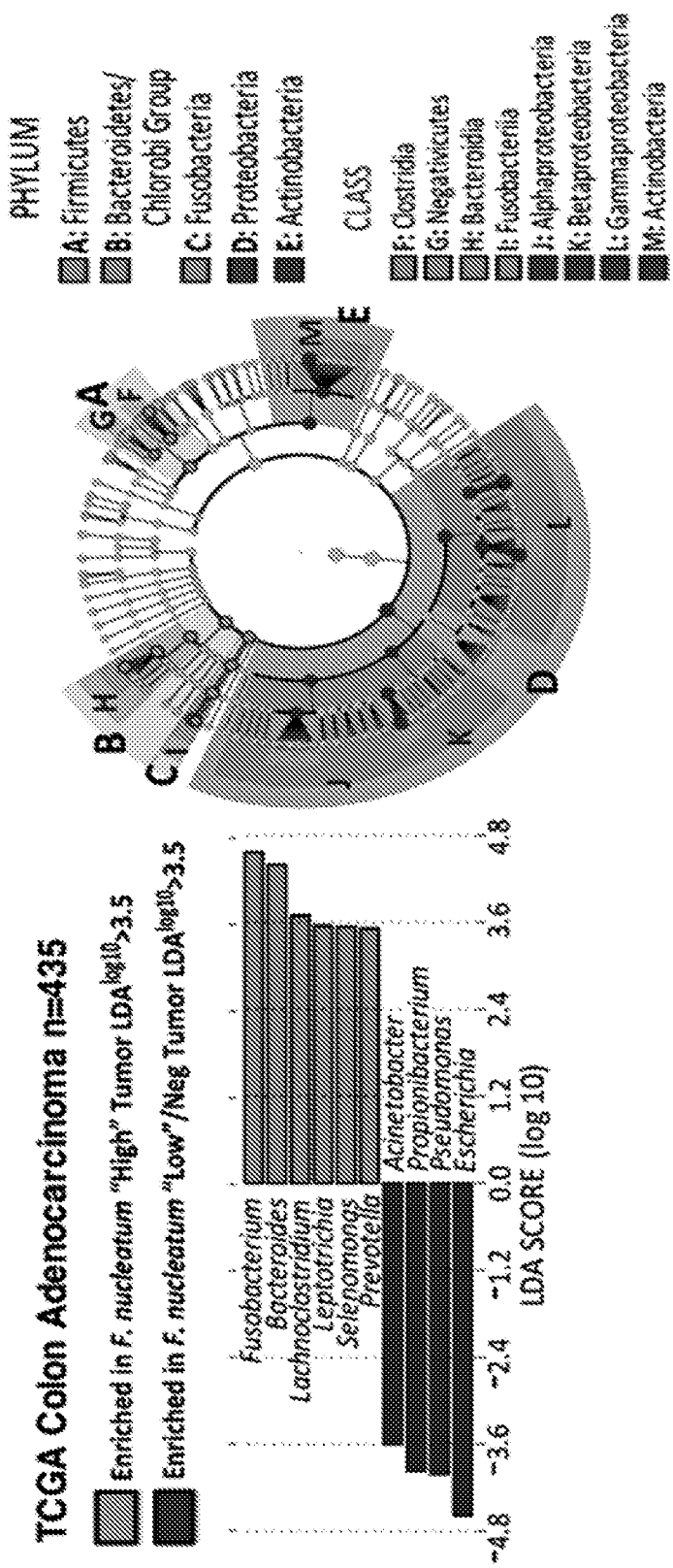

To assess whether the microbes that persist in liver metastases of *Fusobacterium*-positive CRC are similar to those associated with *Fusobacterium* in primary CRC, Applicants carried out PathSeq analysis (Kostic et al., Nat Biotechnol 29, 393-396 (2011)) on RNA sequencing data from 435 primary colon adenocarcinoma (COAD) from TCGA (N. Cancer Genome Atlas, Comprehensive molecular characterization of human colon and rectal cancer. Nature 487, 330-337 (2012)). COAD tumors were divided into two groups based upon *Fusobacterium* abundance. The most abundant anaerobic bacteria in the primary colon cancer and liver metastases, including *Selenomonas*, *Bacteroides* and *Prevotella* genera, showed a correlation with *Fusobacterium* in primary COAD [false discovery rate (FDR)<0.05, non-parametric t test] (FIG. 1F, Table 3). These results demonstrate that *Fusobacterium* and co-occurring tumor anaerobes are maintained and remain viable in distant site metastases.

TABLE 3

Comparative analysis of bacterial genera (A) and species (B) that are significantly enriched in *F. nucleatum* "High" COAD. The top 50 genera or species are shown.
False Discovery Rate (FDR).

|  | Rank | p-value | FDR | Fold Change |
|---|---|---|---|---|
| (A) |  |  |  |  |
| Bacterial Genera |  |  |  |  |
| *FUSOBACTERIUM* | 1 | 0.0020 | 0.0140 | 47.1133 |
| *ILYOBACTER* | 2 | 0.0020 | 0.0140 | 28.8882 |
| *SEBALDELLA* | 3 | 0.0020 | 0.0140 | 15.4157 |
| *STREPTOBACILLUS* | 4 | 0.0020 | 0.0140 | 13.7608 |
| *BACTEROIDES* | 5 | 0.0020 | 0.0140 | 3.4281 |
| *ALKALIPHILUS* | 6 | 0.0020 | 0.0140 | 3.0667 |
| *SYNTROPHOTHERMUS* | 7 | 0.0020 | 0.0140 | 2.9430 |
| *BUTYRIVIBRIO* | 8 | 0.0020 | 0.0140 | 2.7807 |
| *LACHNOCLOSTRIDIUM* | 9 | 0.0020 | 0.0140 | 2.6687 |
| *DICTYOGLOMUS* | 10 | 0.0020 | 0.0140 | 5.4044 |
| *SELENOMONAS* | 11 | 0.0020 | 0.0140 | 11.1374 |
| *ROSEBURIA* | 12 | 0.0020 | 0.0140 | 2.6685 |
| *CELLULOSILYTICUM* | 13 | 0.0020 | 0.0140 | 2.4087 |
| *PEPTOCLOSTRIDIUM* | 14 | 0.0020 | 0.0140 | 2.9072 |
| *LAWSONIA* | 15 | 0.0020 | 0.0140 | 5.0552 |
| *EUBACTERIUM* | 16 | 0.0020 | 0.0140 | 2.5455 |
| *CAMPYLOBACTER* | 17 | 0.0020 | 0.0140 | 7.3743 |
| *RUMINICLOSTRIDIUM* | 18 | 0.0020 | 0.0140 | 2.3232 |
| *ACIDAMINOCOCCUS* | 19 | 0.0020 | 0.0140 | 2.7733 |
| *ACETOBACTERIUM* | 20 | 0.0020 | 0.0140 | 2.4387 |
| *DESULFOVIBRIO* | 21 | 0.0020 | 0.0140 | 2.5469 |
| *CANDIDATUS AZOBACTEROIDES* | 22 | 0.0020 | 0.0140 | 2.5707 |
| *CLOSTRIDIOIDES* | 23 | 0.0020 | 0.0140 | 3.8920 |
| *RHODOTHERMUS* | 24 | 0.0020 | 0.0140 | 2.8532 |
| *PREVOTELLA* | 25 | 0.0020 | 0.0140 | 3.1566 |
| *HALANAEROBIUM* | 26 | 0.0020 | 0.0140 | 2.3960 |
| *PORPHYROMONAS* | 27 | 0.0020 | 0.0140 | 3.8514 |
| *TANNERELLA* | 28 | 0.0020 | 0.0140 | 2.2752 |
| *AMINOBACTERIUM* | 29 | 0.0020 | 0.0140 | 5.5475 |
| *DESULFOTOMACULUM* | 30 | 0.0020 | 0.0140 | 1.9935 |
| *THERMOANAEROBACTERIUM* | 31 | 0.0020 | 0.0140 | 2.3354 |
| *SLACKIA* | 32 | 0.0020 | 0.0140 | 2.9141 |
| *THERMANAEROVIBRIO* | 33 | 0.0020 | 0.0140 | 10.4379 |
| *THERMINCOLA* | 34 | 0.0020 | 0.0140 | 2.3776 |
| *THERMOANAEROBACTER* | 35 | 0.0020 | 0.0140 | 1.8895 |
| *CHLAMYDIA* | 36 | 0.0020 | 0.0140 | 2.9236 |
| *CANDIDATUS DESULFORUDIS* | 37 | 0.0020 | 0.0140 | 2.9047 |
| *LEPTOTRICHIA* | 38 | 0.0020 | 0.0140 | 9.9322 |
| *DESULFITOBACTERIUM* | 39 | 0.0020 | 0.0140 | 2.2703 |
| *ACHOLEPLASMA* | 40 | 0.0020 | 0.0140 | 4.3440 |
| *OSCILLIBACTER* | 41 | 0.0020 | 0.0140 | 2.5028 |
| *DESULFOSPOROSINUS* | 42 | 0.0020 | 0.0140 | 2.0085 |
| *CANDIDATUS ARTHROMITUS* | 43 | 0.0020 | 0.0140 | 1.9736 |
| *THERMOVIRGA* | 44 | 0.0020 | 0.0140 | 4.6990 |
| *SPHAEROCHAETA* | 45 | 0.0020 | 0.0140 | 3.5031 |
| *HYDROGENOBACULUM* | 46 | 0.0020 | 0.0140 | 3.0195 |
| *CORIOBACTERIUM* | 47 | 0.0020 | 0.0140 | 2.7495 |
| *SYNTROPHOBOTULUS* | 48 | 0.0020 | 0.0140 | 2.1824 |
| *ACETOHALOBIUM* | 49 | 0.0040 | 0.0240 | 2.5122 |
| *RUMINOCOCCUS* | 50 | 0.0020 | 0.0140 | 2.1276 |
| (B) |  |  |  |  |
| Bacterial Species |  |  |  |  |
| *FUSOBACTERIUM_NUCLEATUM* | 1 | 0.0019 | 0.016 | 47.0 |
| *ILYOBACTER_POLYTROPUS* | 2 | 0.0019 | 0.016 | 28.9 |
| *SEBALDELLA_TERMITIDIS* | 3 | 0.0019 | 0.016 | 15.4 |
| *STREPTOBACILLUS_MONILIFORMIS* | 4 | 0.0019 | 0.016 | 13.7 |
| *BACTEROIDES_FRAGILIS* | 5 | 0.0019 | 0.016 | 5.0 |
| *CAMPYLOBACTER_CURVUS* | 6 | 0.0019 | 0.016 | 11.5 |
| *DICTYOGLOMUS_TURGIDUM* | 7 | 0.0019 | 0.016 | 5.4 |
| *BACTEROIDES_HELCOGENES* | 8 | 0.0019 | 0.016 | 2.9 |
| *ALKALIPHILUS_METALLIREDIGENS* | 9 | 0.0019 | 0.016 | 3.3 |
| *SYNTROPHOTHERMUS_LIPOCALIDUS* | 10 | 0.0019 | 0.016 | 2.9 |
| *ALKALIPHILUS_OREMLANDII* | 11 | 0.0019 | 0.016 | 2.9 |
| *CLOSTRIDIUM_SP._SY8519* | 12 | 0.0019 | 0.016 | 2.7 |
| *BUTYRIVIBRIO_PROTEOCLASTICUS* | 13 | 0.0019 | 0.016 | 2.8 |
| *LACHNOCLOSTRIDIUM_PHYTOFERMENTANS* | 14 | 0.0019 | 0.016 | 2.6 |
| *[CLOSTRIDIUM]_SACCHAROLYTICUM* | 15 | 0.0019 | 0.016 | 2.7 |
| *ROSEBURIA_HOMINIS* | 16 | 0.0019 | 0.016 | 2.7 |
| *CELLULOSILYTICUM_LENTOCELLUM* | 17 | 0.0019 | 0.016 | 2.4 |

TABLE 3-continued

Comparative analysis of bacterial genera (A) and species (B) that are significantly enriched in F. nucleatum "High" COAD. The top 50 genera or species are shown. False Discovery Rate (FDR).

|  | Rank | p-value | FDR | Fold Change |
|---|---|---|---|---|
| [EUBACTERIUM]_ELIGENS | 18 | 0.0019 | 0.016 | 2.6 |
| SELENOMONAS_SPUTIGENA | 19 | 0.0019 | 0.016 | 16.5 |
| [EUBACTERIUM]_RECTALE | 20 | 0.0019 | 0.016 | 2.5 |
| [CLOSTRIDIUM]_STICKLANDII | 21 | 0.0019 | 0.016 | 2.9 |
| LAWSONIA_INTRACELLULARIS | 22 | 0.0019 | 0.016 | 5.0 |
| SELENOMONAS_RUMINANTIUM | 23 | 0.0019 | 0.016 | 4.5 |
| [CLOSTRIDIUM]_CELLULOLYTICUM | 24 | 0.0019 | 0.016 | 2.5 |
| DESULFOVIBRIO_VULGARIS | 25 | 0.0019 | 0.016 | 3.4 |
| ACIDAMINOCOCCUS_FERMENTANS | 26 | 0.0019 | 0.016 | 2.9 |
| BACTEROIDES_SALANITRONIS | 27 | 0.0019 | 0.016 | 2.3 |
| PORPHYROMONAS_GINGIVALIS | 28 | 0.0019 | 0.016 | 2.2 |
| ACETOBACTERIUM_WOODII | 29 | 0.0019 | 0.016 | 2.4 |
| PREVOTELLA_DENTICOLA | 30 | 0.0019 | 0.016 | 3.0 |
| CAMPYLOBACTER_CONCISUS | 31 | 0.0019 | 0.016 | 8.6 |
| [CLOSTRIDIUM]_CLARIFLAVUM | 32 | 0.0019 | 0.016 | 2.4 |
| CLOSTRIDIUM_SP._BNL1100 | 33 | 0.0019 | 0.016 | 2.2 |
| CLOSTRIDIOIDES_DIFFICILE | 34 | 0.0019 | 0.016 | 3.9 |
| DICTYOGLOMUS_THERMOPHILUM | 35 | 0.0019 | 0.016 | 5.4 |
| RUMINICLOSTRIDIUM_THERMOCELLUM | 36 | 0.0019 | 0.016 | 2.2 |
| RHODOTHERMUS_MARINUS | 37 | 0.0019 | 0.016 | 2.8 |
| ACIDAMINOCOCCUS_INTESTINI | 38 | 0.0019 | 0.016 | 2.6 |
| TANNERELLA_FORSYTHIA | 39 | 0.0019 | 0.016 | 2.3 |
| HALANAEROBIUM_HYDROGENIFORMANS | 40 | 0.0019 | 0.016 | 3.4 |
| THERMOANAEROBACTERIUM_THERMO-SACCHAROLYTICUM | 41 | 0.0019 | 0.016 | 2.5 |
| CHLAMYDIA_TRACHOMATIS | 42 | 0.0019 | 0.016 | 3.2 |
| AMINOBACTERIUM_COLOMBIENSE | 43 | 0.0019 | 0.016 | 5.5 |
| DESULFOTOMACULUM_ACETOXIDANS | 44 | 0.0019 | 0.016 | 2.2 |
| SLACKIA_HELIOTRINIREDUCENS | 45 | 0.0019 | 0.016 | 2.9 |
| DESULFOTOMACULUM_NIGRIFICANS | 46 | 0.0019 | 0.016 | 2.4 |
| THERMANAEROVIBRIO_ACIDAMINOVORANS | 47 | 0.0019 | 0.016 | 10.5 |
| CAMPYLOBACTER_FETUS | 48 | 0.0019 | 0.016 | 7.2 |
| LEPTOTRICHIA_BUCCALIS | 49 | 0.0019 | 0.016 | 9.9 |
| PREVOTELLA_INTERMEDIA | 50 | 0.0019 | 0.016 | 4.3 |

Next, to determine the spatial distribution of *Fusobacterium* in these tumors, Applicants performed *Fusobacterium* RNA in-situ hybridization (ISH) analysis was performed on five qPCR-positive primary/metastasis pairs from this cohort (FIGS. 2A-2H and FIGS. 13A-13D). Both biofilm and invasive *F. nucleatum* were observed in primary colorectal cancer (FIGS. 2A-2D). Invasive *F. nucleatum* distribution was highly heterogeneous and focal, found in isolated or small groups of cells with morphology consistent with malignant cells, located close to the lumen and ulcerated regions. *F. nucleatum* was also observed in glandular structures present in the tumor center and invasive margins, but to a lesser extent. In adjacent normal mucosa (when present) *F. nucleatum* was exclusively located in the biofilm. In liver metastasis, *F. nucleatum* was predominantly localized in isolated cells whose histomorphology is consistent with colon cancer cells (FIGS. 2E-2H), although occasional stromal *F. nucleatum* could be observed as well. No *F. nucleatum* was detected in the adjacent residual liver parenchyma.

Figure 3A:
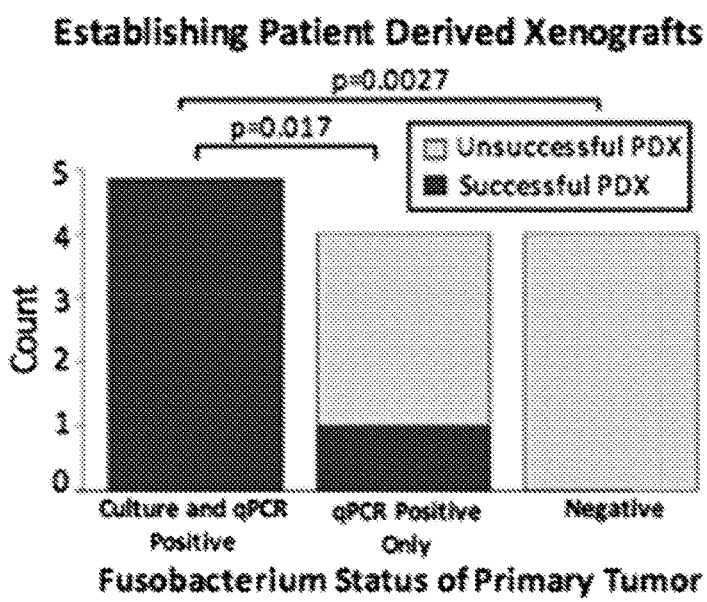
FIGS. 3A-3C: *Fusobacterium* and co-occurring anaerobes persist in colon adenocarcinoma patient derived xenografts.

Given the persistence of viable *Fusobacterium* species in metastatic CRC, Applicants next asked if *Fusobacterium* could persist in colorectal cancer xenografts. To address this question, fresh primary human CRC tumors were subjected to microbial analysis (culture and qPCR) to assess the presence of *Fusobacterium* and were implanted subcutaneously into Nu/Nu mice, to establish patient-derived xenografts (PDXs). All *Fusobacterium*-culture positive CRCs resulted in successful xenografts (FIG. 3A), while all attempts to generate PDXs from *Fusobacterium*-culture negative tumors were unsuccessful (p=0.003). Tumor grade did not appear to significantly influence successful xenograft formation (p=0.1) (FIG. 1A), although we noted a modest association between *Fusobacterium*-cultivability and high-grade tumors in this cohort (n=4/5, p=0.03) (FIG. 11B).

Figure 3B:
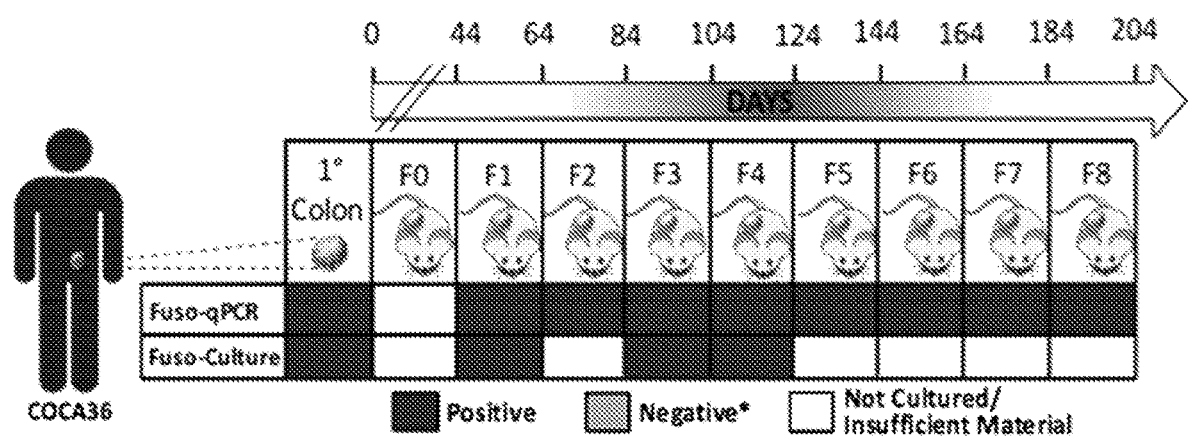
Figure 8:
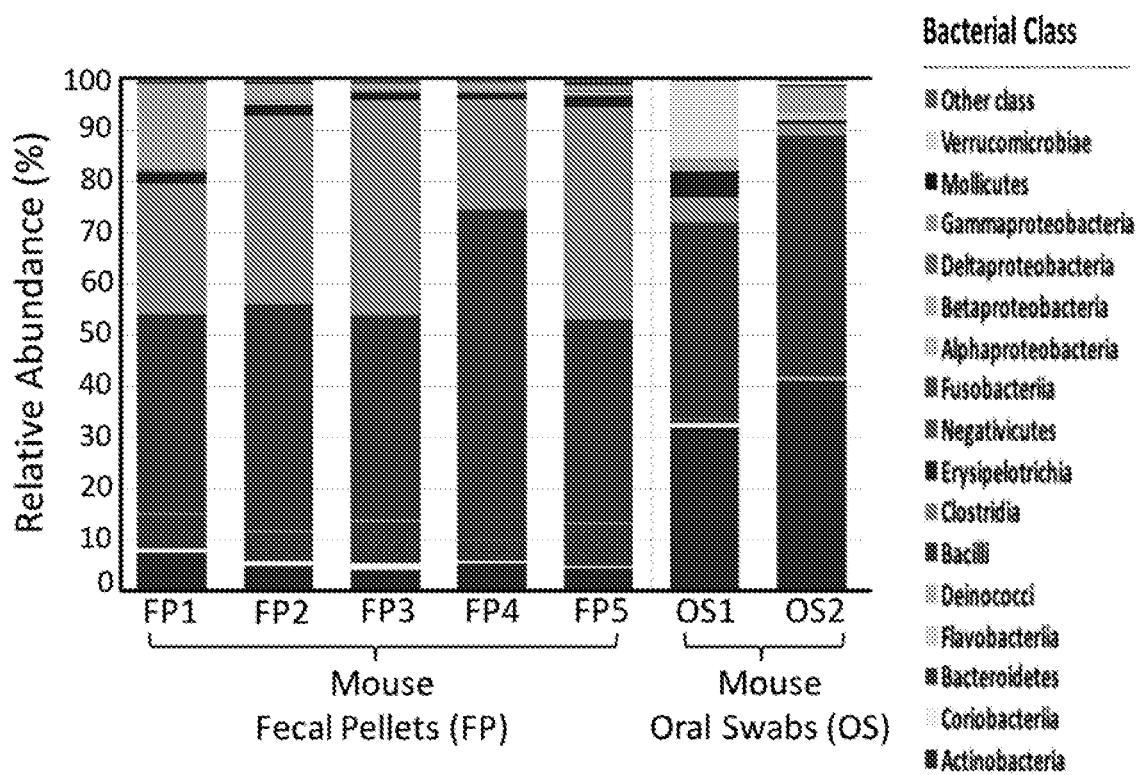
FIG. 8: Fusobacteria are not present in the oral cavity or fecal pellets of Nu/Nu mice in our study. Microbial analysis of murine fecal pellets and oral swabs. Whole genome sequencing and PathSeq analysis of five fecal pellets and two oral swabs from Nu/Nu mice demonstrates that these mice are not carrying *Fusobacterium* in their oral cavity or in their fecal pellets. *Fusobacterium* qPCR also confirmed that the Nu/Nu mice were *Fusobacterium* negative in the lower and upper gastrointestinal tract.

Next, Applicants sought to determine whether *Fusobacterium* would remain viably associated with colorectal cancer xenografts when propagated through multiple generations of mice. A PDX derived from an *F. nucleatum* culture positive CRC (COCA36) was passaged to F8, allowing us to test for the presence of *F. nucleatum* over a period of 29 weeks in vivo. Applicants cultured *F. nucleatum* from this PDX for up to four generations and 124 days in vivo. All xenograft generations, from F1 through F8, were *Fusobacterium* qPCR positive (FIG. 3B). Additionally, Applicants cultured other anaerobic bacteria, including *B. fragilis* and *B. thetaiotaomicron*, from both the primary tumor and PDX. Applicants further cultured *Fusobacterium* from PDXs of two additional patients (Table 4). *Fusobacterium* targeting qPCR and microbiome analysis of fecal pellets and oral swabs from these animals were negative for *Fusobacterium* species (FIG. 8), arguing against the possibility that *Fusobacterium* was arising from the endogenous murine microbiome.

TABLE 4

Fusobacterium-targeted qPCR and culture of primary colorectal tumors, metastases and derived xenografts.

| Tumor | Source | Fusobacterium qPCR |
|---|---|---|
| COCA6 Primary | Colorectal adenocarcinoma | Positive* |
| COCA6 F3 | Colorectal adenocarcinoma PDX | Positive* |
| COCA31 Primary | Colorectal adenocarcinoma | Positive |
| COCA31 F1 | Colorectal adenocarcinoma PDX | Positive |
| COCA38 Primary | Colorectal adenocarcinoma | Positive |
| COCA38 F2 | Colorectal adenocarcinoma PDX | Positive* |
| COCA38 F3 | Colorectal adenocarcinoma PDX | Positive |
| COCA39 Primary | Colorectal adenocarcinoma | Positive* |
| COCA39 F2 | Colorectal adenocarcinoma PDX | Positive |
| COCA39 F3 | Colorectal adenocarcinoma PDX | Positive |
| COCA39 F4 | Colorectal adenocarcinoma PDX | Positive |
| COCA45 Primary | Colorectal adenocarcinoma | Positive* |
| COCA45 F2 | Colorectal adenocarcinoma PDX | Positive |

Retrospective Analysis of Human Metastases from Colorectal Adenocarcinoma

| Tumor | Source | Fusobacterium qPCR |
|---|---|---|
| COCA32 Metastases | Abdominal wall metastases | Positive* |
| COCA32F1 | Abdominal wall metastases PDX | Positive* |
| COCA43 Metastases | Abdominal wall metastases | Positive |
| COCA43F1 | Abdominal wall metastases PDX | Negative |
| COCA68 Metastases | Liver metastases | Positive |
| COCA68 F0 | Liver metastases PDX | Positive |
| COCA74 Metastases | Liver metastases | Positive |

*Fusobacterium culture positive.

Figure 3C:
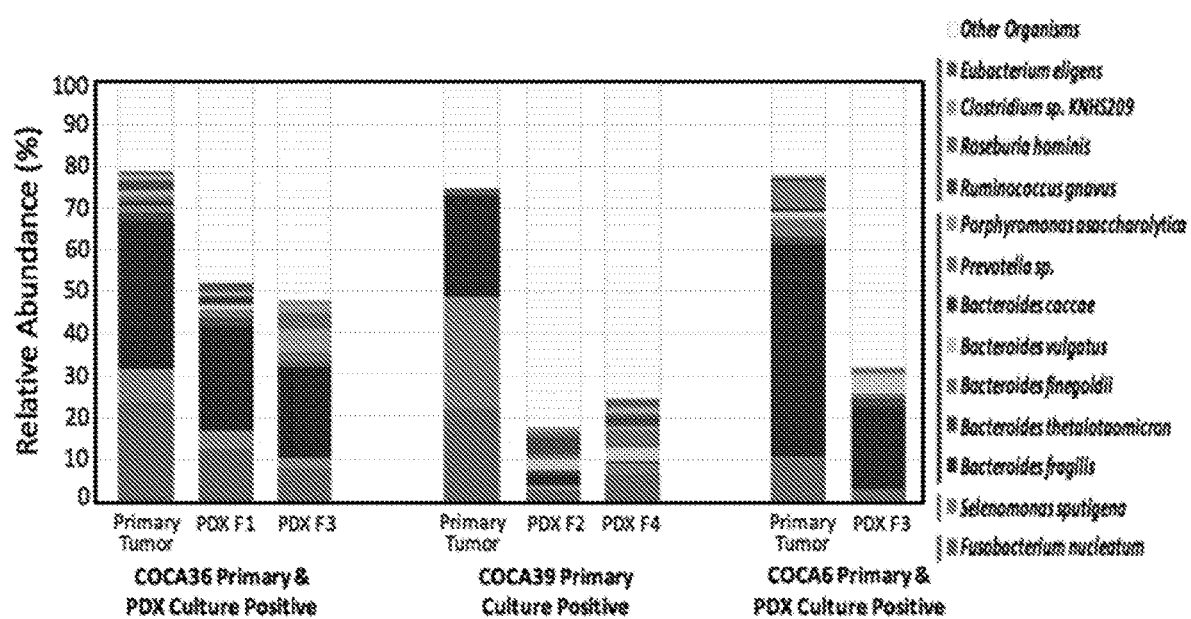
Figure 12:
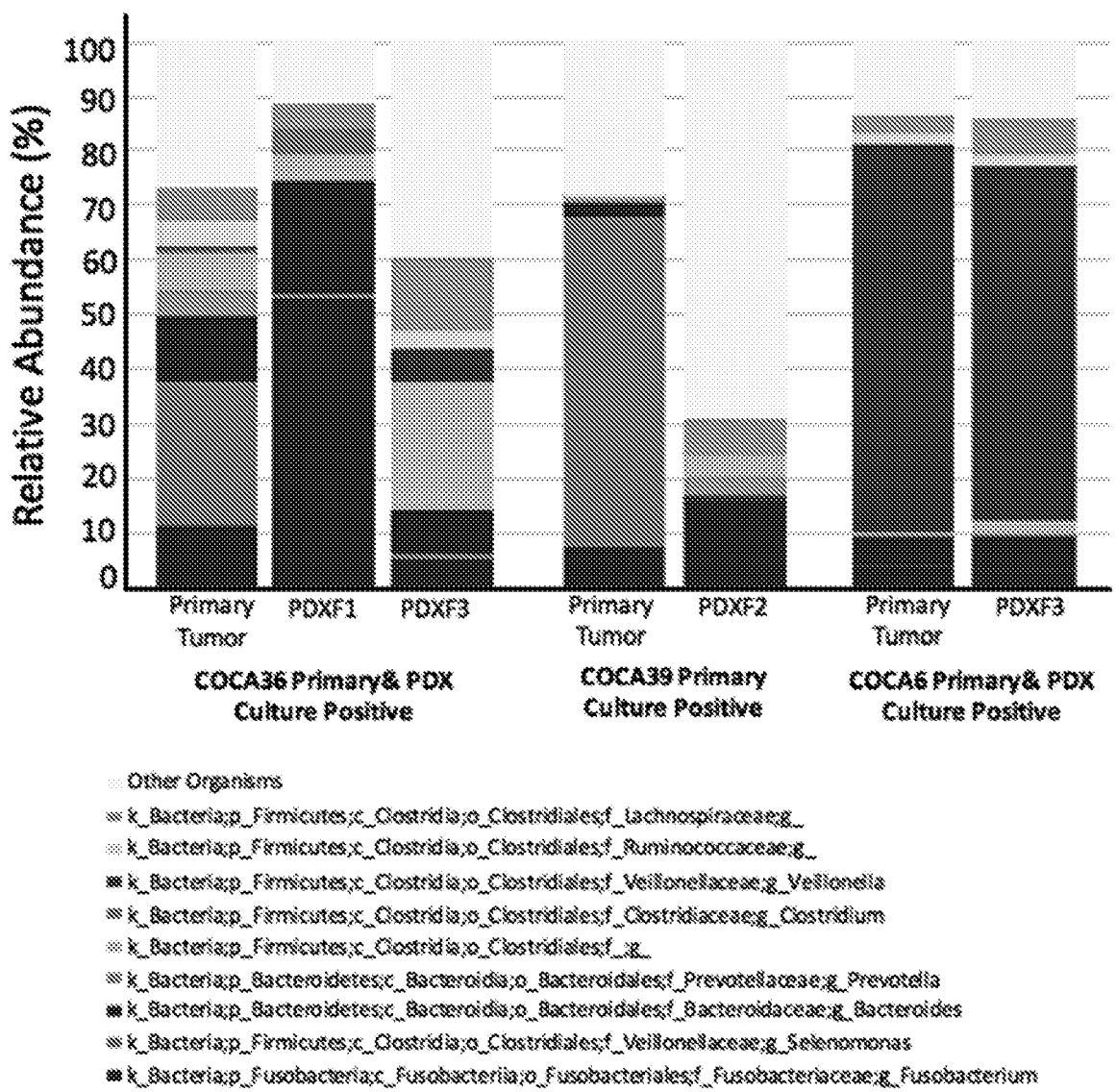
FIG. 12: Bacterial 16s rRNA sequencing demonstrating *Fusobacterium* and co-occurring anaerobes persist in colon adenocarcinoma patient derived xenografts (PDXs). Genus level (OTU_L7) microbial composition of three patient primary colon adenocarcinomas (COCA36, COCA39 and COCA6) and subsequent PDX's from the "xenograft cohort". Bacterial 16s rRNA sequencing was used for microbial identification. For simplicity, only species with >1% relative abundance in the primary tumor and correspond PDX are shown.
Figure 13A:
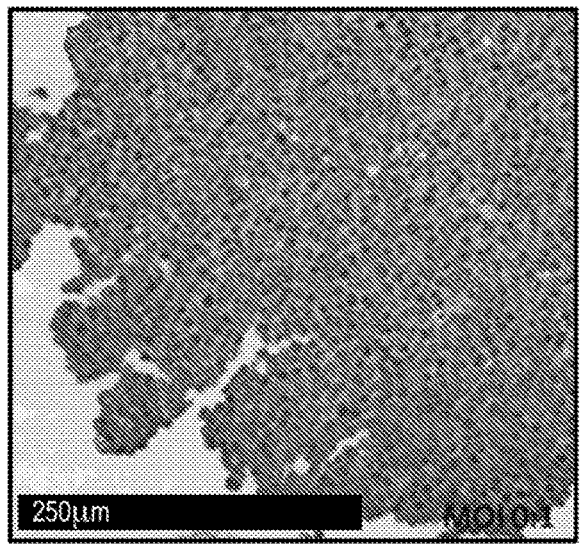
FIGS. 13A-13D: Representative images of RNA ISH detecting *F. nucleatum* spiked in HCT116 cell lines.
Figure 13B:
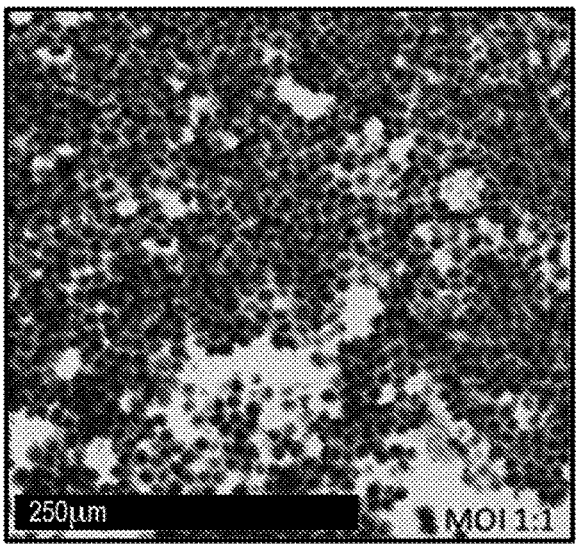
Figure 13C:
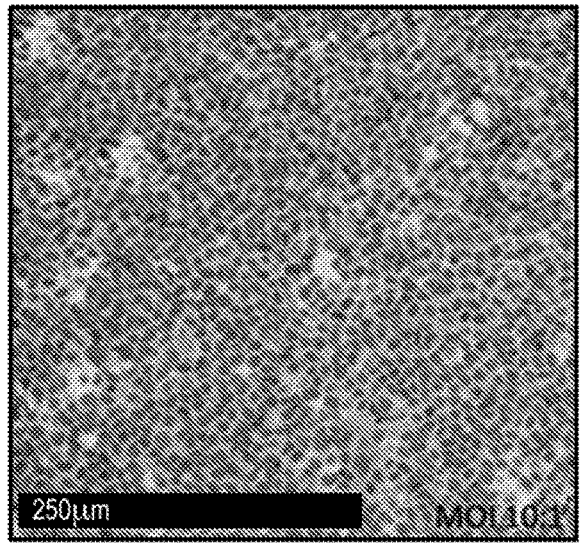
Figure 13D:
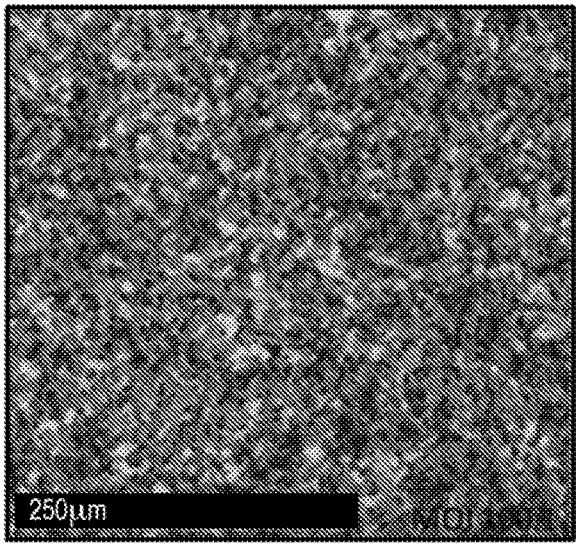

To identify bacteria that are persistently associated with the primary colorectal tumor and derivative xenografts, Applicants carried out unbiased total RNA sequencing followed by PathSeq analysis (Kostic et al., Nat Biotechnol 29, 393-396 (2011)), which revealed that F. nucleatum and other gram-negative anaerobes, including B. fragilis and Selenomonas sputigena. persist in these PDX models for multiple generations (FIG. 3C). Remarkably, the bacteria that persist within the PDX include the genera that Applicants report to persist in distant site metastases to the liver (FIG. 1C) and are enriched in Fusobacterium-associated colorectal cancer from analysis of TCGA data (FIG. 1E). Bacterial 16S rRNA gene sequencing further confirmed the persistence of Fusobacterium and co-occurring anaerobes in these primary colorectal tumors and derived xenografts (FIG. 12).

Applicants then assessed if the primary tumor and PDX F. nucleatum isolates were capable of invading human colon cancer cells. Transmission electron microscopy (TEM) showed that F. nucleatum isolates from both primary CRCs and PDXs were invasive when incubated with HT-29 and HCT-116 colon cancer cell lines. Upon infection with F. nucleatum, Applicants saw evidence of bacterial cells within vesicle-like structures in the cancer cell (FIGS. 4A-4C). Interestingly, Applicants also see evidence of bacterial adhesion and invasion in the respective patient xenograft tissue (FIG. 4D).

Figure 5A:
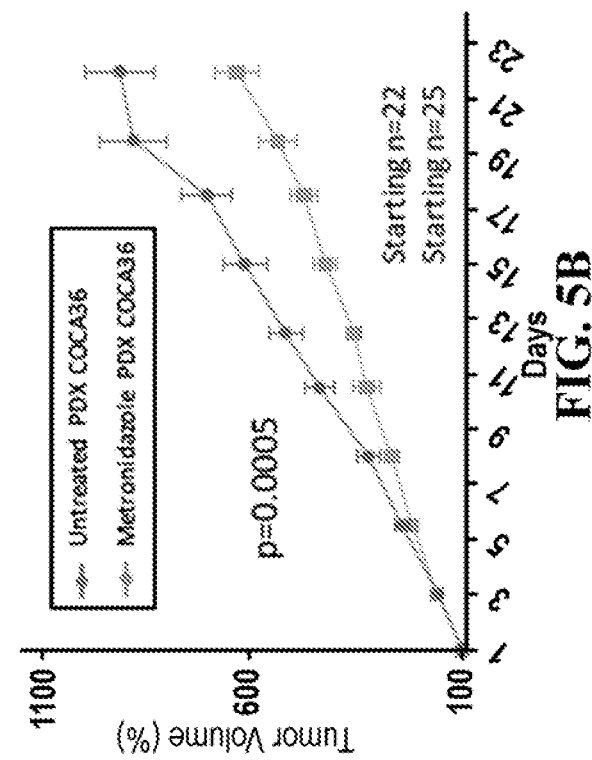
FIGS. 5A-5D: Treatment of *Fusobacterium* colonized PDX with metronidazole reduces tumor growth in vivo.
Figure 15:
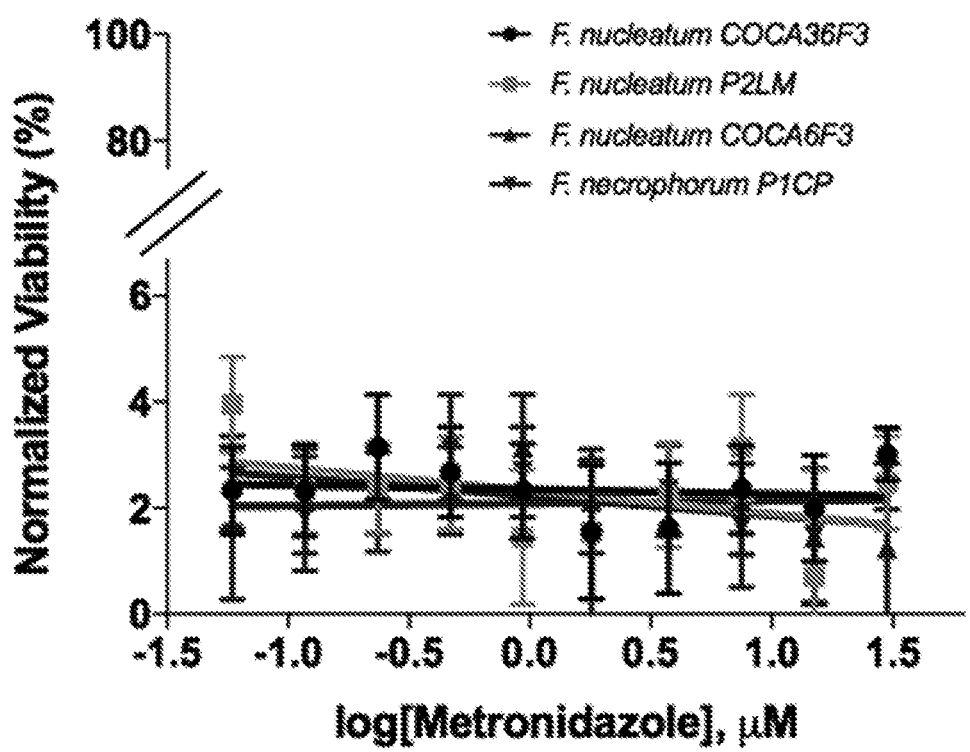
FIG. 15: Metronidazole susceptibility testing with four *Fusobacterium* clinical isolates. Test range: 0.058-30 µM (0.01-5.13 µg/ml). The center bar represents the mean and the error bars are the standard error of the mean (SEM).

Finally, Applicants asked whether treatment of Fusobacterium-positive colorectal cancer xenografts with an antibiotic that targets Fusobacterium species would affect tumor growth. A recent study reported that infection with F. nucleatum increased the growth rate of tumor xenografts derived from CRC cell lines in vivo (Yang et al., Gastroenterology, (2016)). Similar to previous findings from Applicants' group demonstrating an NF-κB-driven pro-inflammatory response in Fusobacterium associated human colorectal cancers (Kostic et al., Cell host & microbe 14, 207-215 (2013)), this group reports that F. nucleatum initially activates TLR-4 signaling, promoting subsequent NF-κB activation (Yang et al., Gastroenterology, (2016)). Fusobacteria are reported to be highly sensitive to metronidazole (Lofmark et al., Clinical Infectious Diseases 50, S16-S23 (2010)). Applicants confirmed that F. nucleatum isolates from the PDX are sensitive to metronidazole (minimum inhibitory concentration <0.016 µg/ml) (FIGS. 14 and 15). To assess whether metronidazole is generally toxic to colorectal carcinomas, Applicants treated Fusobacterium-free xenografts, derived from HT-29 colon adenocarcinoma cells, with metronidazole and observed no significant decrease in tumor growth ($p>0.05$ at all timepoints measured) (FIG. 5A). Ideally, a Fusobacterium-negative PDX would have been included as a control. However, none of the Fusobacterium-negative CRC tumors tested generated successful PDXs (FIG. 3A), which prevented this comparison.

Figure 5B:
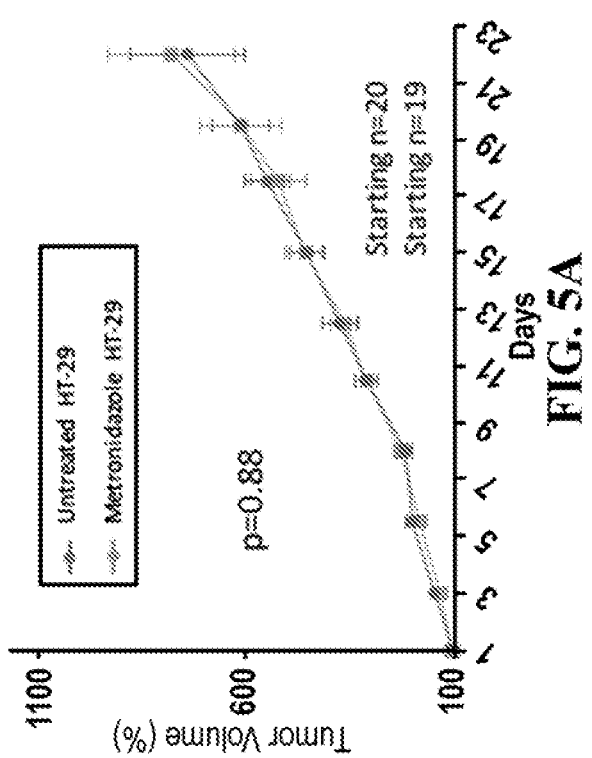
Figure 5C:
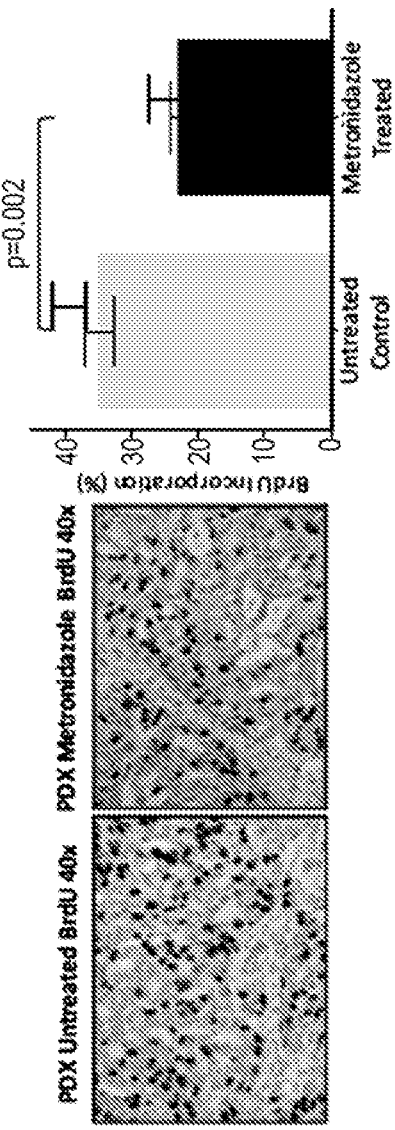
Figure 5D:
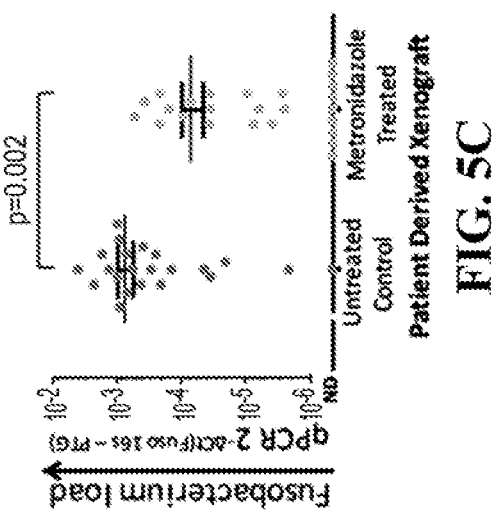

Upon oral administration of metronidazole to mice bearing Fusobacterium-positive PDXs, Applicants observed a statistically significant decrease in tumor growth, compared to PDXs in mice treated with vehicle ($p=0.0005$) (FIG. 5B). Treatment with metronidazole was associated with a significant decrease in Fusobacterium load in the tumor tissue ($p=0.002$) (FIG. 5C), along with a significant reduction in tumor cell proliferation ($p=0.0015$) (FIG. 5D).

In summary, Applicants have shown that 1) Fusobacterium is persistently associated with colorectal cancer in distant metastases from human cancers, and survives through multiple generations of xenografts in mice, 2) Fusobacterium is associated with other co-occurring anaerobes, including B. fragilis and S. sputigena, 3) CRC-derived Fusobacterium can invade colon cancer cell lines, and Applicants observe evidence of bacterial invasion in xenografts, 4) Treatment of Fusobacterium-enriched PDXs with the Fusobacterium-killing antibiotic, metronidazole, decreases Fusobacterium load, leads to decreased cancer cell proliferation, and reduces tumor growth.

The persistence of Fusobacterium in distant sites and xenografts provides a distinct view of the cancer population in metastasis. Applicants hypothesize that invasive Fusobacterium strains travel with primary tumor cells to distant sites and establish colonization in metastases. This observation makes metastasis a property of a cancer community including the microbiome rather than a property of a single cancer cell.

The continued association of Fusobacterium species with human tumors appears to be a critical component of the tumor microenvironment. This observation extends beyond Fusobacterium to include a range of co-occurring gram-negative anaerobes such as B. fragilis and S. sputigena, suggesting that the tumor microbiome is a persistent feature of a given cancer, rather than a property of its anatomical location. Noting F. nucleatum's role as a bridging organism in biofilm formation as shown within the oral cavity (Kolenbrander et al., Infection and immunity 57, 3194-3203 (1989); Kolenbrander et al., Journal of bacteriology 175, 3247-3252 (1993)), it is plausible that Fusobacteria provide a physical and/or metabolic scaffold for the broader microbial community in colorectal cancer evolution (Warren et al., Microbiome 1, 16 (2013)).

Applicants' results suggest the potential for further studies of modulating the microbiome in the treatment of colorectal carcinomas. Given the long experience with and relative safety of antibiotics, it is worth evaluating what further experimental data are required to initiate clinical trials of antibiotic treatment in conjunction with chemotherapeutic treatment for Fusobacterium-positive colorectal cancers. Supporting the potential for targeting tumor associated microbes in colon cancer treatment, Sears and colleagues (DeStefano Shields et al., The Journal of infectious

*diseases* 214, 122-129 (2016)) recently demonstrated a reduction in tumorigenesis by treating ETBF induced murine colonic tumors with the antibiotic cefoxitin. Some concerns could include the impact of broad spectrum antibiotics on intestinal microbes and the possibility of developing opportunistic infections.

In the long run, given that metronidazole targets a range of anaerobic bacteria including co-occurring anaerobes that persist with *Fusobacterium*, it could be valuable to develop and test a *Fusobacterium*-specific antimicrobial agent to determine if the growth effect of metronidazole treatment is dependent primarily on *Fusobacterium*, or due to a range of co-occurring anaerobes within the tumor. Applicants' results provide a foundation for developing targeted approaches, perhaps with probiotic bacterial strains or selective small molecules, against key microbes associated with CRC.

Finally, Applicants ask in conclusion, does *Fusobacterium* cause cancer, is it an innocent bystander, or is its presence a consequence of cancer? Applicants' view at present is that *Fusobacterium* could be liable for causing colorectal cancer in a civil suit, which requires a preponderance of the evidence. However, Applicants believe that *Fusobacterium* would currently be found not guilty of causing colorectal cancer in a criminal case, which requires evidence beyond a reasonable doubt.

Methods

Patient Specimen Collection

For the analysis of *Fusobacterium*'s persistence in distant site metastasis Applicants analyzed formalin fixed, paraffin embedded (FFPE) sections of primary colorectal tumors and matched liver metastasis from 101 patients, and snap frozen tissue of primary colorectal tumors and matched liver metastasis from an additional eleven patients from Vall d'Hebron University Hospital, Barcelona, Catalonia, Spain.

For the analysis of *Fusobacterium*'s persistence in patient derived xenografts Applicants collected 13 fresh colorectal tissues from Brigham and Women's Hospital, Boston, MA, 02115, USA. Retrospectively, colorectal metastasis (abdominal wall n=2 and liver n=2), collected from Brigham and Women's Hospital from four patients that established patient derived xenografts, were tested for the presence of *Fusobacterium*. An additional 40 fresh colorectal tissues were collected from the Brigham and Women's Hospital, Boston, MA, 02115, USA, for microbial analysis but were not implanted into mice for xenograft studies. Written informed consent was obtained from all patients, and the study was approved by the Institutional Review Boards of all participating institutions.

DNA and RNA Extraction

DNA was extracted from FFPE samples using the QIAamp DNA FFPE Tissue Kit (Qiagen Inc., USA), from fresh or snap frozen tissues and oral swabs using the DNeasy Blood & Tissue Kit (Qiagen Inc., USA), from bacterial cells using the QIAamp DNA Mini Kit (Qiagen Inc., USA) and RNA was extracted from tissue using the RNeasy Mini Kit (Qiagen Inc., USA), all according to manufactures instructions. DNA was extracted from murine fecal samples using an isopropanol DNA precipitation method as described previously (https://www.qiagen.com/us/resources/molecular-biology-methods/dna/).

Quantitative PCR (qPCR)

A custom TaqMan primer/probe set was used to amplify *Fusobacterium* species DNA (Integrated DNA technologies, CA) as previously described (28). The cycle threshold (Ct) values for *Fusobacterium* species were normalized to the amounts of human genomic DNA in each reaction by using a primer and probe set for the prostaglandin transporter (PGT) reference gene, and the fold difference ($2^{-\Delta Ct}$) in *Fusobacterium* load in tumor tissue was calculated as described before (8). Each reaction contained 100 ng of genomic DNA and was assayed in triplicate in 20 µL reactions containing 1× final concentration TaqMan Universal Master Mix (Applied Biosystems) and each TaqMan Gene Expression Assay (Applied Biosystems), in a 96-well optical PCR plate. Amplification and detection of DNA was performed with the ABI 7300 Real-Time PCR System (Applied Biosystems) using the following reaction conditions: 10 min at 95° C. and 42 cycles of 15 s at 95° C. and 1 min at 60° C. Cycle thresholding (Ct) was calculated using the automated settings (Applied Biosystems). The primer and probe sequences for each TaqMan Gene Expression Assay were as follows (SEQ ID. 1-6): *Fusobacterium* species forward primer, 5'-AAGCGCGTCTAGGTGGT-TATGT-3'; *Fusobacterium* species reverse primer, 5'-TGTAGTTCCGCTTACCTCTCCAG-3'; *Fusobacterium* species FAM probe, 5'-CAACGCAATACAGAGTTGAG-3'. PGT forward primer, 5'-ATCCCCAAAGCACCTGGTTT-3'; PGT reverse primer, 5'-AGAGGCCAAGAT AGTCCTGGTAA-3'; PGT FAM probe, 5'-CCATC-CATGTCCTCATCTC-3'.

DNA and RNA Library Construction for Next-Generation Sequencing

DNA and RNA from specimens were quantified using the NanoDrop apparatus along with the 2100 Bioanalyzer system (Agilent) prior to library construction. DNA libraries were prepared using the Nextera XT DNA Library Preparation Kit (Illumina) and total RNA sequencing libraries were prepared using the NEBNext® Ultra™ Directional RNA Library Prep Kit for Illumina® (New England Biolabs) per manufacturer's instructions. Samples were pooled following library quantification using the KAPA Library Quantification Kits for Next-Generation Sequencing (KAPA Biosystems) and library insert size visualization using the 2100 Bioanalyzer system (Agilent). RNAseq libraries from tissue samples were sequenced on the Illumina HiSeq2500 platform in "Rapid Run" mode using 100 bp paired end sequencing, with 7-8 samples per lane, with an average of 41 million reads per sample. DNA libraries from murine oral swabs and fecal pellets were sequenced on the Illumina HiSeq2500 platform in "Rapid Run" mode using 100 bp paired end sequencing, with an average of 10.2 million reads per sample. Bacterial whole genomes were sequenced using the MiSeq platform with MiSeq Reagent Kit v2 (300 cycles), 150 bp paired end sequencing with an average of 60× coverage.

Bacterial Culture from Tissue

Snap frozen or fresh tumor sections (ranging from 1-5 $mm^3$) were placed in to 500 µL of pre-warmed tryptic soya broth (TSB), the tissue was agitated and gently broken up using a sterile 16G1/2 needle followed by a 22G1/2 needle (PrecisionGlide, BD).

Fifty microliter aliquots of this suspension were directly spread onto fastidious anaerobe agar (FAA) plates (Neogen Acumedia, Fisher Scientific, USA) supplemented with 7% defibrinated horse blood (DHB) (Lampire Biological Laboratories, Fisher Scientific, USA). If the tissue was resected from the colon or rectum the 500 µL suspension was split in half and fifty microliter aliquots of this suspension were also spread on selective agar (JVN), FAA+7% DHB plates with josamycin, vancomycin and norfloxacin, at 3, 4 and 1 µg/ml, respectively (Sigma Aldrich, USA). Plates were incubated at 37° C. for up to 14 days under anaerobic conditions (AnaeroGen Gas Generating Systems, Oxoid), with a positive and negative control plate.

Plates were inspected every 2 days for growth and AnaeroGen™ gas packs (Oxoid), were changed. Colonies were picked and streak-purified on FAA+7% DHB plates. Single colonies were examined by Gram stain under a light microscope, looking for gram-negative slender rods or needle-shaped cells characteristic of *F. nucleatum*. Colony PCR was also carried out on selected bacterial colonies. Briefly, pure colonies of interest were picked using a 1 µL sterile loop and inoculated in to 30 µL of sterile water, the bacterial suspension was then boiled for 20 minutes at 98° C. and cooled to 4° C. Two microliters of the resulting colony DNA was used in a 20 µL PCR reaction (REDTaq Readymix, Sigma Aldrich, USA) with the universal bacterial primers, 342F and 1492R to amplify approximately 1.15 kb of the bacterial 16s rRNA gene as described previously (29). These colony PCR products were sent for Sanger sequencing and BLASTn analysis of obtained traces was used to confirm bacterial species identity. Bacterial species of interest were suspended in TSB with 40% glycerol and stored at −80° C.

Antibiotic Sensitivity Testing (E-Test) for Fusobacterium Strains

A 1 McFarland solution, in TSB, was prepared from *Fusobacterium* strains grown for 24-48 hours on FAA under anaerobic conditions. Using a sterile cotton swab, each *Fusobacterium* strain were inoculated onto antibiotic free blood agar (FAA) and E-test strip (bioMérieux) for Metronidazole (MZ), Clindamycin (CM), Cefoxitin (FX) and Imipenem (IP) were incubated for up to 72 hours and sensitivity checked after 48 hours. Each sensitivity assay was conducted in triplicate. An FAA blood plate inoculated with each *Fusobacterium* strain, but without the E-test strip, was used as a growth control.

Establishment of Patient Derived Xenografts

This analysis was conducted on tissue for which signed informed consent was previously obtained from the patient undergoing surgery, according to an Institutional Review Board-approved research protocol. Fresh primary colon cancer biopsies were first incubated in an antibiotic cocktail of penicillin/streptomycin/amphotericin B/Ciprofloxacin for 1-2 hours to prevent abscess formation in vivo and then tumors are cut into approximately 8 mm$^3$ pieces of tissue and implanted into the flanks of 5 weeks old, female nude mice (Nu/Nu; Taconic). Mice are then housed in a pathogen free environment for up to 6 months to determine if primary PDX are established. When the xenografts reached ~200 mm$^3$ mice were sacrificed, tumors harvested and serially passaged as subcutaneous implants of tumor fragments approximately 2-3 mm in diameter. At each passage tissues were cryopreserved in Bambanker cell freezing media (Wako Chemicals USA) and/or snap frozen in liquid nitrogen and stored at −80° C. Snap frozen tissue was used for RNA and DNA extraction. When possible fresh tissue was used for microbial culture attempts.

In Vivo Metronidazole Trial

Animals bearing tumors (with volumes <250 mm$^3$) were randomized into statistically identical cohorts and treated with 100 mg/kg/day of metronidazole (Sigma Aldrich, USA), (suspension in 0.5% methylcellulose) or with the vehicle alone (0.5% methylcellulose) by oral gavage, daily, for approximately 3 weeks.

For HT-29 cell line xenograft experiments, approximately 1×10$^6$ HT29 cells were suspended in PBS, mixed 1:1 with Matrigel (BD Biosciences), and injected subcutaneously into the flanks of nude mice (Nu/Nu; Taconic) in a final volume of 100 µL. Following 10-14 days post implantation, mice were randomized into statistically identical cohorts and treated with 100 mg/kg/day of metronidazole (suspension in 0.5% methylcellulose) or with vehicle alone by oral gavage daily for approximately 3 weeks.

Nu/nu mice were raised in the specific-pathogen-free (SPF) conditions with autoclaved food and water. For both patient and HT-29 cell derived xenografts, tumor size was measured by caliper every Monday, Wednesday and Friday each week. Tumor volume was calculated using the formula: Volume=0.5×L×W$^2$ and growth rate was measured by calculating the percentage increase in volume. Tumor measurements were carried out in a blinded approach. Mouse body weight was recorded every 3 to 7 days. Mice were euthanized when the tumor diameter reached 2 cm or following the 3 weeks of drug treatment. Tissues were cryopreserved in Bambanker cell freezing media (Wako Chemicals USA) or snap frozen in liquid nitrogen and stored at −80° C. PDX experiments were performed with 22 (untreated group) and 24 (treated group) mice at timepoint zero, over three independent trials. HT-29 derived xenograft experiments were performed with 20 (untreated group) and 19 (treated group) mice at timepoint zero, over two independent trials. All procedures were performed according to protocols approved by the Institutional Animal Care and Use Committees of the Dana-Farber Cancer Institute.

In Vivo Bromodeoxyuridine (Brdu) Incorporation Assay

Bromodeoxyuridine (BrdUrd) solution (10 mg/mL, 0.2 mL/mouse) was administered via intraperitoneal injection 16 hours after the last dose of metronidazole or vehicle. After 2 additional hours, mice were sacrificed and tumors were fixed in 10% formalin for immunohistochemistry (IHC) analysis. A total of 6 animals per arm, that were treated with metronidazole or the vehicle for three weeks were randomly selected, over two independent trials, for BrdU incorporation analysis.

IHC Analysis

IHC was performed on 4-µm sections of formalin-fixed paraffin-embedded samples. Tissue sections were deparaffinized and rehydrated, and antigen retrieval was performed in 10 mmol/L citrate buffer (pH 6.0) in a 750 W microwave oven at 199° C. for 30 minutes for BrdU staining, BrdU primary antibody (BD Biosciences, #347580) was added at a dilution of 1:100 and incubated for 1 hour at room temperature. Sections were further processed with horseradish peroxidase-conjugated secondary antibody. The reaction was detected by 3,3-diaminobenzidine and hematoxylin staining. Images were obtained with an Olympus CX41 microscope and QCapture software (QImaging).

Statistical Analysis

Comparisons between groups were made using the Welch two-tailed unpaired t test (unequal variances t-test) in R.

Comparisons between group proportions were made using the z score test for two population proportions (two-tailed).

The relationships between *Fusobacterium* culture and metastatic colorectal tumors was analyzed using Fisher's exact test.

In all cases, P values were two-tailed and P values less than 0.05 were designated as significantly different Cell Culture The CRC cell lines (HCT116 and HT29) were obtained from the American Type Culture Collection (ATCC, Manassas, VA, USA). All of the cell lines were cultured in appropriate conditions as recommended by ATCC.

Epithelial Cell Invasion Transmission Electron Micrograph (Tem) Analysis

The *F. nucleatum* isolates from primary colon tumor (COCA36) and derived xenograft (COCA36F3) were grown on JVN agar for 30 hours under anaerobic conditions as described above. Bacterial culture suspensions were normalized for cell number using predetermined McFarland standards. HT-29 and HCT-116 cells, at 80% confluency in 6 well plates, were infected with *F. nucleatum* at a multiplicity of infection (MOI) of 100:1 (bacterial cells: epithelial cells). Following infection, cells were maintained for 2.5 h at 37° C., 5% $CO_2$, after which cell media was removed, the cells were gently washed twice with PBS and were then trypsinized and again gently washed twice with PBS. The pellet was collected and stored in 3% EM grade glutaraldehyde (Fisher Scientific) at 4° C. overnight. Sections were prepared for TEM analysis.

Bacterial Genome Assembly and Analysis

Bacterial genomes were assembled using the Velvet assembly tool (30) and a range of k-mer values from 39 to 99 (which determine the minimum read overlap) was tested to find the optimum hash length for assembly of the data. Assembled bacterial genomes were annotated and compared using both RAST (31) and IMG/ER (32). Genomes were compared using the Average Nucleotide Identity (ANI) program in IMG/ER and Kostas Lab online ANI tool (http://enve-omics.ce.gatech.edu). The parameters for the Kostas Lab online ANI tool were set to default (alignment options: minimum length 700 bp, minimum identity 70%, minimum alignment 50. Fragment options: step size 200 bp) with the exception of the window size which was set to 300 bp. The CGView Server was used for a comparative analysis and to generate circular genomes of bacterial strains (33).

Microbial Detection in Whole Genome Sequencing (WGS) and RNA Sequencing Datasets.

The PathSeq (20, 37) algorithm was used to perform computational subtraction of human reads, followed by alignments of residual reads to human reference genomes/transcriptomes and microbial reference genomes (which include bacterial, viral, archaeal, and fungal sequences—downloaded from NCBI in October, 2015). These alignments resulted in taxonomical classification of reads into bacterial, viral, archaeal, and fungal sequences in whole genome sequencing (WGS) and RNA sequencing (RNASeq) data.

Briefly, PathSeq is used to remove low quality reads followed by subtraction of human reads by mapping reads to a database of human genomes (downloaded from NCBI in November 2011) using BWA (34) (Release 0.6.1, default settings), MegaBLAST (Release 2.2.25, cut-off E-value $10^{-7}$, word size 16) and BLASTN (35) (Release 2.2.25, cut-off E-value $10^{-7}$, word size 7, nucleotide match reward 1, nucleotide mismatch score −3, gap open cost 5, gap extension cost 2). Only sequences with perfect or near perfect matches to the human genome were removed in the subtraction process. In addition, low complexity and highly repetitive reads were removed using Repeat Masker (version open-3.3.0, libraries dated 2011 Apr. 19).

Taxonomic classification is performed by residual reads alignment using MegaBLAST (Release 2.2.25, cut-off E-value $10^{-7}$, word size 16) to a database of bacterial sequences and followed by BLASTN (Release 2.2.25, cut-off E-value $10^{-7}$, word size 7) to human reference gnome and microbial reference genomes.

Following the taxonomic classification of non-human DNA sequencing reads the relative abundance value for each bacterial organism is calculated as follows by using reads that maps with >=90% sequence identity and >=90% query coverage. Classifications were performed at the domain, then phylum, then genus, then species level, requiring unique alignments (i.e., reads with equivalent E-values to multiple taxa were removed from analysis).

In the case of WGS data, species level relative abundance (RA) for each organism was calculated as follows: relative abundance of a given organism in a sample=(number of unique alignment positions in genome×1,000,000)/(number of total aligned bacterial reads×genome size). The RA values were then per-sample normalized such that the total relative abundance for each sample sums to one.

In the case of RNA sequencing data, species level relative abundance (RA) for each organism was calculated as follows: relative abundance of a given organism in a sample= ((number of reads aligned to a given organism/number of human reads in the sample)×1,000,000). The RA values were then per-sample normalized such that the total relative abundance for each sample sums to one.

Comparative Microbial Analysis

Following PathSeq analysis of colon adenocarcinoma (COAD) samples from TCGA, samples were subset into *Fusobacterium* 'High' (>1% RA, n=110, median RA=5.72%, mean RA=7.7%) and *Fusobacterium* 'Low/Negative' (RA<1%, n=325, median RA=0.06%, mean RA=0.16%) tumors based upon *F. nucleatum* relative abundance. Comparative analysis was carried out between these two groups using LEfSe (36) (online version available on August 2016), using default parameters, except the linear discriminant score (LDA score) was increased to >=3.5 to identify significant bacterial organisms enriched or depleted in the *F. nucleatum* "High" COAD group. The GENE-E analysis tool (https://software.broadinstitute.org/GENE-E/), marker selection analysis, was used to further identify co-occurring microbes in the *F. nucleatum* "High" v's *F. nucleatum* "Low/Negative" COAD samples and to confirm LEfSe results (Table 3).

References

1. R. F. Schwabe, C. Jobin, The microbiome and cancer. *Nat Rev Cancer* 13, 800-812 (2013).
2. M. E. Hope, G. L. Hold, R. Kain, E. M. El-Omar, Sporadic colorectal cancer—role of the commensal microbiota. *FEMS Microbiol Lett* 244, 1-7 (2005).
3. I. R. Rowland, The role of the gastrointestinal microbiota in colorectal cancer. *Curr Pharm Des* 15, 1524-1527 (2009).
4. L. Yang, Z. Pei, Bacteria, inflammation, and colon cancer. *World J Gastroenterol* 12, 6741-6746 (2006).
5. S. Wu et al., A human colonic commensal promotes colon tumorigenesis via activation of T helper type 17 T cell responses. *Nat Med* 15, 1016-1022 (2009).
6. J. C. Arthur et al., Intestinal inflammation targets cancer-inducing activity of the microbiota. *Science* 338, 120-123 (2012).
7. A. D. Kostic et al., Genomic analysis identifies association of *Fusobacterium* with colorectal carcinoma. *Genome research* 22, 292-298 (2012).
8. M. Castellarin et al., *Fusobacterium nucleatum* infection is prevalent in human colorectal carcinoma. *Genome research* 22, 299-306 (2012).
9. T. Tahara et al., *Fusobacterium* in colonic flora and molecular features of colorectal carcinoma. *Cancer research* 74, 1311-1318 (2014).
10. A. N. McCoy et al., *Fusobacterium* is associated with colorectal adenomas. *PloS one* 8, e53653(2013).
11. L. Flanagan et al., *Fusobacterium nucleatum* associates with stages of colorectal neoplasia development, colorectal cancer and disease outcome. *European journal of* clinical microbiology & infectious diseases: official publication of the European Society of Clinical Microbiology 33, 1381-1390 (2014).
12. Y. Y. Li et al., Association of *Fusobacterium nucleatum* infection with colorectal cancer in Chinese patients. *World journal of gastroenterology* 22, 3227-3233 (2016).
13. M. Ito et al., Association of *Fusobacterium nucleatum* with clinical and molecular features in colorectal serrated pathway. *International journal of cancer* 137, 1258-1268 (2015).
14. K. S. Viljoen, A. Dakshinamurthy, P. Goldberg, J. M. Blackburn, Quantitative profiling of colorectal cancer-associated bacteria reveals associations between *Fusobacterium* spp., enterotoxigenic *Bacteroides fragilis* (ETBF) and clinicopathological features of colorectal cancer. *PloS one* 10, e0119462 (2015).
15. K. Mima et al., *Fusobacterium nucleatum* in colorectal carcinoma tissue and patient prognosis. *Gut*, (2015).
16. K. Mima et al., *Fusobacterium nucleatum* and T Cells in Colorectal Carcinoma. *JAMA oncology* 1, 653-661 (2015).
17. A. D. Kostic et al., *Fusobacterium nucleatum* potentiates intestinal tumorigenesis and modulates the tumor-immune microenvironment. *Cell host & microbe* 14, 207-215 (2013).
18. C. Gur et al., Binding of the Fap2 protein of *Fusobacterium nucleatum* to human inhibitory receptor TIGIT protects tumors from immune cell attack. *Immunity* 42, 344-355 (2015).
19. J. Abed et al., Fap2 Mediates *Fusobacterium nucleatum* Colorectal Adenocarcinoma Enrichment by Binding to Tumor-Expressed Gal-GalNAc. *Cell host & microbe* 20, 215-225 (2016).
20. A. D. Kostic et al., PathSeq: software to identify or discover microbes by deep sequencing of human tissue. *Nat Biotechnol* 29, 393-396 (2011).
21. N. Cancer Genome Atlas, Comprehensive molecular characterization of human colon and rectal cancer. *Nature* 487, 330-337 (2012).
22. Y. Yang et al., *Fusobacterium nucleatum* Increases Proliferation of Colorectal Cancer Cells and Tumor Development in Mice by Activating TLR4 Signaling to NFkappaB, Upregulating Expression of microRNA-21. *Gastroenterology*, (2016).
23. S. Lofmark, C. Edlund, C. E. Nord, Metronidazole Is Still the Drug of Choice for Treatment of Anaerobic Infections. *Clinical Infectious Diseases* 50, S16-S23 (2010).
24. P. E. Kolenbrander, R. N. Andersen, L. V. Moore, Coaggregation of *Fusobacterium nucleatum*, *Selenomonas flueggei*, *Selenomonas infelix*, *Selenomonas noxia*, and *Selenomonas sputigena* with strains from 11 genera of oral bacteria. *Infection and immunity* 57, 3194-3203 (1989).
25. P. E. Kolenbrander, J. London, Adhere today, here tomorrow: oral bacterial adherence. *Journal of bacteriology* 175, 3247-3252 (1993).
26. R. L. Warren et al., Co-occurrence of anaerobic bacteria in colorectal carcinomas. *Microbiome* 1, 16 (2013).
27. C. E. DeStefano Shields et al., Reduction of Murine Colon Tumorigenesis Driven by Enterotoxigenic *Bacteroides fragilis* Using Cefoxitin Treatment. *The Journal of infectious diseases* 214, 122-129 (2016).
28. F. E. Martin, M. A. Nadkarni, N. A. Jacques, N. Hunter, Quantitative microbiological study of human carious dentine by culture and real-time PCR: association of anaerobes with histopathological changes in chronic pulpitis. *J Clin Microbiol* 40, 1698-1704 (2002).
29. D. Lane, 16S/23S rRNA sequencing. *Nucleic acid techniques in bacterial systematics*, 125-175(1991).
30. D. R. Zerbino, E. Bimey, Velvet: algorithms for de novo short read assembly using de Bruijn graphs. *Genome research* 18, 821-829 (2008).
31. R. K. Aziz et al., The RAST Server: rapid annotations using subsystems technology. *BMC Genomics* 9, 75 (2008).
32. V. M. Markowitz et al., IMG ER: a system for microbial genome annotation expert review and curation. *Bioinformatics* 25, 2271-2278 (2009).
33. J. R. Grant, P. Stothard, The CGView Server: a comparative genomics tool for circular genomes. *Nucleic Acids Res* 36, W181-W184 (2008).
34. H. Li, R. Durbin, Fast and accurate short read alignment with Burrows-Wheeler transform. *Bioinformatics* 25, 1754-1760 (2009).
35. S. F. Altschul et al., Gapped BLAST and PSI-BLAST: a new generation of protein database search programs. *Nucleic Acids Res* 25, 3389-3402 (1997).
36. N. Segata et al., Metagenomic biomarker discovery and explanation. *Genome Biol* 12, R60 (2011).
37. https://github.com/ChandraPedamallu/PathSeq Example 2: Compound Screen to Identify Compounds that Inhibit the Growth of *Fusobacterium*

A goal is to identify compounds that selectively inhibit the growth of patient colorectcal cancer isolates of *Fusobacterium*. A pilot screen containing 1,846 compounds (in duplicate), at [32 μM] was carried out. Approximately $1-2 \times 10^6$ *Fusobacterium nucleatum* cells/ml was seeded and incubated anaerobically for 48 hours. The read out was by the addition of BacTiter Glow and luminescence read out.

Figure 16:
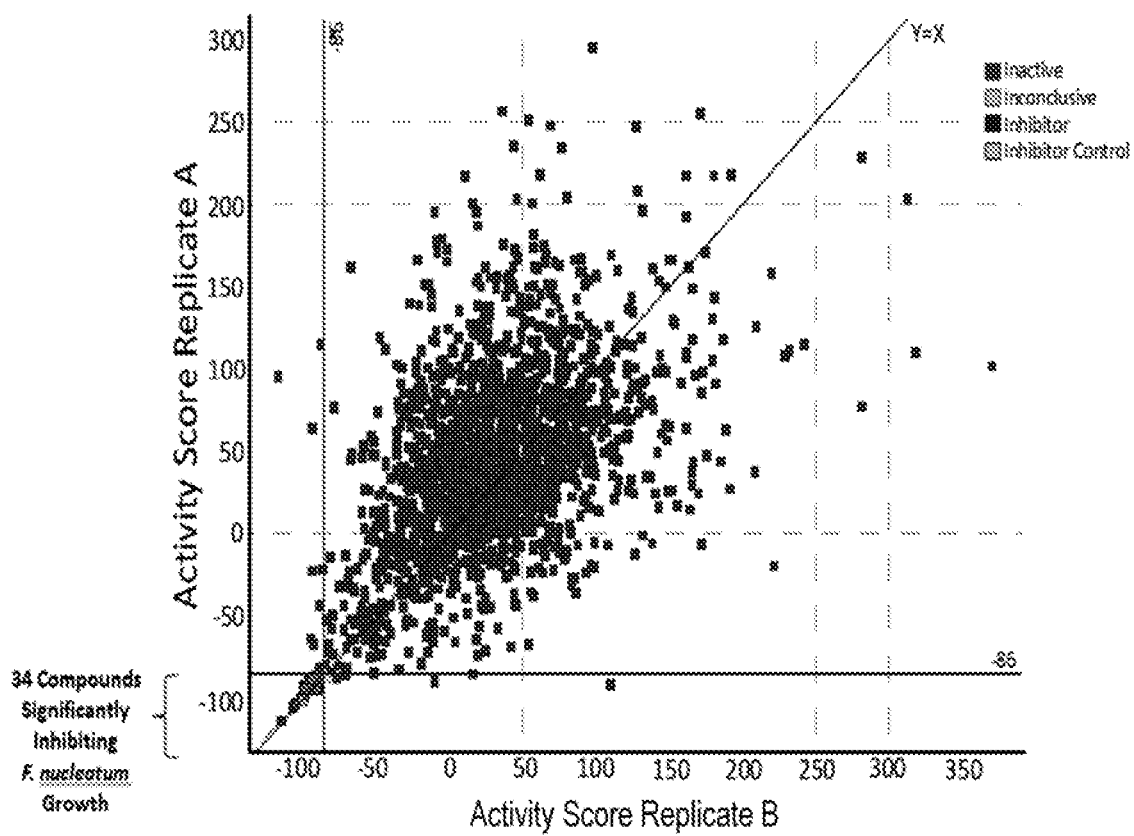
FIG. 16 depicts determining threshold to identify inhibitor hits. Neutral Control=untreated *F. nucleatum*. Inhibitor Control=*F. nucleatum* treated with metronidazole. 3 SD from mean of neutral controls=−86% inhibition hit cut-off.
Figure 17:
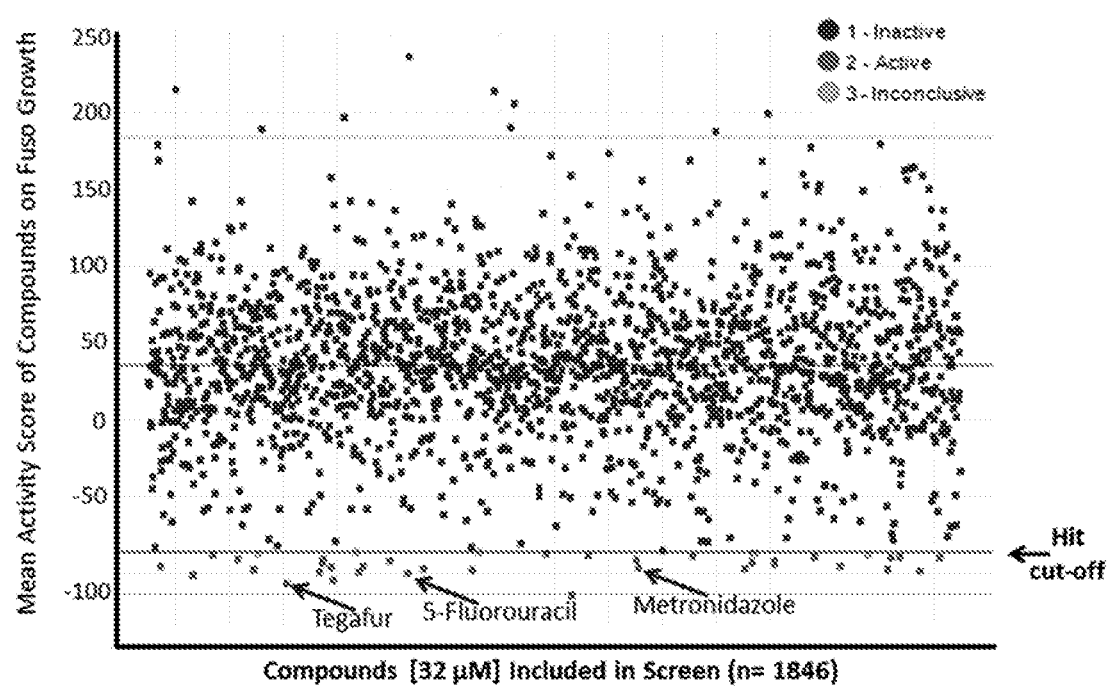
FIG. 17 depicts identifying compounds that inhibit *Fusobacterium* growth. The CRC drug, 5-FU, is a potent inhibitor of *Fusobacterium* growth. 3 SD from mean of neutral controls=−86% inhibition hit cut-off. 34 inhibitory compounds identified.
Figure 18:
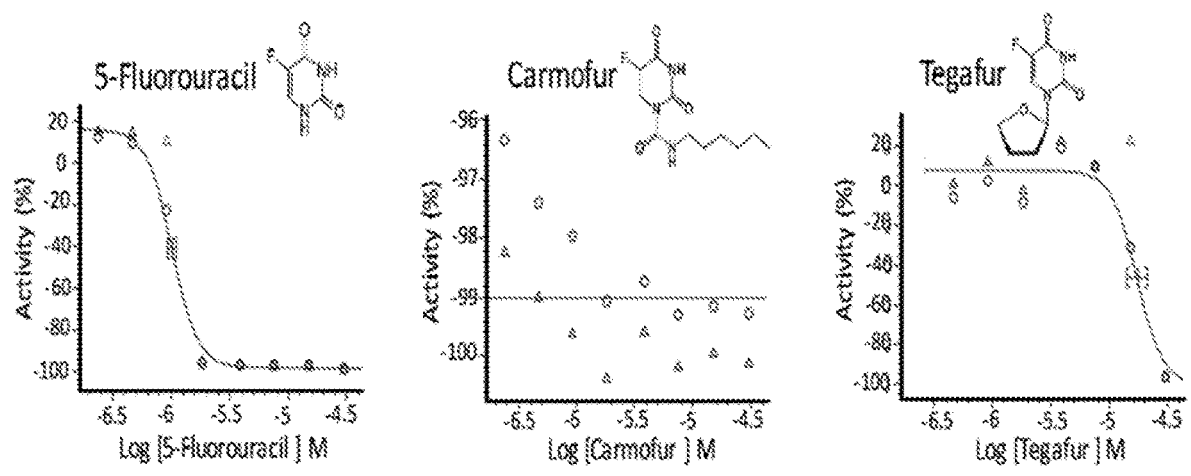
FIG. 18 depicts validation of inhibitor hits (and related compounds). The 5-FU prodrug Carmofur is a potent inhibitor of *Fusobacterium* growth. Validation/dose plates: 8-point, 2-fold dilutions, range 30-0.23 µM. Dose Response Curves [0.32-30 µM]: COCA36F3 *F. nucleatum* (colorectal cancer isolate).
Figure 19:
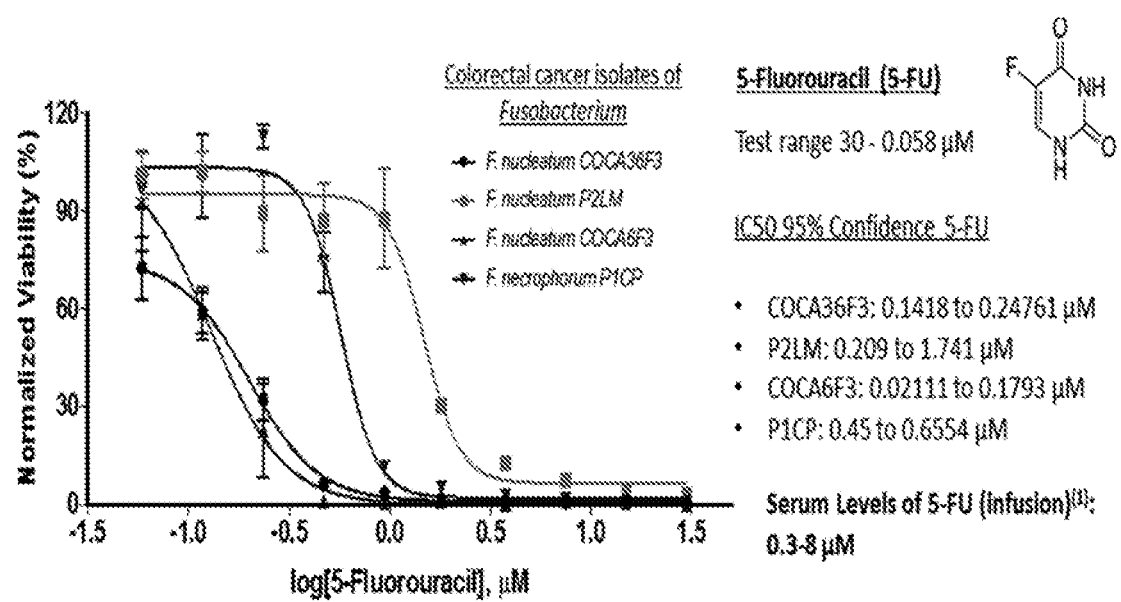
FIG. 19 depicts validation of with additional patient CRC isolates of *Fusobacterium*. 5-Fluorouracil inhibits *Fusobacterium* growth at levels comparable to achievable doses in plasma of treated patients. (Takimoto et al., *Clinical cancer research: an official journal of the American Association for Cancer Research* 5, 1347-1352 (1999)).

A method for determining the threshold to identify inhibitor hits was established and carried out (FIG. 16). Thirty-four compound inhibitors were identified to significantly inhibit *F. nucleatum* growth, including CRC drug, 5-FU, and metronidazole (FIG. 17). Validation of inhibitor hits and related compounds was carried out and dose response was determined for 5-FU, carmofur, and tegafur (FIG. 18). Validation of inhibitor hits was also carried out with additional patient CRC isolates of *Fusobacterium* (FIG. 19). Applicants found that 5-FU inhibits *Fusobacterium* growth at levels comparable to achievable doses in plasma of treated patients. Applicants also investigated whether the presence of *Fusobacterium* in colorectal tumors can explain patient response to 5-FU-based therapies. Data of 91 patient colorectal adenocarcinoma tumors with recurrence were obtained by *Fusobacterium* culture and bacterial 16s rRNA sequencing analysis. Applicants found that *Fusobacterium*-positive colorectal tumors treated with 5-FU or a 5-FU prodrug are less likely to develop recurrence/metastasis (FIG. 20).

In summary, Applicants' data demonstrates: (1) 5-FU (and prodrugs) are potent inhibitors of *Fusobacterium* growth (Applicants have tested patient colorectal cancer isolates of *Fusobacterium nucleatum* and *Fusobacterium necrophorum*); (2) 5-FU inhibition of *Fusobacterium* occurs within a range comparable to patient plasma levels when receiving 5-fluorouracil infusion; (3) the 5-FU analog, carmofur (contains a hexylcarbomoyl tail), is even more potent in killing *Fusobacterium* than the active drug 5-FU; and (4) *Fusobacterium*-positive colorectal tumors treated with 5-FU or a 5-FU prodrug are less likely to develop recurrence/metastasis (p<0.05) based on the determined *Fusobacterium* status of 43 primary colecteral adenocarcinoma patients (with recurrence information) that were treated with 5-FU or a 5-FU prodrug.

Example 3: Association of Dietary Patterns with Risk of Colorectal Cancer Subtypes Classified by *Fusobacterium nucleatum* in Tumor Tissue Accumulating evidence suggests that the human gut microbiome is linked to colorectal cancer development (Ahn et al., *J. Natl. Cancer Inst.* 2013; 105(24):1907-1911; Dejea et al., *Proc. Nat. Acad. Sci. USA* 2014; 111(51):18321-18326; Nakatsu et al., *Nat. Commun.* 2015; 6:8727; Flemer et al., *Gut* [published online Mar. 18, 2016], doi:10.1136/gutnl-2015-309595). *Fusobacterium nucleatum* has been found to be enriched in colorectal cancer tissue relative to normal adjacent colonic tissue and is detected at higher levels in stool among individuals with colorectal cancer compared with those without cancer. (Ahn et al., *J. Nat. Cancer Inst.* 2013; 105(24):1907-1911; Kostic et al., Genome Res. 2012; 22(2):292-298; Castellarin et al., Genome Res. 2012; 22(2):299-306; McCoy et al., PLoS One 2013; 8(1):e53653; Warren et al., Microbiome 2013; 1(1): 16; Mima et al., JAMA Oncol. 2015; 1(5):653-661; Sinha et al., PLoS One 2016; 11(3):e0152126). Recent experimental data suggest that *F nucleatum* may contribute to colorectal carcinogenesis through modulation of host immunity and activation of pathways associated with cellular proliferation. (Mima et al., JAMA Oncol. 2015; 1(5):653-661; Rubinstein et al., Cell Host Microbe 2013; 14(2):195-206; Gur et al., Immunity 2015; 42(2):344-355). Furthermore, a higher amount of *F nucleatum* in colorectal cancer tissue has been linked to shorter survival, proximal tumor location, and specific tumor molecular features, such as high level CpG island methylator phenotype and microsatellite instability. (Ito et al., Int. J. Cancer 2015; 137(6); 1258-1268; Mima et al., Gut 2016; 65(12)1973-1980; Tahara et al., Cancer Res. 2014 74(5):1311-1318).

Prudent dietary patterns—rich in fruits, vegetables, and whole grains—have been associated with a lower risk of colorectal cancer and adenoma (Fung et al., Arch Intern Med. 2003; 163(3):309-314; Terry et al., Am J Epidemiol 2001; 154(12):1143-1149; Kim et al., Int. J. Cancer 2005; 115(5):790-798; Cottet et al., Eur J Cancer Prev 2005; 14(1):21-29; Flood et al., Am J Clin Nutr 2008; 88(1):176-184; Mizoue et al., Am J Epidemiol 2005; 1161(4):338-345) as reviewed in a recent systematic meta-analysis. (Magalhaes et al., Eur J Cancer Prev 2012; 21(1):15-23). In contrast, Western dietary patterns—dominated by red and processed meats—have been linked with colorectal carcinogenesis. (Fung et al., Arch Intern Med. 2003; 163(3):309-314; Magalhaes et al., Eur J Cancer Prev 2012; 21(1):15-23). Although mechanisms underlying these diet-cancer associations remain unclear, it is postulated that the gut microbiota may play a mediating role. (Song et al., Gastroenterology 2015; 148(6):1244-60.e16). Recently, in a dietary intervention study, stool *F. nucleatum* levels markedly increased after participants were switched from a prudent-style, high-fiber, low-fat diet to a low-fiber, high-fat diet. (O'Keefe et al., Nat. Commn. 2015; 6:6342). In addition, accumulating data suggest that low fiber consumption and high meat intake may be associated with altered bacterial and metagenomic profiles as well as an inflammatory phenotype determined by serum levels of metabolites. (Sonnenburg et al., Nature 2016; 529(7585):212-215; Cotillard et al., Nature 2013; 500(7464):585-588; Le Chatelier et al., Nature 2013; 500(7464):541-546; Koeth et al., Nat. Med. 2013; 19(5): 576-585).

Based on these findings, Applicants hypothesized that the inverse association between prudent diets and risk of colorectal cancer might be more evident for a cancer subgroup enriched with tissue *F nucleatum* than for a subgroup without detectable tissue *F nucleatum*. To test this hypothesis, Applicants used 2 US nationwide, prospective cohort studies: the Nurses' Health Study (NHS) (Jun. 1, 1980, to Jun. 1, 2012) and the Health Professional Follow-up Study (HPFS). These 2 studies offered a unique opportunity to integrate prospectively collected, regularly updated dietary intake data with tissue microbial features in incident colorectal cancers that occurred over longterm follow-up.

Summary

*Fusobacterium nucleatum* appears to play a role in colorectal carcinogenesis through suppression of the hosts' immune response to tumor. Evidence also suggests that diet influences intestinal *F nucleatum*. However, the role of *F nucleatum* in mediating the relationship between diet and the risk of colorectal cancer is unknown.

The objective was to test the hypothesis that the associations of prudent diets (rich in whole grains and dietary fiber) and Western diets (rich in red and processed meat, refined grains, and desserts) with colorectal cancer risk may differ according to the presence of *F nucleatum* in tumor tissue.

A prospective cohort study was conducted using data from the Nurses' Health Study (Jun. 1, 1980, to Jun. 1, 2012) and the Health Professionals Follow-up Study (Jun. 1, 1986, to Jun. 1, 2012) on a total of 121 700 US female nurses and 51 529 US male health professionals aged 30 to 55 years and 40 to 75 years, respectively (both predominantly white individuals), at enrollment. Data analysis was performed from Mar. 15, 2015, to Aug. 10, 2016. Subjects were exposed to prudent and western diets.

Main outcomes and measures were incidence of colorectal carcinoma subclassified by *F. nucleatum* status in tumor tissue, determined by quantitative polymerase chain reaction. Of the 173 229 individuals considered for the study, 137 217 were included in the analysis, 47 449 were male (34.6%), and mean (SD) baseline age for men was 54.0 (9.8) years and for women, 46.3 (7.2) years. A total of 1019 incident colon and rectal cancer cases with available *F nucleatum* data were documented over 26 to 32 years of follow-up, encompassing 3 643 562 person-years. The association of prudent diet with colorectal cancer significantly differed by tissue *F nucleatum* status (P=0.01 for heterogeneity); prudent diet score was associated with a lower risk of *F nucleatum*-positive cancers (P=0.003 for trend; multivariable hazard ratio of 0.43; 95% CI, 0.25-0.72, for the highest vs the lowest prudent score quartile) but not with *F nucleatum*-negative cancers (P=0.47 for trend, the corresponding multivariable hazard ratio of 0.95; 95% CI, 0.77-1.17). There was no significant heterogeneity between the subgroups in relation to Western dietary pattern scores.

Applicants concluded that Prudent diets rich in whole grains and dietary fiber are associated with a lower risk for *F nucleatum*-positive colorectal cancer but not *F nucleatum*-negative cancer, supporting a potential role for intestinal microbiota in mediating the association between diet and colorectal neoplasms.

Methods
Detailed Methodology

Prior to analysis, a prospective, written protocol was submitted and approved by the research groups that oversaw the Nurses' Health Study and the Health Professionals Follow-up Study.

At baseline in the NHS, Applicants excluded 1,001 participants with a prior history of cancer, 1,044 participants with a history of ulcerative colitis, and 430 participants with recorded intakes less than 600 calories per day. At baseline in the HPFS, Applicants excluded 1,997 participants with a prior history of cancer and 475 participants with a prior history of ulcerative colitis.

Normal and tumor sections from all colorectal carcinoma cases in this study were reviewed by a pathologist (S.O.). For various characteristics, colorectal cancer patients with available tumor tissue data (n=1,019) were generally similar to patients without available tumor tissue data (n=2,241) (median age 66.8 vs 67.1; current smoker, 15% vs. 15%; mean body-mass index, 26.3 vs. 26.2 kg/m2; previous lower gastrointestinal endoscopy, 34% vs. 36%; mean red meat intake [servings per day], 0.55 vs. 0.54; mean dietary fiber intake, 20.0 vs 19.7 g per day; mean alcohol intake, 8.5 vs. 8.2 g per day). Tumors with and without available tissue were also similar by clinical factors, including grade and stage [proportion of poorly differentiated tumors, 16% vs. 17%; mean pT stage, 2.7 vs. 2.5; proportion with no regional lymph node metastases, 59% vs. 49%; proportion of distant metastasis (M stage), 11% vs. 17%].

Food items from the FFQ were classified into approximately 40 food groups. Factor analysis was performed using an orthogonal rotation procedure to produce two maximally uncorrelated factors, selected based upon the largest eigenvalues. All analyses were adjusted for total caloric intake (kcal per day) and stratified by age (in months), year of questionnaire return and sex (in the analysis using combined cohorts). In multivariable analysis, Applicants adjusted for potential confounders including body mass index (kg/m2), pack-years of smoking (never, 0 to 4 pack-years, 5 to 19 pack-years, 20 to 39 pack-years, or >40 years), family history of colorectal cancer in any first-degree relative (yes or no), previous lower gastrointestinal endoscopy (yes or no), postmenopausal hormone use (for women only; never, past, or current), physical activity [quintiles of metabolic-equivalent task (MET)-hours per week], and regular aspirin or NSAID use (>2 tablets per week; yes or no). Prior to pooling data from the two cohorts, Applicants examined the possible heterogeneity between cohorts, using the Q statistic for the association between the prudent (or Western) dietary score and overall incidence of colorectal cancer.

Participants whose *F. nucleatum* tumor status was unknown and those who died of causes other than colorectal cancer were censored during the 26-32 years of follow-up. In addition, in the incidence analysis of one subtype, incidences of other tumor subtypes were treated as censored data. Applicants assessed the proportional hazards assumption by including the product term between age and each covariable (including the exposure of interest, prudent dietary pattern scores) into the Cox model, and testing the statistical significance of the term by Wald test. No deviation from proportional hazards assumption was detected at the a of 0.05 level. Applicants did not conduct a formal power calculation prior to the current analysis. Applicants recognized that participants might have varied their diets over the study period. Thus, Applicants utilized time-varying covariates such that each individual participant contributed multiple person-times with differing dietary data provided on each questionnaire.

Study Population

Applicants used data drawn from 2 ongoing prospective cohort studies, the NHS and the HPFS. The NHS began in 1976 among 121 700 US female nurses aged 30 to 55 years at enrollment. The HPFS began in 1986 among 51 529 US male health professionals aged 40 to 75 years at enrollment. In both cohorts, participants have returned questionnaires every 2 years, with follow-up rates exceeding 90%, to provide information about lifestyle and dietary factors, medication use, and diagnoses of colorectal cancer and other diseases. The institutional review board at the Brigham and Women's Hospital and Harvard T. H. Chan School of Public Health approved this study, and informed consent was obtained from all participants. The study was conducted from Jun. 1, 1980, to Jun. 1, 2012.

Of 173 229 individuals considered for the study, a total of 137 217 individuals (47 449 men and 89 768 women) were included in this analysis. Applicants excluded participants with implausibly high or low caloric intakes (i.e., <600 or >3500 kcal/d for women and <800 or >4200 kcal/d for men), missing dietary pattern data, or those with a history of ulcerative colitis or cancer (except for nonmelanoma skin cancer) before baseline (1980 for the NHS and 1986 for the HPFS) (Methods described herein).

Assessment of Diet

Participants reported average food intake over the preceding year (of each questionnaire return) through semi-quantitative food frequency questionnaires, which have been previously validated and described. (Rimm et al., Am J Epidemiol 1992; 135(10):1114-1126). Total nutrient intake was calculated by summing intakes from all foods and adjusted for total energy intake by the residual method. As previously described, total dietary fiber was calculated according to methods from the Association of Official Analytic Chemists. (Ananthakrishnan et al., Gastroenterology 2013; 145(5):970-977). For this analysis, Applicants used information from food frequency questionnaires administered in the following years: 1980, 1984, 1986, 1990, 1994, 1998, 2002, 2006, and 2010 for the NHS and 1986, 1990, 1994, 1998, 2002, 2006, and 2010 for the HPFS.

Assessment of Colorectal Cancer Cases

In both cohorts, incident cases of colorectal cancer were reported by participants through the 2012 follow-up for the HPFS and NHS. Applicants identified and confirmed lethal colorectal cancer cases through information from various sources including next of kin, the National Death Index, death certificates, and medical records. A study physician (including J. A. M. and C.S.F.), blinded to exposure information, reviewed records and extracted data on histologic type, anatomical location, and stage. The cohort study groups attempted to collect formalin-fixed, paraffin-embedded (FFPE) tissue specimens from hospitals throughout the United States as previously detailed. (Mima et al., JAMA Oncol. 2015; 1(5):653-661). Cases with available tissue data (n=1019) for the present study were similar to those without tissue data (n=2241) regarding patient and clinical characteristics (Methods described herein).

*F nucleatum* Analysis

Applicants extracted DNA from colorectal cancer tissue obtained from sections of FFPE tumor blocks (QIAamp DNA FFPE tissue kits; Qiagen). Applicants performed a real-time polymerase chain reaction (PCR) assay using custom TaqMan primer/probe sets (Applied Biosystems) for the nusG gene of *F nucleatum*. (Mima et al., JAMA Oncol.

2015; 1(5):653-661). The interassay coefficient of variation of cycle threshold values from each of 5 selected specimens in 5 different batches was less than 1% for all targets in the validation study. (Mima et al., Gut 2016; 65(12):1973-1980). *Fusobacterium nucleatum* positivity was defined as a detectable level of *F nucleatum* DNA within 45 PCR cycles, and *F nucleatum* negativity was defined as an undetectable level with a proper amplification of human reference gene SLCO2A1 (HGNC: 10955).

Statistical Analysis

All statistical tests were 2-sided. To account for multiple testing for the 2 primary hypotheses (related to prudent and Western dietary scores) associated with the 2 tumor subtype variables, Applicants adjusted the 2-sided $\alpha$ level to 0.01 (approximately 0.05/4) by simple Bonferroni correction in our primary and secondary analysis.

Two maximally uncorrelated dietary patterns—one named prudent and another named Western—were derived by principal component analysis, as previously described and validated with good reproducibility. (Fung et al., Arch Intern Med. 2003; 163(3):309-314; Hu et al., Am J Clin Nutr 2000; 72(4):912-921). Factor loadings were derived based on the correlations between food groups and the 2 derived factors. Each participant was assigned a factor score, determined by adding the reported frequencies of food group intakes weighted by the factor loadings. These factor scores were then standardized to have a mean (SD) of 0 (1). To capture long-term habitual consumption, Applicants calculated the cumulative mean of the prudent (or Western) dietary pattern scores from preceding food frequency questionnaires up to each questionnaire cycle. Then, the cumulative average score was categorized into sex-specific quartiles and used as the primary exposure variable.

Using Cox proportional hazards regression models, Applicants computed hazard ratios (HRs) to examine the association of the prudent or Western dietary score with incidence of colorectal cancer. To test for trend with the Wald test, participants were assigned to the median score of their sex-specific dietary pattern quartile, and then this variable was entered into the models as a continuous term. The covariates included in the multivariable models are described in Table 5 and the method described herein. All analyses were adjusted for total caloric intake (kilocalories per day) and stratified by age (in months), year of questionnaire return, and sex (in the analysis using combined cohorts). In multivariable analysis, Applicants adjusted for potential confounders, including body mass index (calculated as weight in kilograms divided by height in meters squared), pack-years of smoking (never, 0-4 pack-years, 5-19 pack-years, 20-39 pack-years, or >40 pack-years), family history of colorectal cancer in any first-degree relative (yes or no), previous lower gastrointestinal endoscopy (yes or no), postmenopausal hormone use (for women only: never, past, or current), physical activity (quintiles of metabolic equivalent task hours per week), and regular use of aspirin or nonsteroidal anti-inflammatory agents ($\geq$2 tablets per week: yes or no).

TABLE 5

Hazard Ratios of Incident Colorectal Cancer Overall and by *Fusobacterium nucleatum* Status

| Characteristic | Quartile 1 | Quartile 2 | Quartile 3 | Quartile 4 | P Value Trend[b] | Heterogeneity[c] |
|---|---|---|---|---|---|---|
| Prudent Dietary Pattern Overall colorectal cancer | | | | | | |
| Person-years | 913 569 | 907 676 | 912 395 | 909 922 | NA | NA |
| No. of cases (n = 1019), No. (%) | 250 (24.5) | 248 (24.3) | 268 (26.3) | 253 (24.8) | | NA |
| Age-adjusted HR (95% CI)[d] | 1 [Reference] | 0.93 (0.77-1.11) | 0.90 (0.75-1.08) | 0.79 (0.65-0.95) | .01 | NA |
| Multivariable HR (95% CI)[e] | 1 [Reference] | 0.95 (0.80-1.14) | 0.95 (0.79-1.14) | 0.85 (0.69-1.03) | .08 | NA |
| *F nucleatum*-positive colorectal cancer | | | | | | |
| No. of cases (n = 125), No. (%) | 43 (34.4) | 26 (20.8) | 34 (27.2) | 22 (17.6) | NA | NA |
| Age-adjusted HR (95% CI)[d] | 1 [Reference] | 0.54 (0.33-0.89) | 0.67 (0.42-1.05) | 0.40 (0.24-0.67) | <.001 | NA |
| Multivariable HR (95% CI)[e] | 1 [Reference] | 0.56 (0.34-0.92) | 0.70 (0.44-1.10) | 0.43 (0.25-0.72) | .003 | NA |
| *F nucleatum*-negative colorectal cancer | | | | | NA | .01 |
| No. of cases (n = 894), No. (%) | 207 (23.2) | 222 (24.8) | 234 (26.2) | 231 (25.8) | NA | NA |
| Age-adjusted HR (95% CI)[d] | 1 [Reference] | 1.01 (0.83-1.22) | 0.96 (0.79-1.16) | 0.88 (0.72-1.08) | .15 | NA |
| Multivariable HR (95% CI)[e] | 1 [Reference] | 1.04 (0.86-1.26) | 1.00 (0.83-1.22) | 0.95 (0.77-1.17) | .47 | NA |
| Western Dietary Pattern Overall colorectal cancer | | | | | | |
| Person-years | 910 656 | 910 525 | 910 465 | 911 916 | NA | NA |
| No. of cases (n = 1019), No. (%) | 244 (23.9) | 275 (27.0) | 243 (23.8) | 257 (25.2) | NA | NA |
| Age-adjusted HR (95% CI)[d] | 1 [Reference] | 1.24 (1.01-1.48) | 1.21 (1.00-1.46) | 1.46 (1.18-1.82) | .001 | NA |

TABLE 5-continued

Hazard Ratios of Incident Colorectal Cancer Overall and by *Fusobacterium nucleatum* Status

| Characteristic | Quartile 1 | Quartile 2 | Quartile 3 | Quartile 4 | P Value Trend[b] | Hetero-geneity[c] |
|---|---|---|---|---|---|---|
| Multivariable HR (95% CI)[e] | 1 [Reference] | 1.19 (1.00-1.43) | 1.12 (0.92-1.36) | 1.29 (1.03-1.62) | .05 | NA |
| *F nucleatum*-positive colorectal cancer | | | | | | NA |
| No. of cases (n = 125), No. (%) | 25 (20.2) | 33 (26.4) | 33 (26.4) | 34 (27.2) | NA | NA |
| Age-adjusted HR (95% CI)[d] | 1 [Reference] | 1.42 (0.84-2.40) | 1.59 (0.94-2.69) | 1.92 (1.12-3.29) | .01 | NA |
| Multivariable HR (95% CI)[e] | 1 [Reference] | 1.37 (0.81-2.31) | 1.49 (0.88-2.53) | 1.69 (0.98-2.90) | .05 | NA |
| *F nucleatum*-negative colorectal cancer | | | | | NA | .23 |
| No. of cases (n = 894), No. (%) | 219 (24.5) | 242 (27.1) | 210 (23.5) | 223 (24.9) | NA | NA |
| Age-adjusted HR (95% CI)[d] | 1 [Reference] | 1.25 (1.03-1.50) | 1.16 (0.95-1.42) | 1.42 (1.13-1.78) | .006 | NA |
| Multivariable HR (95% CI)[e] | 1 [Reference] | 1.20 (0.99-1.44) | 1.08 (0.88-1.33) | 1.25 (0.99-1.58) | .12 | NA |

Abbreviations: HR, hazard ratio; NA, not applicable.
[a] According to prudent or Western dietary score quartiles in the combined cohort of the Health Professionals Follow-up Study (1986-2012) and the Nurses' Health Study (1980-2012).
[b] Tests for trend were conducted using the median value of each quartile category as a continuous variable.
[c] We tested for heterogeneity by using a likelihood ratio test comparing a model that allows separate associations for the 2 colorectal cancer subgroups (ie, *F. nucleatum*-positive and *F nucleatum*-negative subgroups) with a model that assumes a common association.
[d] Stratified by age, calendar year, and sex and adjusted for total caloric intake (kilocalories per day).
[e] Stratified as listed in the above footnote and additionally adjusted for family history of colorectal cancer in any first-degree relative, history of previous endoscopy, pack-years of smoking (never, 0-4, 5-19, 20-39, or ≥40), body mass index, physical activity (metabolic-equivalent task hours per week), and regular aspirin or nonsteroidal anti-inflammatory drug use (≥2 tablets/wk).

To examine whether the association between dietary patterns and incidence of colorectal cancer subgroups differed according to tissue *F nucleatum* status, Applicants used Cox proportional hazards regression models with a duplication method for competing risks data. As our primary hypothesis testing, Applicants tested for heterogeneity by using a likelihood ratio test, comparing a model that allows for separate associations of dietary patterns and risk of cancer subgroups according to *F nucleatum* status with a model that assumes a common association. (Wang et al., Stat Med 2016; 35(5):782-800). In secondary analyses, Applicants examined heterogeneity of the associations with cancer subgroups in relation to dominant factor loadings for the prudent dietary pattern using cumulative average intakes of fruits, vegetables, legumes, and whole grains as well as energy-adjusted intakes of fat, fiber, and protein, all of which were categorized into quartiles. Applicants used SAS software, version 9.3 (SAS Institute Inc) for all statistical analyses. Data analysis was performed from Mar. 15, 2015, to Aug. 10, 2016.

Results

Of the 137 217 individuals included in the analysis, 47 449 were male (34.6%); mean (SD) baseline age for men was 54.0 (9.8) years and for women, 46.3 (7.2) years. Two major, uncorrelated dietary patterns were identified by factor analysis. The prudent dietary pattern was characterized by high intake of vegetables, fruits, whole grains, and legumes, and the Western dietary pattern was characterized by red and processed meats, refined grains, and desserts (Table 6). Consistent with prior analyses, (Fung et al., Arch Intern Med 2003; 163(3):309-314) participants with high prudent scores in the HPFS and NHS tended to smoke less, exercise more, and have greater rates of lower gastrointestinal endoscopy, whereas Western pattern scores were associated with behaviors typically considered unhealthy (Table 7).

TABLE 6

Factor Loading Matrix for Dietary Patterns in the Health Professionals Follow-up Study (HPFS) and the Nurses' Health Study (NHS).

| | HPFS | | NHS | |
|---|---|---|---|---|
| Food Item[1] | Prudent pattern | Western pattern | Prudent pattern | Western pattern |
| Other vegetables[2] | .69 | | .68 | |
| Yellow vegetables | .65 | | .65 | |
| Leafy green vegetables | .63 | | .64 | |
| Cruciferous vegetables | .63 | | .61 | |
| Fruits | .58 | | .58 | |
| Legumes | .62 | | .57 | |
| Tomatoes | .52 | | .48 | |
| Fish | .46 | | .51 | |
| Whole grains | .38 | | .41 | |
| Potatoes | .33 | | | .34 |
| Poultry | .32 | | .41 | |
| Water | | | .32 | |
| Salad dressing | | | .33 | |
| Low-fat dairy | | | .32 | |
| Red meat | | .66 | | .61 |
| Processed meat | | .61 | | .58 |
| High fat dairy | | .51 | | .50 |
| French fries | | .49 | | .46 |
| Eggs | | .47 | | .41 |
| Desserts[3] | | .43 | | .45 |
| Condiments[4] | | .39 | | .36 |
| Refined grains | | .38 | | .38 |
| Butter | | .38 | | .50 |
| Mayonaise | | .36 | | .34 |
| Margarine | | .34 | | .32 |
| Snacks5 | | .34 | | |

TABLE 6-continued

Factor Loading Matrix for Dietary Patterns in the Health Professionals Follow-up Study (HPFS) and the Nurses' Health Study (NHS).

| Food Item[1] | HPFS Prudent pattern | HPFS Western pattern | NHS Prudent pattern | NHS Western pattern |
|---|---|---|---|---|
| Pizza | | .33 | | .36 |
| Creamy soups | | .31 | | .32 |
| Sugar-sweetened beverages | | .31 | | .33 |

[1] Only items with correlation coefficients >0.30 are presented. With the orthogonal rotation used, correlations are identical to factor loading matrix.
[2] Other vegetables include corn, onion, eggplant, celery, green peppers, and mixed vegetables.
[3] Desserts include chocolate, candy bars, cookies, brownies, cake, pie, and pastries.
[4] Condiments include soy sauce, non-dairy creamer, Worcestershire sauce, red chili sauce, and pepper.
5 Snacks include chips, popcorn, and crackers.

TABLE 7

Age-Standardized Characteristics of Participants in the Health Professionals Follow-up Study (HPFS, in 1994) and the Nurses' Health Study (NHS, in 1990) According to Prudent and Western Dietary Score Quartiles (Q1 to Q4).

| | Health Professionals Follow-up Study | | | | Nurses' Health Study | | | |
|---|---|---|---|---|---|---|---|---|
| | Prudent | | Western | | Prudent | | Western | |
| | Q1 | Q4 | Q1 | Q4 | Q1 | Q4 | Q1 | Q4 |
| Characteristic[1] | | | | | | | | |
| Age (mean) | 61.1 | 61.3 | 61.4 | 61.0 | 56.2 | 56.4 | 56.4 | 56.2 |
| Pack-years smoked (mean) | 16.1 | 11.0 | 9.2 | 18.3 | 17.8 | 10.6 | 12.1 | 15.5 |
| Current smoker, % | 12 | 5 | 3 | 13 | 27 | 12 | 13 | 23 |
| Family history of colorectal cancer, % | 13 | 14 | 14 | 13 | 16 | 17 | 16 | 17 |
| History of previous endoscopy, % | 17 | 21 | 22 | 16 | 23 | 40 | 28 | 22 |
| Current multivitamin use, % | 39 | 47 | 47 | 39 | 33 | 44 | 44 | 32 |
| Regular aspirin/NSAID use, %[2] | 42 | 45 | 42 | 46 | 48 | 48 | 45 | 51 |
| Postmenopause, %[3] | | | | | 78 | 79 | 79 | 77 |
| Monopausal hormone use, %[3] | | | | | 32 | 36 | 38 | 30 |
| Body mass index, kg/m$^2$ (mean) | 26.1 | 25.8 | 25.4 | 26.5 | 25.5 | 26.0 | 25.3 | 26.3 |
| Physical activity, MET-hours/week[3] (mean) | 26.4 | 44.8 | 37.7 | 34.4 | 9.9 | 18.3 | 17.6 | 10.9 |
| Dietary intake (means) | | | | | | | | |
| Unprocessed red meat, svg/day | .59 | .52 | .24 | .94 | .53 | .50 | .31 | .76 |
| Processed red meat, svg/day | .33 | .20 | .07 | .54 | .26 | .17 | .09 | .40 |
| Poultry, svg/day | .30 | .52 | .40 | .42 | .27 | .51 | .42 | .36 |
| Fruit, svg/day | 1.64 | 3.86 | 3.08 | 2.42 | 1.52 | 3.28 | 2.44 | 2.29 |
| Vegetable, svg/day | 1.84 | 5.54 | 3.65 | 3.48 | 1.95 | 5.10 | 3.49 | 3.34 |
| Alcohol, g/day | 11.2 | 10.6 | 7.4 | 14.2 | 5.9 | 4.8 | 5.6 | 5.0 |
| Folate, µg/day | 450 | 617 | 627 | 449 | 376 | 490 | 499 | 367 |
| Calcium, mg/day | 864 | 975 | 1024 | 831 | 900 | 1062 | 1151 | 835 |
| Vitamin D, IU/day | 408 | 498 | 541 | 378 | 309 | 376 | 420 | 271 |
| Dietary fiber, g/day | 18 | 29 | 28 | 19 | 15 | 22 | 21 | 19 |

[1] Continuous variables are described as means.
[2] Regular users are defined as ≥2 standard (325-mg) tablets of aspirin or ≥2 tablets of non-steroidal anti-inflammatory drugs (NSAIDs) per week.
[3] The percentages of postmenopausal participants as well as menopausal hormone use are among women only.
[4] Physical activity is represented by the product sum of the metabolic equivalent task (MET) score of each specific recreational activity and hours spent on that activity per week. MET-hours/week values were assessed in 1988 for the NHS.

After 26 years (in HPFS) and 32 years (in NHS) of follow-up encompassing 3643 562 person-years, Applicants documented 1019 incident colorectal cancers with available data on tissue *F nucleatum* status. Among these cancer cases, there were 125 (12.3%) *F nucleatum*-positive tumors and 894 (87.7%) *F nucleatum*-negative tumors. Applicants examined the association of prudent and Western dietary pattern scores with the incidence of overall colorectal cancer. Western dietary pattern scores showed a trend toward associations with overall risk of colorectal cancer in the HPFS (Table 8) and the combined cohort (Table 5); however, statistical significance was not reached with the adjusted α level of 0.01. Applicants did not observe significant heterogeneity in the associations of the dietary scores with colorectal cancer risk between the 2 cohorts (P≥0.21). To maximize statistical power, Applicants used the combined cohort for further analyses.

with those in the lowest quartile, the multivariable HR for *F nucleatum*-positive tumors was 0.43 (95% CI, 0.25-0.72); in contrast, the corresponding HR for *F nucleatum*-negative tumors was 0.95 (95% CI, 0.77-1.17). Applicants found similar differential associations by *F nucleatum* status in men (HPFS) and women (NHS), although statistical power was limited (Table 9). In addition, although statistical power was limited, Applicants found similar results when lev levels of *F nucleatum* were categorized as low or high on the basis of the median cutoff point among *F nucleatum*-positive cases as performed in our previous analyses (Table 10). (Mima et al., JAMA Oncol 2015; 1(5):653-661). Because Applicants observed that the fraction of colorectal cancers enriched with *F nucleatum* gradually decreased from cecum to rectum, (Mima et al., Clin Transl Gastroenterol 2016; 7(11):e200) Applicants conducted exploratory analyses stratified by tumor location (Table 11). The differential

TABLE 8

Hazard Ratios (HRs) of Incident Colorectal Cancer, Overall, According to Prudent or Western Dietary Pattern Score Quartiles in the Health Professionals Follow-up Study and the Nurses' Health Study.

|  | Quartile 1 | Quartile 2 | Quartile 3 | Quartile 4 | $P_{amd}^3$ |
|---|---|---|---|---|---|
| Prudent dietary pattern |  |  |  |  |  |
| Health Professionals Follow-up Study |  |  |  |  |  |
| Person-years | 260, 140 | 258, 863 | 260, 286 | 258, 542 |  |
| No. of cases (n = 388) | 85 | 105 | 112 | 86 |  |
| Age-adjusted HR (95% CI)[1] | 1 (referent) | 1.08 (0.81-1.44) | 1.03 (0.77-1.398 | 0.74 (0.53-1.02) | 0.04 |
| Multivariable HR (95% CI)[2] | 1 (referent) | 1.11 (0.83-1.49) | 1.07 (0.80-1.45) | 0.80 (0.56-1.11) | 0.10 |
| Nurses' Health Study |  |  |  |  |  |
| Person-years | 653, 429 | 648, 813 | 652, 109 | 651, 380 |  |
| No. of cases (n = 631) | 165 | 143 | 156 | 167 |  |
| Age-adjusted HR (95% CI)[1] | 1 (referent) | 0.84 (0.67-1.06) | 0.84 (0.67-1.05) | 0.83 (0.66-1.05) | 0.17 |
| Multivariable HR (95% CI)[2] | 1 (referent) | 0.88 (0.70-1.10) | 0.89 (0.71-1.12) | 0.91 (0.71-1.16) | 0.52 |
| Western dietary pattern |  |  |  |  |  |
| Health Professionals Follow-up Study |  |  |  |  |  |
| Person-years | 259, 064 | 259, 719 | 259, 567 | 259, 480 |  |
| No. of cases (n = 388) | 83 | 104 | 96 | 105 |  |
| Age-adjusted HR (95% CI)[1] | 1 (referent) | 1.42 (1.06-1.91) | 1.45 (1.05-1.98) | 1.80 (1.25-2.59) | 0.003 |
| Multivariable HR (95% CI)[2] | 1 (referent) | 1.37 (1.01-1.84) | 1.35 (0.98-1.86) | 1.62 (1.11-2.37) | 0.02 |
| Nuses' Health Study |  |  |  |  |  |
| Person-years | 651, 592 | 650, 806 | 650, 898 | 652, 436 |  |
| No. of cases (n = 631) | 161 | 171 | 147 | 152 |  |
| Age-adjusted HR (95% CI)[1] | 1 (referent) | 1.18 (0.95-1.47) | 1.09 (0.86-1.40) | 1.31 (1.00-1.73) | 0.09 |
| Multivariable HR (95% CI)[2] | 1 (referent) | 1.13 (0.91-1.41) | 1.01 (0.79-1.29) | 1.13 (0.85-1.51) | 0.55 |

[1]Stratified by age and calendar year and adjusted for total caloric intake.
[2]As above, and additionally adjusted for family history of colorectal cancer in any first-degree relative, history of previous endoscopy, pack-years of smoking (never, 0-4, 5-19, 20-39, or >40), body mass index (kg/m$^2$), physical activity (MET-hours/week), regular aspirin or NSAID use (≥2 tablets/week), menopausal hormone therapy status (never, past current) (women only), and total caloric intake (kcal/day).
[3]Tests for trend were conducted using the mediam value of each category as a continuous variable.
Abbreviations: CI, confidence interval; HR, hazard ratio; MET, metabolic equivalent task; NSAID, non-steroidal anti-inflammatory drug.

Applicants then tested our primary hypothesis that the association of prudent and Western diets with colorectal cancer incidence might differ according to the presence of *F nucleatum* in tumor tissue. Notably, the association between prudent dietary pattern and risk of colorectal cancer significantly differed by tumor *F nucleatum* status (P=0.01 for heterogeneity) (Table 5). Applicants found a significant inverse association of prudent dietary scores with *F nucleatum*-positive cancer risk (P=0.003 for trend) but not with *F nucleatum*-negative cancer risk (P=0.47 for trend). Comparing participants in the highest prudent dietary score quartile association of prudent diet score with colorectal cancer by tissue *F nucleatum* status appeared to be consistent in both proximal and distal cancer strata.

When Applicants examined the association of the Western dietary pattern with colorectal cancer subgroups according to tumor *F nucleatum* status, although Western dietary pattern scores appeared to be more strongly associated with *F nucleatum*-positive cancer risk, there was no significant heterogeneity between the subgroups (P=0.23 for heterogeneity) (Table 5).

TABLE 9

Cohort-Specific Hazard Ratios (HRs) of Incident Colorectal Cancer Subgroups by *F. nucleatum* status According to Prudent Dietary Score Quartiles in the Health Professionals Follow-up Study (1986-2012) and the Nurses' Health Study (1980-2012).

| Prudent dietary score | Quartile 1 | Quartile 2 | Quartile 3 | Quartile 4 | $P_{trend}$[2] | $P_{heterogeneity}$[3] |
|---|---|---|---|---|---|---|
| Health Professionals Follow-up Study | | | | | | |
| *F. nucleatum* (+) colorectal cancer (n = 39) | 12 | 11 | 11 | 5 | | |
| Multivariable HR (95% CI)[1] | 1 (referent) | 0.82 (0.32-1.73) | 0.74 (0.32-1.73) | 0.31 (0.11-0.90) | 0.02 | |
| *F. nucleatum* (−) colorectal cancer (n = 349) | 73 | 94 | 101 | 81 | | 0.07 |
| Multivariable HR (95% CI)[1] | 1 (referent) | 1.16 (0.85-1.59) | 1.13 (0.82-1.55) | 0.87 (0.61-1.24) | 0.29 | |
| Nurses' Health Study | | | | | | |
| *F. nucleatum* (+) colorectal cancer (n = 86) | 31 | 15 | 23 | 17 | | |
| Multivariable HR (95% CI)[1] | 1 (referent) | 0.47 (0.25-0.87) | 0.68 (0.4-1.18) | 0.49 (0.27-0.89) | 0.05 | |
| *F. nucleatum* (−) colorectal cancer (n = 545) | 134 | 128 | 133 | 150 | | 0.05 |
| Multivariable HR (95% CI)[1] | 1 (referent) | 0.97 (0.76-1.25) | 0.94 (0.73-1.2) | 1.01 (0.78-1.3) | 0.97 | |

[1]Stratified by age and calendar year and adjusted for total caloric intake, family history of colorectal cancer in any first-degree relative, history of previous endoscopy, pack-years of smoking (never, 0-4, 5-19, 20-39, or >40), body mass index (kg/m²), physical activity (MET- hours/week), regular aspirin or NSAID use (≥2 tablets/week), menopausal hormone therapy status (never, past current) (women only), and total caloric intake (kcal/day).
[2]Tests for trend were conducted using the median value of each category as a continuous variable.
[3]We tested for heterogeneity by using a likelihood ratio test, comparing a model that allows separate associations for the two colorectal cancer subgroups (i.e., *F. nucleatum*-positive and negative subgroups) with a model that assumes a common association.
Abbreviations: CI, confidence interval; HR, hazard ratio; MET, metabolic equivalent task; NSAID, non-steroidal anti-inflammatory drug.

TABLE 10

Hazard ratios (HRs) of Incident Colorectal Cancer-by Low, High, or No Detectable Levels of *F. Nucleatum* in Tumor Tissue-According to Prudent or Western Dietary Score Quartiles in the Combined Cohort of the Health Professionals Follow-up Study (1986-2012) and the Nurses' Health Study (1980-2012).

| | Quartile 1 | Quartile 2 | Quartile 3 | Quartile 4 | $P_{trend}$[2] | $P_{heterogeneity}$[3] |
|---|---|---|---|---|---|---|
| Prudent dietary pattern | | | | | | |
| *F. nucleatum*-high colorectal cancer | | | | | | |
| No. of cases (n = 60) | 20 | 10 | 20 | 10 | | |
| Multivariable HR (95% CI)[1] | 1 (referent) | 0.47 (0.22-1.00) | 0.92 (0.49-1.73) | 0.43 (0.20-0.92) | 0.08 | |
| *F. nucleatum*-low colorectal cancer | | | | | | |
| No. of cases (n = 65) | 23 | 16 | 14 | 12 | | 0.03 |
| Multivariable HR (95% CI)[1] | 1 (referent) | 0.65 (0.34-1.23) | 0.52 (0.26-1.01) | 0.43 (0.22-0.87) | 0.02 | |
| *F. nucleatum*-negative colorectal cancer | | | | | | |
| No. of cases (n = 894) | 207 | 222 | 234 | 231 | | |
| Multivariable HR (95% CI)[1] | 1 (referent) | 1.04 (0.86-1.26) | 1.00 (0.83-1.22) | 0.95 (0.77-1.17) | 0.47 | |
| Western dietary pattern | | | | | | |
| *F. nucleatum*-high colorectal cancer | | | | | | |
| No. of cases (n = 60) | 13 | 18 | 17 | 12 | | |
| Multivariable HR (95% CI)[1] | 1 (referent) | 1.44 (0.70-2.95) | 1.49 (0.70-3.09) | 1.16 (0.52-2.60) | 0.72 | |
| *F. nucleatum*-low colorectal cancer | | | | | | |
| No. of cases (n = 65) | 12 | 15 | 16 | 22 | | 0.19 |
| Multivariable HR (95% CI)[1] | 1 (referent) | 1.29 (0.60-2.78) | 1.50 (0.70-3.20) | 2.25 (1.08-4.66) | 0.02 | |
| *F. nucleatum*-negative colorectal cancer | | | | | | |
| No. of cases (n = 894) | 219 | 242 | 210 | 223 | | |
| Multivariable HR (95% CI)[1] | 1 (referent) | 1.20 (0.99-1.44) | 1.08 (0.88-1.33) | 1.25 (0.99-1.58) | 0.12 | |

[1]Stratified by age, calendar year, and gender and adjusted for total caloric intake (kcal/day), family history of colorectal cancer in any first-degree relative, history of previous endoscopy, pack-years of smoking (never, 0-4, 5-19, 20-39, or ≥40), body mass index (kg/m²), physical activity (MET-hours/week), and regular aspirin or NSAID use (≥2 tablets/week).
[2]Tests for trend were conducted using the median value of each quartile category as a continuous variable.
[3]We tested for heterogeneity by using a likelihood ratio test, comparing a model that allows separate associations for the two colorectal cancer subgroups (i.e., *F. nucleatum*-positive and negative subgroups) with a model that assumes a common association.
Abbreviations: CI, confidence interval; HR, hazard ratio; MET, metabolic equivalent task; NSAID, non-steroidal anti-inflammatory drug.

TABLE 11

Relative Risks (RRs) of Incident Colorectal Cancer Subgroups, Jointly Classified by F. Nucleatum Status and Anatomic Subsite, According to Prudent Dietary Pattern Scores Quartiles in the Combined Cohort of the Health Professionals Follow-up Study (1986-2012) and the Nurses' Health Study (1980-2012).

| Anatomic subsite[1] | F. nucleatum status | Quartile 1 | Quartile 2 | Quartile 3 | Quartile 4 | $P_{trend}$[3] |
|---|---|---|---|---|---|---|
| Proximal colon cancer (n = 496) | F. nucleatum (+) colorectal cancer | | | | | |
| | No. of cases (n = 79) | 28 | 12 | 23 | 16 | |
| | Multivariable HR (95% CI)[2] | 1 (referent) | 0.38 (0.19-0.76) | 0.70 (0.40-1.23) | 0.46 (0.24-0.85) | 0.05 |
| | F. nucleatum (−) colorectal cancer | | | | | |
| | No. of cases (n = 417) | 89 | 98 | 110 | 120 | |
| | Multivariable HR (95% CI)[2] | 1 (referent) | 1.05 (0.78-1.40) | 1.06 (0.80-1.41) | 1.10 (0.82-1.47) | 0.47 |
| Distal colon and rectal cancer (n = 515) | F. nucleatum (+) colorectal cancer | | | | | |
| | No. of cases (n = 44) | 14 | 14 | 10 | 6 | |
| | Multivariable HR (95% CI)[2] | 1 (referent) | 0.98 (0.46-2.06) | 0.65 (0.28-1.48) | 0.38 (0.14-1.00) | 0.03 |
| | F. nucleatum (−) colorectal cancer | | | | | |
| | No. of cases (n = 471) | 117 | 123 | 123 | 108 | |
| | Multivariable HR (95% CI)[2] | 1 (referent) | 1.3 (0.80-1.33) | 0.96 (0.74-1.24) | 0.81 (0.61-1.07) | 0.07 |

[1]Tumors were classified as proximal if they were removed from the cecum to the transverse colon, distal if they were removed from the splenic flexure to the sigmoid colon, and rectal if they were removed from the rectosigmoid junction to the anal canal (excluding anal squamous cell carcinoma).
[2]Stratified by age, calendar year, and gender and adjusted for family history of colorectal cancer in any first-degree relative, history of previous endoscopy, pack-years of smoking (never, 0-4, 5-19, 20-39, or >40), body mass index (kg/m²), physical activity (MET-hours/week), regular aspirin or NSAID use (≥2 tablets/week), and total caloric intake (kcal/day).
[3]Tests for trend were conducted using the median value of each category as a continuous variable.
Abbreviations: CI, confidence interval; HR, hazard ratio; MET, metabolic equivalent task; NSAID, non-steroidal anti-inflammatory drug.

In a secondary analysis, Applicants sought to determine whether specific food groups might explain the observed differential associations between prudent dietary patterns and risk of colorectal cancer according to F nucleatum status. Applicants examined the top 4 dominantly contributing food groups to the prudent diet pattern (vegetables, fruits, legumes, and wholegrains) in relation to the risk of colorectal cancer according to F nucleatum status (Table 12). Applicants observed no significant heterogeneity (with the adjusted α of 0.01).

Finally, to further determine whether any specific macronutrient components of the prudent dietary pattern might explain the observed differential associations according to F nucleatum status, Applicants explored associations of fiber, fat, and protein intake with colorectal cancer subgroups (Table 13). There appeared to be heterogeneity in the differential association of fiber intake with cancer subgroups classified by F nucleatum status (P=0.02 for heterogeneity), similar to the findings for prudent dietary pattern scores. Comparing participants in the highest quartile of fiber intake (>26 g/d for men and >19 g/d for women) with those in the lowest quartile (<18 g/d for men and <13 g/d for women), the multivariable HR for F nucleatum-positive tumors was 0.54 (95% CI, 0.32-0.92); in contrast, the corresponding HR

TABLE 12

Hazard Ratios (HRs) of Incident Colorectal Cancer by F. nucleatum Status According to The Top Four Food Items (by Factor Loadings) in the Prudent Dietary Pattern in the Combined Cohort.

| | Quartile 1 | Quartile 2 | Quartile 3 | Quartile 4 | $P_{trend}$[2] | $P_{heterogeneity}$[3] |
|---|---|---|---|---|---|---|
| Vegetables | | | | | | |
| F. nucleatum (+) colorectal cancer (n = 125) | 29 | 34 | 31 | 31 | | |
| Multivariable HR (95% CI)[1] | 1 (referent) | 0.95 (0.58-1.57) | 0.80 (0.47-1.33) | 0.70 (0.42-1.18) | 0.12 | |
| F. nucleatum (−) colorectal cancer (n = 894) | 156 | 216 | 261 | 261 | | 0.03 |
| Multivariable HR (95% CI)[1] | 1 (referent) | 1.20 (0.97-1.48) | 1.33 (1.08-1.64) | 1.25 (1.01-1.56) | 0.08 | |
| Fruits | | | | | | |
| F. nucleatum (+) colorectal cancer (n = 125) | 31 | 31 | 37 | 26 | | |
| Multivariable HR (95% CI)[1] | 1 (referent) | 0.77 (0.47-1.28) | 0.84 (0.52-1.37) | 0.55 (0.32-0.95) | 0.04 | |
| F. nucleatum (−) colorectal cancer (n = 894) | 192 | 234 | 231 | 237 | | 0.22 |
| Multivariable HR (95% CI)[1] | 1 (referent) | 1.03 (0.85-1.25) | 0.91 (0.74-1.11) | 0.85 (0.68-1.05) | 0.04 | |
| Legumes | | | | | | |
| F. nucleatum (+) colorectal cancer (n = 125) | 23 | 40 | 38 | 24 | | |
| Multivariable HR (95% CI)[1] | 1 (referent) | 1.15 (0.68-1.96) | 0.94 (0.55-1.60) | 0.98 (0.54-1.79) | 0.83 | |
| F. nucleatum (−) colorectal cancer (n = 894) | 151 | 265 | 283 | 195 | | 0.60 |
| Multivariable HR (95% CI)[1] | 1 (referent) | 1.36 (1.11-1.67) | 1.26 (1.02-1.55) | 1.16 (0.92-1.47) | 0.39 | |
| Whole grains | | | | | | |
| F. nucleatum (+) colorectal cancer (n = 125) | 26 | 42 | 37 | 20 | | |
| Multivariable HR (95% CI)[1] | 1 (referent) | 1.07 (0.60-1.76) | 0.95 (0.57-1.58) | 0.56 (0.31-1.03) | 0.06 | |
| F. nucleatum (−) colorectal cancer (n = 894) | 151 | 264 | 247 | 232 | | 0.05 |
| Multivariable HR (95% CI)[1] | 1 (referent) | 1.31 (1.06-1.61) | 1.23 (0.99-1.52) | 1.17 (0.94-1.45) | 0.56 | |

[1]Stratified by age, calendar year, and gender and adjusted for family history of colorectal cancer in any first-degree relative, history of previous endoscopy, pack- years of smoking (never, 0-4, 5-19, 20-39, or ≥40), body mass index (kg/m²), physical activity (MET-hours/week), regular aspirin or NSAID use (≥2 tablets/week), and total caloric intake (kcal/day).
[2]Tests for trend were conducted using the median value of each quartile category as a continuous variable.
[3]We tested for heterogeneity by using a likelihood ratio test, comparing a model that allows separate associations for the two colorectal cancer subgroups (i.e., F. nucleatum positive and negative subgroups) with a model that assumes a common association.
Abbreviations: CI, confidence interval; HR, hazard ratio; MET, metabolic equivalent task; NSAID, non-steroidal anti-inflammatory drug.

for *F. nucleatum*-negative tumors was 1.13 (95% CI, 0.92-1.40). In further exploratory analyses, Applicants found that intakes of cereal-derived fiber might be differentially associated with colorectal cancer according to *F. nucleatum* status (P=0.01 for heterogeneity) (Table 14). Applicants did not observe such heterogeneity for fat or protein.

and incidence of colorectal cancer subgroups according to microbial status in human tumor tissue.

The potential role of diet in modulating the risk of a variety of diseases, including colorectal cancer, has been widely recognized. (Song et al., Gastroenteroloty 2015; 148(6):1244-60.e16; Tuddenham et al., Curr Opin Infect Dis

TABLE 13

Hazard Ratios (HRs) of Incident Colorectal Cancer by *F. nucleatum* Status According to Three Major Macronutrients in the Combined Cohort.

|  | Quartile 1 | Quartile 2 | Quartile 3 | Quartile 4 | $P_{trend}^2$ | $P_{heterogeneity}^3$ |
|---|---|---|---|---|---|---|
| Fiber |  |  |  |  |  |  |
| *F. nucleatum* (+) colorectal cancer (n = 125) | 30 | 27 | 41 | 27 |  |  |
| Multivariable HR (95% CI)[1] | 1 (referent) | 0.68 (0.40-1.16) | 0.87 (0.53-1.41) | 0.54 (0.32-0.92) | 0.04 |  |
| *F. nucleatum* (−) colorectal cancer (n = 894) | 164 | 230 | 236 | 264 |  | 0.02 |
| Multivariable HR (95% CI)[1] | 1 (referent) | 1.14 (0.93-1.40) | 1.08 (0.87-1.32) | 1.13 (0.92-1.40) | 0.40 |  |
| Fat |  |  |  |  |  |  |
| *F. nucleatum* (+) colorectal cancer (n = 125) | 28 | 28 | 31 | 28 |  |  |
| Multivariable HR (95% CI)[1] | 1 (referent) | 1.41 (0.86-2.30) | 1.27 (0.75-2.12) | 1.63 (0.96-2.78) | 0.10 | 0.29 |
| *F. nucleatum* (−) colorectal cancer (n = 894) | 237 | 234 | 230 | 193 |  |  |
| Multivariable HR (95% CI)[1] | 1 (referent) | 1.05 (0.87-1.26) | 1.12 (0.92-1.35) | 1.13 (0.92-1.37) | 0.17 |  |
| Protein |  |  |  |  |  |  |
| *F. nucleatum* (+) colorectal cancer (n = 125) | 32 | 36 | 37 | 20 |  |  |
| Multivariable HR (95% CI)[1] | 1 (referent) | 1.01 (0.62-1.63) | 1.08 (0.67-1.73) | 0.68 (0.39-1.18) | 0.27 | 0.72 |
| *F. nucleatum* (−) colorectal cancer (n = 894) | 225 | 243 | 246 | 180 |  |  |
| Multivariable HR (95% CI)[1] | 1 (referent) | 1.06 (0.89-1.28) | 1.08 (0.90-1.30) | 0.81 (0.66-0.99) | 0.05 |  |

[1]Stratified by age, calendar year, and gender and adjusted for family history of colorectal cancer in any first-degree relative, history of previous endoscopy, pack-years of smoking (never, 0-4, 5-19, 20-39, or >40), body mass index (kg/m$^2$), physical activity (MET- hours/week), regular aspirin or NSAID use (≥2 tablets/week), and total caloric intake (kcal/day).
[2]Tests for trend were conducted using the median value of each quartile category as a continuous variable.
[3]We tested for heterogeneity by using a likelihood ratio test, comparing a model that allows separate associations for the two colorectal cancer subgroups (i.e., *F. nucleatum*-positive and negative subgroups) with a model that assumes a common association.
Abbreviations: CI, confidence interval; HR, hazard ratio; MET, metabolic equivalent task; NSAID, non-steroidal anti-inflammatory drug.

Table 14—Hazard Ratios (HRs) of Incident Colorectal Cancer Subgroups by *F. nucleatum* Status According to Intakes of Three Major Subclasses of Dietary Fiber in the Combined Cohort. ([1]) Stratified by age, calendar year, and gender and adjusted for family history of colorectal cancer in any first-degree relative, history of previous endoscopy, pack-years of smoking (never, 0-4, 5-19, 20-39, or >40), body mass index (kg/m$^2$), physical activity (MET-hours/week), regular aspirin or NSAID use (≥2 tablets/week), and total caloric intake (kcal/day). ([2]) Tests for trend were conducted using the median value of each category as a continuous variable. ([3]) We tested for heterogeneity by using a likelihood ratio test, comparing a model that allows separate associations for the two colorectal cancer subgroups (i.e., *F. nucleatum*-positive and negative subgroups) with a model that assumes a common association. Abbreviations: CI, confidence interval; HR, hazard ratio; MET, metabolic equivalent task; NSAID, non-steroidal anti-inflammatory drug.

Discussion

In the 2 US nationwide prospective cohorts, Applicants found that participants with higher long-term prudent dietary pattern scores were associated with a lower risk of *F. nucleatum*-positive colorectal cancers but not *F. nucleatum*-negative cancers. Our data also suggest that higher intakes of dietary fiber, one of the components of the prudent diet, may be associated with a lower risk of *F nucleatum*-positive colorectal cancer but not *F. nucleatum*-negative cancer. These findings support the hypothesis that the possible cancer preventive effects of prudent diets rich in dietary fiber may be mediated by modulation of specific species in the gut microbiota and subsequent alteration of the amount of *F. nucleatum* in local colonic tissue. To our knowledge, our study represents the first to examine the intersection of diet 2015; 28(5):464-470). According to the World Cancer Research Fund and American Institute for Cancer Research, foods with fiber including whole grains are one of the strongest factors linked to decreasing the risk of colorectal cancer. (World Cancer Research Fund/American Institute for Cancer Research. Continuous update project:keeping the science current. Colorectal Cancer 2011 Report: food, nutrition, physical activity, and the prevention of colorectal cancer. http://wcrf.org/int/research-we-fund/our-cancer-prevention-recommendations. Accessed Apr. 21, 2016). However, there has been considerable heterogeneity in the epidemiologic data associating prudent dietary patterns and the major components of the prudent diet with colorectal cancer. (Aune et al., BMJ 2011; 343:d6617). Our results here suggest that the inconsistency in the association of prudent dietary patterns (and components of the diet) with lower colorectal cancer risk may be in part attributable to differential associations with cancer subgroups according to *F. nucleatum* in tumor tissue. In addition, given recent findings between increasing amounts of *F. nucleatum* DNA in colorectal cancer tissue and worsened survival, (Mima et al., Gut 2016; 65(12):1973-1980) our data lend additional support to the promotion of healthy diets to reduce mortality from colorectal cancer.

The precise mechanism by which prudent diets rich in dietary fiber may lower *F. nucleatum*-enriched cancer incidence remains unclear. Accumulating evidence suggests that long term dietary fiber intake has a profound effect on the gut microbiome, specifically through promotion of microbial diversity and by lowering levels of inflammatory metabolites. (Sonnenburg et al., Nature 2016; 529(7585): 212-215; Wu et al., Science 2011; 334(6052):105-108; Filippis et al., Gut 2016; 65(11):1812-1821; Ou et al., Am J Clin Nutr 2013; 98(1):111-120; Claesson et al., Nature 2012;

488(7410):178-184). A recent study showed that a 2-week feeding intervention switching rural-dwelling South Africans from a high-fiber, low-fat diet to a low-fiber, high-fat diet was associated with an increase in *F nucleatum* measured by PCR in the stool. (O'Keefe et al., Nat. Commun. 2015; 6:6342). In addition, some have hypothesized that the variation observed in *F nucleatum* levels in colorectal cancers collected from Spain, Vietnam, Japan, and the United States may be attributable to differences in dietary practices in these countries. (Kostic et al., Genome Res. 2012; 22(2): 292-298; Nosho et al., World J Gastroenterol 2016; 22(2): 557-566). Furthermore, in a cross-sectional study, participants with advanced adenoma were associated with lower dietary fiber intakes as well as distinct fecal microbiome communities compared with healthy controls. (Chen et al., Am J Clin Nutr. 2013; 97(5):1044-1052). It is plausible that an abundance of microbiota-accessible carbohydrates from prudent diets may influence bacterial fermentation of dietary fiber, resulting in altered levels of short-chain fatty acids. These changes may alter pH, increase transit time of gut contents, or lead to differences in local immune surveillance, which are less hospitable for nonnative species, such as *F nucleatum*, to establish themselves in the colonic niche and potentiate colorectal carcinogenesis. (O'Keefe et al., Nat. Commun. 2015; 6:6342; Sonnenburg et al., Nature 2016; 529(7585):212-215; Garrett et al., Science 2015; 348(6230): 80-86; Smith et al., Science 2013; 341(6145):569-573). Taken together, these data provide evidence of substantial influences of diet on the gut microbiome, which may in turn influence tumorigenesis.

There are several strengths in this study. First, our dietary data were prospectively collected and have been well validated. (Rimm et al., Am J Epidemiol 1992; 135(10):1114-1126). Second, our data were detailed and updated such that Applicants could examine long-term effects of overall dietary patterns, specific food groups, and macronutrients in relation to colorectal cancer risk. Third, Applicants collected detailed data on multiple potential confounders, although residual confounding cannot be excluded. Finally, our molecular pathological epidemiology (MPE) research (Ogino et al., Gut 2011; 60(3):397-411) provides refined risk estimates for specific cancer subgroups, such as *F nucleatum*-positive cancer, and thereby offers insights into pathogenesis and causality. Molecular subtyping in the MPE approach can gather pathogenetically similar cases, and thus can enhance statistical inference (even with a relatively small number of cases). (Ogino et al., Epidemiology 2016; 27(4):602-611). The present study represents emerging unique microbial MPE research (Hamada et al., Molecular pathological epidemiology: new developing frontiers of big data science to study etiologies and pathogenesis [published online Oct. 13, 2016], J. Gastroenterol.) in which the microbial feature in tumor tissue can serve as a pathogenic signature.

Limitations

Applicants acknowledge limitations of this study. First, this study was observational, and residual confounding may be an issue. Nevertheless, adjustment for a variety of known risk factors for colorectal cancer showed no substantial effect on the results. Second, the diet data were derived from food frequency questionnaires and subject to measurement errors. Nonetheless, studies have shown that food frequency questionnaires can better capture long term dietary intakes than detailed diet diaries in a limited period. (Willett et al., Nutritional Epidemiology, New York, NY: Oxford University Press; 2012). Third, with the use of FFPE tissue specimens, routine histopathologic procedures might have influenced performance characteristics of our PCR assay to detect *F nucleatum*. Nonetheless, Applicants conducted a rigorous validation study that showed high precision of our PCR assay to detect *F nucleatum*. (Mima et al., JAMA Oncol. 2015; 1(5):653-661). Moreover, our assay has previously been shown to have high specificity for *F nucleatum*. (Castellarin et al., Genome Res. 2012; 22(2):299-306). Fourth, Applicants could not collect FFPE blocks from all colorectal cancer cases in the cohorts; nonetheless, cases with available tissue were generally similar to those without tissue with regard to patient characteristics. Fifth, because our participants were all health professionals and most were white, generalizability of the findings to other populations needs to be examined in future studies.

CONCLUSIONS

This study has shown that a prudent diet is associated with a lower risk of *F nucleatum*-positive colorectal cancer but not *F nucleatum*-negative cancer. Our data generate new hypotheses about how the intestinal microbiota may mediate the association between diet and colorectal neoplasms. Further studies are needed to confirm these findings and determine the potential utility of characterization of *F nucleatum* in colonic mucosa, tumor, or stool as a biomarker for personalized nutritional, probiotic, or antibiotic interventions. In addition, our findings underscore the importance of future large-scale, prospective studies that examine the gut microbiota to understand the complex intersection of diet, the gut microbiome, and carcinogenesis. (Fu et al., *Ann Epidemiol*. 2016; 26(5):373-379).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of treating or preventing infection in a subject having a detectable colorectal *Fusobacterium* infection comprising:
   administering systemically 5-fluorouracil or an analogue thereof, or a prodrug of 5-flurouracil or analogue thereof to the subject.

2. The method of claim 1, further comprising detecting a Fusobacteria infection in the subject.

3. The method of claim 1, wherein the detectable *Fusobacterium* infection is an invasive *Fusobacterium* infection and wherein the infection is treated systemically.

4. The method of claim 2, further comprising detecting a co-occurring bacterial infection, wherein the co-occurring bacterial infection comprises a gram negative bacterial infection, an anaerobic bacterial infection, or both.

5. The method of claim 1, wherein the subject suffers from a primary colorectal cancer tumor and/or a distant colorectal metastases.

6. The method of claim 4, wherein the co-occurring bacterial infection further comprises bacteria of the genus *Selenomonas, Prevotella*, or any combination thereof.

7. The method of claim 1, wherein the detectable *Fusobacterium* comprises *Fusobacterium necrophorum*.

8. The method of claim 1, wherein the subject has a detectable co-occurring bacterial infection.

9. The method of claim 8, wherein the detectable co-occurring bacterial infection is an anerobic bacterial infection, a gram negative bacterial infection, or both.

10. The method of claim 1, further comprising detecting Fusobacteria in a sample, optionally a stool sample from the subject in need thereof.

11. The method of claim 1, further comprising detecting Fusobacteria nucleic acids in a sample from the subject in need thereof, wherein the sample is optionally a stool sample or a bodily fluid sample.

12. The method of claim 11, wherein the Fusobacteria nucleic acids are circulating nucleic acids.

13. The method of claim 11, wherein detection comprises use of a CRISPR effector system.

14. The method of claim 1, further comprising co-administering an antimicrobial agent comprising a *Fusobacterium*-selective antimicrobial agent, to the subject in need thereof.

15. The method of claim 1, wherein a 5-fluorouracil analogue is administered to the subject.

16. The method of claim 1, further comprising consuming a diet low in fat, low in lipid, low in carbohydrate, high in dietary fiber, or any combination thereof.

17. The method of claim 14, wherein the antimicrobial agent comprises penicillin, clindamycin, chloramphenicol, metronidazole, erythromycin, a macrolide, or any combination thereof.

18. The method of claim 9, wherein the gram-negative bacterial infection or the anerobic bacterial infection comprise bacteria from the genus *Selenomonas, Bacteroides, Prevotella*, or any combination thereof.

19. The method of claim 18, wherein
   (a) the *Bacteroides* genus bacteria comprise Bacterioides *fragilis*, Bacterioides *helcogenes*, Bacterioides *salanitronis*, or any combination thereof;
   (b) the *Selenomonas* genus bacteria comprise *Selenomonas ruminantium, Selenomonas sputigena*, or both;
   (c) the *Prevotella* genus bacteria comprise *Prevotella denticola, Prevotella intermedia*, or both; or
   (d) any combination of (a)-(c).

20. The method of claim 6 wherein
   (a) the *Bacteroides* genus bacteria comprise Bacterioides *fragilis*, Bacterioides *helcogenes*, Bacterioides *salanitronis*, or any combination thereof;
   (b) the *Selenomonas* genus bacteria comprise *Selenomonas ruminantium, Selenomonas sputigena*, or both;
   (c) the *Prevotella* genus bacteria comprise *Prevotella denticola, Prevotella intermedia*, or both; or
   (d) any combination of (a)-(c).

21. The method of claim 15, wherein the analogue is 1-hexylcarbamoyl-5-fluorouracil.

22. The method of claim 5, wherein the primary colorectal cancer tumor is a proximal colorectal cancer tumor.

23. The method of claim 5, wherein the distant colorectal metastases is a liver metastases or an abdominal wall metastases.

24. A method of treating or preventing infection in a subject having a detectable colorectal *Fusobacterium* infection consisting of:
   administering systemically 5-fluorouracil or an analogue thereof, or a prodrug of 5-flurouracil or analogue thereof.

* * * * *

SEQUENCE LISTING

<160> NUMBER OF SEQ ID NOS: 6

<210> SEQ ID NO 1
<211> LENGTH: 22
<212> TYPE: DNA

```
<213> ORGANISM: Artificial Sequence
<220> FEATURE:
<223> OTHER INFORMATION: Synthetic Primer

<400> SEQUENCE: 1
aagcgcgtct aggtggttat gt                                              22

<210> SEQ ID NO 2
<211> LENGTH: 23
<212> TYPE: DNA
<213> ORGANISM: Artificial Sequence
<220> FEATURE:
<223> OTHER INFORMATION: Synthetic Primer

<400> SEQUENCE: 2
tgtagttccg cttacctctc cag                                             23

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
caacgcaata cagagttgag                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
atccccaaag cacctggttt                                                 20

<210> SEQ ID NO 5
<211> LENGTH: 23
<212> TYPE: DNA
<213> ORGANISM: Artificial Sequence
<220> FEATURE:
<223> OTHER INFORMATION: Synthetic Primer

<400> SEQUENCE: 5
agaggccaag atagtcctgg taa                                             23

<210> SEQ ID NO 6
<211> LENGTH: 19
<212> TYPE: DNA
<213> ORGANISM: Artificial Sequence
<220> FEATURE:
<223> OTHER INFORMATION: Synthetic Primer

<400> SEQUENCE: 6
ccatccatgt cctcatctc                                                  19
```